United States Patent
Streit et al.

(10) Patent No.: US 11,759,564 B2
(45) Date of Patent: Sep. 19, 2023

(54) WEARABLE DRUG DELIVERY DEVICE

(71) Applicant: TecMed AG, Burgdorf (CH)

(72) Inventors: Ursina Streit, Kirchberg (CH); Roland Margot, Worb (CH); Jan Baumert, Grünen (CH); Simon Bosshard, Bern (CH); Michael Hanimann, Bern (CH); Fabian Steiner, Burgdorf (CH)

(73) Assignee: TecMed AG, Burgdorf (CH)

( * ) Notice: Subject to any disclaimer, the term of this patent is extended or adjusted under 35 U.S.C. 154(b) by 261 days.

(21) Appl. No.: 17/352,669

(22) Filed: Jun. 21, 2021

(65) Prior Publication Data

US 2021/0393872 A1 Dec. 23, 2021

(30) Foreign Application Priority Data

Jun. 23, 2020 (EP) ..................................... 20181604

(51) Int. Cl.
*A61M 5/142* (2006.01)
(52) U.S. Cl.
CPC ............. *A61M 5/14248* (2013.01); *A61M 2005/14252* (2013.01); *A61M 2207/00* (2013.01)
(58) Field of Classification Search
CPC ............. A61M 5/3202; A61M 5/14248; A61M 5/14244; A61M 2005/14252
See application file for complete search history.

(56) References Cited

U.S. PATENT DOCUMENTS

| | | |
|---|---|---|
| 5,597,990 A | 1/1997 | Carvalho et al. |
| 6,669,668 B1 | 12/2003 | Kleeman et al. |
| 6,699,218 B2 | 3/2004 | Flaherty et al. |
| 6,749,587 B2 | 6/2004 | Flaherty |
| 7,018,360 B2 | 3/2006 | Flaherty et al. |
| 7,303,549 B2 | 12/2007 | Flaherty et al. |
| 7,771,412 B2 | 8/2010 | Anderson et al. |
| 8,679,062 B2 | 3/2014 | Yodfat et al. |
| 9,993,595 B2 | 6/2018 | Michaud et al. |
| 2019/0091404 A1 | 3/2019 | Nazzaro et al. |

FOREIGN PATENT DOCUMENTS

| | | | |
|---|---|---|---|
| CA | 2625954 A1 * | 5/2007 | ........ A61M 5/14224 |
| EP | 1390089 B1 | 1/2007 | |
| EP | 1682203 B1 | 1/2010 | |
| EP | 3251585 A1 | 12/2017 | |
| EP | 3443996 A1 | 2/2019 | |
| EP | 3636298 A1 | 4/2020 | |
| WO | 03103763 A1 | 12/2003 | |
| WO | 2017120251 A1 | 7/2017 | |

* cited by examiner

*Primary Examiner* — Laura A Bouchelle
(74) *Attorney, Agent, or Firm* — Dorsey & Whitney LLP

(57) ABSTRACT

A drug delivery device for conducting a medical therapy includes a housing with an exit port opening, and an exit port assembly, where said exit port assembly includes a rigid exit port sealing holder and a soft exit port sealing, and provides both a fluid-tight closure of the exit port opening and a fluid-tight connection between the housing and the rigid exit port sealing holder.

14 Claims, 23 Drawing Sheets

Fig. 3b2
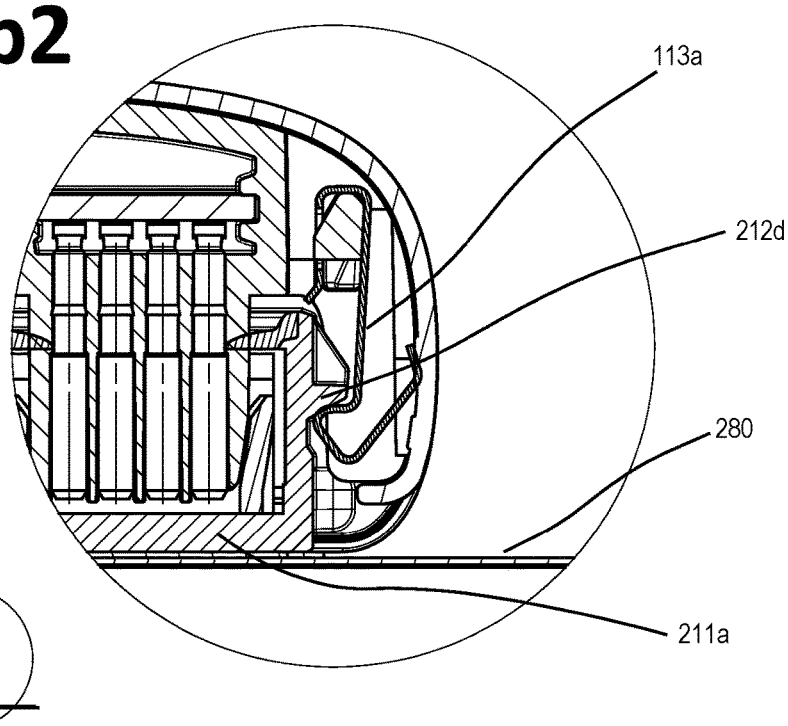
Fig. 3b1
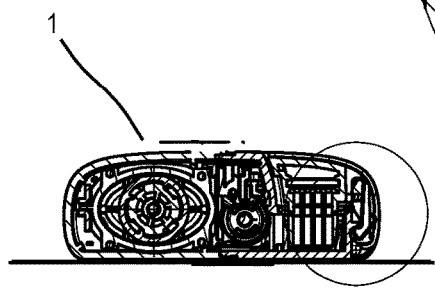
Fig. 4
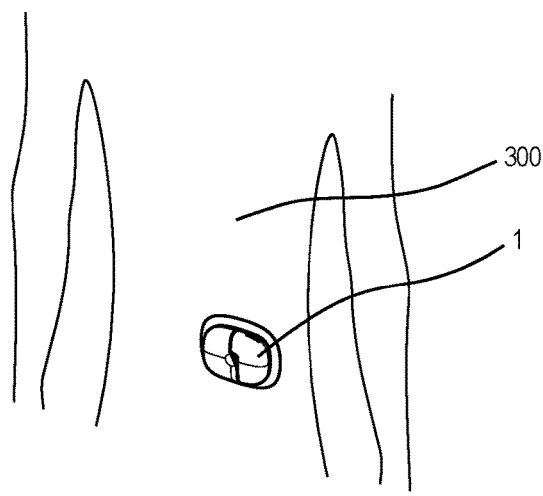

Fig. 22a1
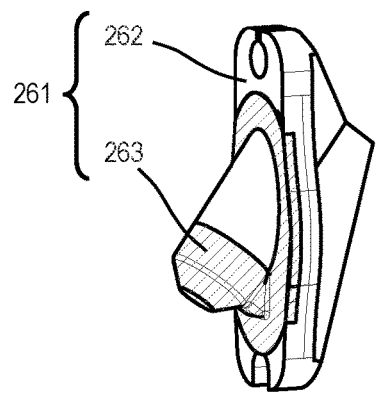
Fig. 22a2
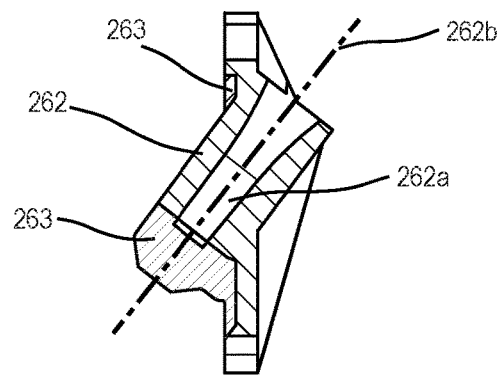
Fig. 22b
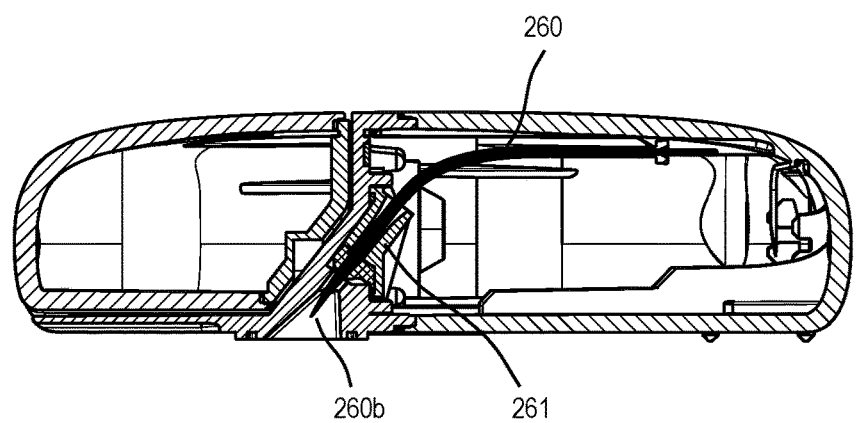

Fig. 25d1
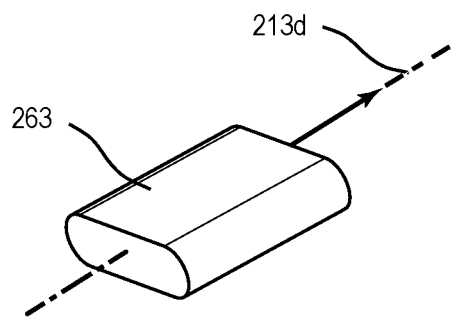
Fig. 25d2
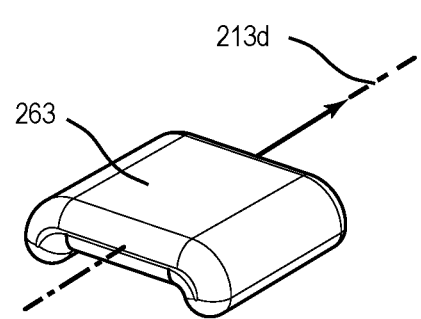
Fig. 25e
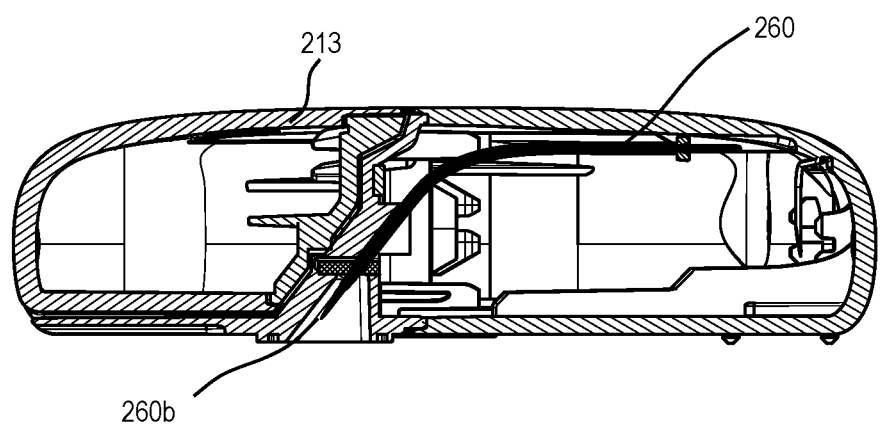

WEARABLE DRUG DELIVERY DEVICE

CROSS REFERENCE TO RELATED APPLICATIONS

This application claims priority to European Patent Application No. 20181604.8, filed Jun. 23, 2020, entitled "WEARABLE DRUG DELIVERY DEVICE," which is incorporated by reference herein, in its entirety and for all purposes.

TECHNICAL FIELD

Implementations relate to drug delivery devices, such as wearable patch pumps for subcutaneous delivery of a fluid medicament from a reservoir, and methods of their manufacture.

BACKGROUND

A variety of diseases exist that require regular treatment by subcutaneous administration of a medicament, and a number of drug delivery devices have been developed to support a patient in accurately and controllably delivering an amount of drug in a self-administration process. Delivery devices include drug delivery devices that are removed from the injection site after each medication event or drug delivery process, as well as infusion devices with a cannula or needle that remains in the skin of the patient for a prolonged period of time. By way of example, diabetes may be treated by administration of insulin by the patients themselves with the help of multi-variable-dose insulin injection pens or infusion pumps. Alternatively, patch injectors, wearable injectors or wearable pumps are patched or adhered to the skin of the patient.

Departing from classical syringes, increasingly complex devices have been designed to support different therapies, to ensure safety and reliability, and to increase ease of use to a point patients can apply the drugs themselves, reducing time-consuming and costly interventions by trained medical staff to a minimum. Examples of drug delivery devices suitable for self-treatment include injection pens, auto-injectors, portable infusion pumps and wearable patch pumps. Despite the technical complexity, it is an important requirement to keep cost of manufacturing and cost of devices as low as possible.

Common to all devices for subcutaneous drug delivery is a reservoir to store the fluid medicament, and a fluid path to bring the drug out of the device and into the subcutaneous tissue of a patient. Fluid-tightness of the fluid path is an essential requirement to ensure safety and accuracy of the delivery. Longer term infusion patterns and reliable system supervision functions particularly rely on controlled fluid pressure along the fluid path. While this is rather easy to achieve for a classic syringe, it becomes a challenge with increasing complexity of the device. Requirements are further increased by design for self-administration, which means use in a non-sterile environment, use by people without medical training, or even use by people with reduced visual or haptic capacities. The use of pre-filled cartridges, user-friendly fill ports, modular devices with disposable modules as well as wearable devices with auto-inserters are typical solutions to improve ease of use. Reducing the number of mechanical components and design for easy assembly during manufacturing are typical approaches to minimize cost.

U.S. Pat. No. 6,669,668 B1 discloses a drug delivery device with a disposable reservoir and a reusable pump module. The drug is manually filled into the disposable reservoir using a standard syringe. An administration set is used to bring the drug from the pump into the body of the patient.

An important step towards ease of use is to omit the administration set and design a wearable patch pump, which is small and has an adhesive patch to attach the pump to the patient during drug delivery. A typical patch pump design has a housing with a reservoir to contain the drug, a cannula to lead the drug into the body of a patient, and a needle assembly to establish a fluid-tight connection between the reservoir and the cannula. For optimum ease of use, the cannula is made of a soft material and an auto-inserting mechanism with a rigid needle or cannula is built into the pump to insert the soft cannula into the body of the patient for drug delivery. For compact and fluid-tight design, the reservoir is generally built into the housing and needs to be filled from outside prior to use. A number of sealing components are needed to ensure a fluid-tight design of the fluid path and of the housing. Special solutions are needed for the fill port, where the drug is brought into the reservoir, and for the exit port, where the cannula passes from the inside of the housing to the outside of the housing for drug delivery. Wearability calls for a compact design of the patch pump as a whole, which further adds to the complexity of design and manufacturing. As the most complex variation of subcutaneous drug delivery devices, semi-disposable patch pumps with internal auto-inserting mechanism and a soft cannula open the door to the most sophisticated therapies at the highest level of ease of use at a potentially low cost. Among other applications, they are a preferred solution for the intermittent delivery of insulin for the treatment of diabetes mellitus.

There is clearly a strong need for a wearable drug delivery device which provides accurate and reliable drug delivery in a compact, easy to use, fluid-tight and robust design and which can be manufactured at low cost. To arrive at an optimal solution, all involved components have to be designed accordingly.

U.S. Pat. No. 7,303,549 B2 describes a fully disposable patch pump for transcutaneous fluid delivery. While this concept includes an auto-inserting mechanism for the injection needle and offers a high level of ease of use, the lack of reusable parts brings the disadvantage of generating a lot of waste and increased cost of the therapy.

U.S. Pat. No. 8,679,062 B2 describes a semi-disposable patch pump describes a modular patch pump where one of the modules is reusable to reduce waste. However, ease of use is affected by the requirement to handle several different modules and by lacking the auto-inserting mechanism for the injection needle.

U.S. Pat. No. 9,993,595 B2 describes another example of a modular patch pump in a more compact design. Again, the missing auto-inserting mechanism affects ease of use.

For wearable delivery devices a compact design is of particular importance. The material used for such wearable drug delivery devices is usually plastic due to its advantageous manufacturing characteristics and its low density.

In other technical fields different types of material are often combined to benefit from advantageous characteristics from different materials. For example, U.S. Pat. No. 5,597,990 B1 discloses an electrical switch integrated in a switch-box and designed for detecting the presence of an electronic memory card in a card reader device. The housing of the switch box carries two fixed electrical contact elements which are arranged laterally on either side of the housing. Each fixed contact element is made of a folded metal blade whose free ends project out of the switch box to constitute terminals for connection and soldering on a printed circuit board. The contact elements are partially embedded into an overmolded plastic housing of the switch box.

In WO03103763, a patch injection device is disclosed comprising an external housing for containing a reservoir. The reservoir is closed by a needle insertion septum and may be filled by an external filling means using a fill port located in the housing.

In WO2017120251, a filling assist mechanism for a patch pump is disclosed comprising features to allow easier and more reliable filling of a reservoir located inside the patch pump. The reservoir is closed by a needle insertion septum and may be filled through a fill port located in the housing of the pump. The external filling assist mechanism comprises a cone shaped opening for guiding the needle of an external filling device. The very existence of the filling assist shows that the fill port as integrated in the patch pump is cumbersome to use.

US 2019/0091404 A1 discloses a cartridge-based drug delivery device where the reservoir has a sealing membrane at the outlet. To connect the reservoir outlet to the needle assembly and prepare the pump for drug delivery, the membrane is pierced by the needle assembly. In a compact design such a membrane can be difficult to manufacture.

U.S. Pat. No. 6,699,218 B2 describes a patch pump with a soft cannula and a rigid cannula slidably moving axially in the soft cannula for insertion. All connections along the fluid path are designed to prevent leaks, but no solution is given on how to design the interface between the two cannulas for fluid-tightness at a specified occlusion pressure. Fluid-tightness at a specified occlusion pressure is necessary for reliable detection of an occlusions in the fluid path.

The most common approach to an exit port sealing is by piercing a septum. One such arrangement is disclosed in EP 1390089 B1 as part of an infusion set. The more complex design of a patch pump with auto-inserting mechanism opens additional possibilities for new solutions by extending this basic concept and by optimising the exit port assembly for the specific requirements of the application.

An exit port assembly for a patch pump with soft cannula and inserting mechanism is disclosed in EP 1682203 B1. The assembly as disclosed includes a multitude of sealing components, making it more costly and less than optimal for manufacturing.

U.S. Pat. No. 7,771,412 B2 describes an environmental seal for a fluid delivery device where the exit port is designed as a cap which comprises two different components and is mounted into a housing. Although 2-shot molding is mentioned as a way to improve manufacturability and reduce cost, the proposed exit port is rather complex. The soft plug remains in the inside of the cap and is not arranged in a way allowing combination with other functions for further optimisation.

In a patch pump with auto-inserting mechanism a fluid connection between the reservoir and the output of the cannula is established when manufacturing the pump. This open path can affect the accuracy of drug delivery or also the function of the filling process. It is therefore desirable to close this path until the drug delivery is intended to start. An objective is to provide a solution for the closure of the exit port which is easy to use and suitable for low cost manufacturing.

U.S. Pat. No. 7,018,360 B2 discloses a semi-permeable exit plug to support filling and priming a patch pump with needle inserting mechanism. The plug may be a sheet attached to the adhesive release liner of the adhesive patch. Although simple, this concept is prone to tearing the semi-permeable sheet in the process of removal of the plug and calls for a solution with improved reliability and hence improved ease of use.

U.S. Pat. No. 6,749,587 B2 discloses a patch pump where the adhesive is provided in a continuous ring encircling the exit port assembly to provide a protective seal around the penetrated skin. Again, this simple concept can be extended to include other functions and find an overall optimum.

EP 3251585 A1 discloses an adhesive patch assembly for a patch pump, including structures to improve reliability of the connection with the body of the patient by letting air and humidity pass from the surface of the skin to the environment. This concept can also be extended and combined with other functions to achieve an optimum of reliability and ease of use.

It is an objective of the present disclosure to provide an improved drug delivery device which is accurate, reliable, easy to use and cost effective, overcoming the drawbacks of or introducing alternatives to the prior art. Several aspects of the present disclosure contribute to the improved device. These aspects may be applicable to a variety of drug delivery devices such as pen injectors, patch injectors, mobile pumps or patch pumps.

Also provided are improved assembly methods for the drug delivery device as disclosed in the corresponding claims.

SUMMARY

The term "substance", "drug", "medicament" or "medication" includes any flowable medical formulation suitable for controlled administration through a means such as, for example, a cannula or a hollow needle and includes a liquid, a solution, a gel or a fine suspension containing one or more medical active ingredients. A medicament can be a composition including a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from—or harvested by—biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

The distal end or distal direction is defined by the direction of the needle configured to penetrate the skin of the patient. For an injection pen this may be the injection needle and the end of the pen holding the needle or being configured to hold the needle is the distal end. For an infusion device the distal end and the distal direction is towards the needle configured to penetrate the skin of the patient, which may be along the axis of the device or tilted or perpendicular to the axis of the device. The distal direction in an infusion device represents the direction in which the medicament flows towards the insertion needle. The proximal direction or end is opposite to the distal direction or end.

The term "injection system" or "injector" refers to a device that is removed from the injection site after each medication event or drug delivery process, whereas the term "infusion system" refers to a device with a cannula or needle that remains in the skin of the patient for a prolonged period of time, for example, several hours. If not explicitly mentioned otherwise, the term "pump" is referring to an infusion system, in the context of the present disclosure typically to a patch pump.

In the claims, the word "comprising" does not exclude other elements or steps, and the indefinite article "a" or "an" does not exclude a plurality. For example "sealing" or "protrusion" does not exclude the fact that there may be two "sealings" or "protrusions" that functionally or structurally fulfil the purpose of "a sealing" or "a protrusion".

In a first aspect of the present disclosure, a modular, semi-disposable patch pump is provided with reusable components. The semi-disposable patch pump may include: a reservoir unit, which may be configured for single use, and a pump unit, configured for multiple or continuous use. Providing two units may reduce waste while also reducing the number of handling steps the patient performs to apply the pump.

The reservoir unit may include a reservoir unit housing and a base plate mounted on an adhesive patch, and the base plate may be attached to or integrated into the bottom of the reservoir unit housing, and may include all components intended for single use, such as all components in contact with the drug and the adhesive patch. Drug carrying components may include a reservoir with a reservoir outlet, a pump mechanism, and a needle assembly connected to the outlet of the reservoir to transport the drug from the reservoir into the body of the patient. To facilitate use, the reservoir unit may further include an inserter assembly which includes an auto-inserting mechanism to insert the needle into the body of the patient without any force being applied by the user. The pump mechanism may for example include a plunger movably mounted in the reservoir, allowing the drug to be pressed out of the reservoir through the reservoir outlet by moving the plunger. Any kind of energy may be used to drive the auto-inserting mechanism, such as energy stored in the reservoir unit including a pre-loaded insertion spring, or energy originating from outside, including a rotation generated by the pump unit. This may also include the possibility of using the same drive unit to drive or release the auto-inserter as used for driving the pump mechanism. The pump unit may include all components intended for multiple or continuous use, for example a pump unit housing, an electrical power source such as a rechargeable battery, a drive mechanism with a driving means to drive the pump mechanism in the reservoir unit, acoustic and/or visual and/or haptic elements to interact with the user, a communication unit to send and/or receive data to/from other system components, and a control unit to control the device. In an embodiment where the pump mechanism is a plunger movably mounted in the reservoir, the driving means may for example be a combination of a motor, gearing and coupling to a threaded rod in cooperation with a plunger rod.

The pump unit may be further configured to be releasably attachable to the reservoir unit, and implementations provide approaches for how the reservoir unit and the pump unit may be mechanically connected. The connection may be safe and reliable, allowing easy separation of the pump unit and the reservoir unit for replacement of the disposable parts, while providing safety and reliability when it comes to unintended separation or removal of the pump unit during normal use.

The patch pump, with both units connected, may form a substantially edge-free shape for wearability and to avoid unintended removal of the patch pump from the body of the patient. The outer shape enveloping the pump components during normal use may also contribute to avoiding unintended detaching of the pump unit from the reservoir unit. To further facilitate use, the mechanical interface between the reservoir unit and the pump unit may include a bayonet coupling, and no button may need to be pressed or no slider may need to be moved to release the connection, while providing a mechanical connection that maintains rigidity with minimal axial play to provide for accurate and reliable drug delivery.

The pump unit may be pushed onto the reservoir unit at an angle of at least 5 degrees, such as at least 15 degrees and folded down onto the plane of the base plate, thereby closing the substantially edge-free enveloping outer surface of the pump. The closing movement of the reservoir unit may be substantially a rotation around an axis defined by the bayonet connection. To open the bayonet, the user may pull on the side of the reusable unit facing away from the rotational axis of the bayonet, where the pump unit may be lifted off the plane of the base plate to release the pump unit.

While the semi-disposable patch pump of the present disclosure may include any kind of locking mechanism for the bayonet connection, other locking mechanisms allowing the same handling step to unlock and open the connection may also be provided. Examples of such locking mechanisms may include a mechanical latch snapping in and out by pushing and pulling, a magnetic lock, or a pair of Velcro® strips.

Although the enveloping outer shape of the patch pump may be provided for wearability, unlocking and detaching the pump unit may still occur if the body part of the patient where the pump is attached inadvertently brushes over an edge. The edge may slide under the patch pump on the opening side, causing the pump unit to be lifted off the plane of the base plate. The locking mechanism may open and the pump unit may be brushed off the body of the patient. To avoid this kind of unintended detaching, the patch pump of the present disclosure may include a base plate extending from the bottom of the reservoir unit housing between the opening side and the bayonet axis in the direction of the pump unit. While this extended base plate may reduce the risk of unintended detaching of the pump unit from the reservoir unit, it may make it difficult for the patient to remove the pump unit intentionally. Therefore, the patch pump according to the present disclosure may include a cut-out at the edge of the base plate. The effect of the cut-out may be that a finger of the patient can at least partially slide under the pump unit on the opening side of the pump, while a longer edge may still be kept outside. To achieve this effect, the cut-out may have a length of 5 mm to 30 mm, or 15 to 25 mm, and a width of 1 mm to 10 mm, or 3 mm to 5 mm.

The patch pump according to the present disclosure may reduce the number of handling steps required to apply the pump, while also reducing the waste generated by the therapy. Additional features may facilitate the safety of the patch pump despite its ease of use.

In a second aspect of the present disclosure, a compact design of a drug delivery device is provided. In this aspect, a drug delivery device with a reservoir for holding a liquid drug, a needle assembly for delivery of the drug, and a base frame is provided.

According to the second aspect of the present disclosure, the drug delivery device may include a base frame including an electrically conductive connector structure with electrical contact areas for establishing an electrical connection between the base frame and an external device. The base frame may further include a non-conductive body injection-molded around the connector structure, such that the electrical contact areas may be contactable by the external device from outside the non-conductive body. The base frame may further be integrated into or form a part of the housing of the drug delivery device.

The present aspect of the disclosure may further include the base frame itself for a drug delivery device as described in the previous paragraph, the base frame including an electrically conductive connector structure including electrical contact areas for establishing an electrical connection and a non-conductive body injection-molded around the connector structure such that the electrical contact areas may be contactable from outside the non-conductive body, where the non-conductive body includes a guiding member for guiding a movement of the needle assembly, combined with the non-conductive body to form a unitary component.

According to prior art approaches, different electrical contact elements and a support for holding the contact elements in place inside the drug delivery are separately mechanically connected to each other, for example by heat staking (e.g., thermoplastic staking), by riveting, by insertion or pressing into sockets, or by using snap lock connections. The different electrical elements may be complex to handle. Furthermore, establishing an electrical connection between the different elements may require a considerable number of manufacturing steps.

According to the second aspect of the present disclosure the base frame as a support structure may allow the number of individual components to be reduced and may also allow several functions to be combined in one assembly. The electrical connector structure may include electrical conductors, contacts, tracks or strip lines that may be adapted to establish an electrical connection between electrical components supported or held by the non-conductive body. The connector structure may be formed by only one component or a small number of components. The non-conductive body of the drug delivery device may be injection-molded around the connector structure. This may allow for the integration of various other supporting elements into the non-conductive body, which may form a unitary component with extended functionality. Other supporting elements may be, for example, supporting pins for a printed circuit board, retaining elements for retaining a battery on the non-conductive body, guiding elements for guiding a moveable needle assembly or other moveable elements of the inserter mechanism, or stop elements to stop such a movement. By reducing the number of components the base frame according to the present disclosure may allow for a compact design of the drug delivery device.

The electrically conductive parts or connector members of the connector structure may be made of any electrically conductive material such as metal, metal alloys, conductive plastics or a conductive composite material. The connector structure may provide an electrical connection between the components supported by the base frame and external devices, which may be inseparably or releasably connected to the electrical contact areas of the base frame. Furthermore, the connector structure may provide electrical connections between various electrical and/or electronic components supported or guided by the base frame.

The connector structure may include only one single conductive part or connector member or it may include multiple conductive parts or connector members. For instance, the connector structure may include at least two separate connector members which may be electrically insulated from each other. In this case, all connector members of at least one connector structure may be manufactured as one single component in a first production step, for example one single sheet of metal. The shape of the sheet may include all connector members plus some connecting bridges between them to form one single conductive component. In a second production step, the conductive sheet or component may be overmolded, forming one unitary component with a non-conducting frame that may hold all connector members as well as the connecting bridges. In a third production step the connecting bridges may be removed, for example by blanking, which may result in a unitary component containing a connector structure with one or more separated electrical pathways. This manufacturing process may be considerably easier and more time efficient than using the overmolding technology with two or more conductive connector members all inlaid as separate components.

The electrical contact areas may be integrated into the connector structure to form one unitary component. However, as mentioned above, the connector structure itself may include more than one conductive part or connector member. For instance, a first electrical contact area may be formed in a first connector member and a second electrical contact area may be formed in a second connector member, wherein the first and the second electrical contact area may be galvanically distinct and separated from each other. In this case the first electrical contact area may be adapted to be connected to a positive pole and the second electrical contact area may be adapted to be connected to a negative pole.

The non-conductive body of the drug delivery device may be injection-molded around the connector structure and may thus at least partially envelop the connector structure. The connector structure may therefore be supported or held by the non-conductive body. This may allow the connector structure to be securely placed, for example, inside a housing of the drug delivery device. The non-conductive body may be made of electrically non-conductive plastic, non-conductive composite material or any other non-conductive injection-moldable material.

The non-conductive body may be one unitary component. Several elements such as, for example, retaining elements, guiding tracks, mechanical stop elements, supporting elements or bearing pins may be formed integrally in the non-conductive body. That means the elements may be made of the same material as the non-conductive body.

The non-conductive body may be injection-molded around the connector structure such that the electrical contact areas of the connector structure may be contactable from outside the non-conductive body. That means that the non-conductive body may be designed to avoid preventing the electrical contact areas of the connector structure from establishing contact with the intended connecting contact. The electrical contact areas of the connector structure may be designed, for example, in form of arms or levers protruding out of the non-conductive body or the non-conductive body may have an opening or a recess allowing an external device to be contacted with the electrical contact areas through the opening or recess.

The connector structure and the non-conductive body injection-molded around the connector structure may form a hybrid component or a unitary component manufactured using two-component (2C) molding technology. This technology is also known as insert molding or overmolding technology.

The drug delivery device may be an infusion system or an injection system. The drug delivery device may be, for example, an injection pen or it may be a patch injector applicable onto the skin of the user for the duration of the injection. The infusion system may be, for example, a conventional medical drug pump such as an insulin pump with an infusion set, or it may be a drug patch pump without infusion set and attachable directly onto the skin of the user.

In some embodiments, the drug delivery device may be a patch pump including a reusable part and a disposable part. The reusable part may include a drive mechanism and a control unit. The disposable part may be adapted to be replaced after each infusion and may include a reservoir with the drug, a hybrid assembly with the needle assembly, a cannula moving assembly to move at least a portion of the needle assembly, and a base frame. In this implementation, the cannula moving assembly may include relevant parts of the inserter assembly associated with the movement of the needle assembly, such as holders for a rigid cannula and for a soft cannula.

In some embodiments, the non-conductive body may form a guiding member for guiding a movement of the needle assembly itself or the cannula moving assembly. The term "form" means the guiding member is integrally formed in the non-conductive body in one unitary component. Thus, the guiding member is made of the same material as the rest of the non-conductive body.

The guiding member may guide the moveable portion of the needle assembly or the cannula moving assembly along a linear or straight movement path, along a curved path, along a rotational path or along a combination of linear, curved and rotational movement path. The guiding member may be provided, for example, in the form of a rail, a nut, a protrusion or a profile.

Since the guiding member may be formed in the non-conductive body as one unitary component, no means for connecting the guiding member to the non-conductive body may be required, e.g., no snap or screw connection may be needed. The guiding member may allow for an easy and quick movement of the cannula and/or other portion of the needle assembly, for example, from a start or initial position to an extended or inserted position, where the cannula is inserted into the skin of the user.

The guiding member may be a linear guiding rail for guiding the needle assembly itself or a portion of the cannula moving assembly along a linear movement path. "Linear" means the movement path is a straight line such that the needle assembly shifts along a straight line. The guiding member may include one or more guiding rails. For instance, the guiding element may include at least one guiding rail adapted to engage with a corresponding counterpart, for example a groove, of the needle assembly and/or the cannula moving assembly.

The non-conductive body may include an end stop surface integrated in the non-conductive body as a unitary component and the end stop surface may be adapted to restrict a movement of the needle assembly or the cannula moving assembly in a first direction. The end stop surface may be integrally formed in the non-conductive body. For instance, the end stop surface may define either an extended position or an initial position of the needle assembly. The needle assembly may be moveable from an initial or start position to the extended or inserted position, where the cannula has pierced the skin of the user. The end stop surface may be, for example, a bump stop, a buffer or an element protruding in the direction of movement of the needle assembly.

The connector structure may be at least partly or mainly made of metal. That means the connector structure may be either completely made of metal or made of metal and other material components, conductive composite materials or made of metal and additional non-metal materials. For instance, the connector structure may be made of one electrical conductive metal sheet. This may allow for an easy and efficient production of the connector structure.

For instance, the connector structure may be made by blanking and bending. This means the contours of the connector structure may be defined in a first step by blanking the connector structure from a metal sheet, and in a second step the connector structure may be further formed by bending. If the connector structure includes more than one connector member the connector members may be initially mechanically connected to each other via auxiliary or temporary bridges or connectors. These bridges may be eliminated or interrupted by a punching step after the non-conductive body has been injection-molded around the circuit. That means that the finished connector structure may include several galvanically distinct and separated connector members or other electrical pathways. In this way, the connector structure may be produced efficiently and at lower cost.

In examples, the connector structure may include at least two electrical contact areas. For instance, each of the at least two electrical contact areas may be arranged on a resilient element or contacting arm of a connector member. That means the connector structure may include at least two connector members each including a resilient element or contacting arm carrying an electrical contact area. The electrical contact areas may thus bounce or flex when an external element mechanically and electrically contacts the electrical contact areas. That may help to establish an electrical connection between the external contact element and the electrical contact areas of the connector structure. An external contact element may belong to another device like a charger, or may belong to any other system component connectable to the connector structure like a unit of a modular pump or an add-on for monitoring an injection or infusion process.

For instance, the drug delivery device may include a switching arm protruding flexibly outside the base frame and may be formed in a first connector member in one unitary component. Hence, the switching arm may be made of the same material as the connector structure. The switching arm may be directly or indirectly electrically contactable with a second connector member. The first and the second connector member may be galvanically separated from each other. If the switching arm electrically contacts the second connector member an electrical connection may be established between the first and second connector member and thus an electrical signal may be transmitted. Hence, the switching arm may be switched by the movable cannula moving assembly between a conductive state and a non-conductive state.

The generated signal may indicate, for example, whether or not a release button is pressed, an external device is connected or the needle assembly is moved into a specific position. Of course, the switching arm may be positioned such that the button, the external device or the needle assembly may mechanically contact the switching arm to switch the lever between the conductive state and the non-conductive state.

For instance, the switching arm may be switchable by the needle assembly or by the inserter assembly such that the switching arm establishes an electrical connection or interrupts an existing electrical connection between the first connector member and the second connector member.

The switching arm may be positioned next or near the movement path of the cannula moving assembly or the needle assembly such that an element (for example, an edge, a protrusion, an actuating lever) of the cannula moving assembly or the needle assembly may mechanically contact and thus switch the switching arm. The conductive state (electrical connection) or the non-conductive state (connection electrically interrupted) of the switching arm may be indicative that the needle assembly is in an initial position or in an extended position or that it is no longer in the initial or extended position.

In examples, the non-conductive body may be at least partly or mainly be made of plastic. The non-conductive body may include only plastic or mainly plastic and other materials or composite material, which may be electrically non-conductive. In either case, the material of the non-conductive body may be injection-moldable and may thus be used for overmolding the connector structure.

Further, the non-conductive body may include a retaining element for retaining a battery integrated into the non-conductive body as one unitary component. Furthermore, the connector structure may include battery contact elements for electrically contacting the retained battery integrated into the connector structure as one unitary component. The retaining element may be, for example, an arm, a clamp, a retaining tab or a tongue. The battery may thus be reliably held relative to the non-conductive body. The battery may be a button cell, a conventional cylindrical battery or an accumulator. If the battery is retained and held in place by the retaining element, the battery may mechanically and electrically contact the battery contact elements of the connector structure. The battery contact elements may be provided, for example, in form of pins, tabs, tongues or arms and may be integrated into the connector structure as one unitary component.

The connector structure may form at least two battery contact elements. To electrically contact the battery, a first battery contact element may be adapted to be connected to the positive pole and a second battery contact element may be adapted to be connected to the negative pole of the battery.

Implementations further relate to a base frame for a drug delivery device with a needle assembly, and in some cases includes an inserter assembly with a cannula moving assembly. The base frame may include an electrically conductive connector structure including electrical contact areas for establishing an electrical connection and a non-conductive body injection-molded around the connector structure such that the electrical contact areas may be contactable from outside the non-conductive body. The non-conductive body may include a guiding member for guiding a movement of the needle assembly or the cannula moving assembly, that may be integrated into the non-conductive body as one unitary component. Furthermore, implementations relate to a hybrid assembly including the herein described base frame, the cannula moving assembly and the needle assembly.

In examples, the hybrid assembly may further include a heater assembly or a melt release module with a heating element for releasing a piercing process with the needle assembly. The heater assembly may be supported by the non-conductive body.

The releasing of the piercing process may involve a linear or rotational movement of the needle assembly from an initial or start position to an extended position, where the cannula has pierced the skin of the user. The heating element of the heater assembly may melt or break a fuse, which may hold the biased needle assembly or cannula moving assembly in its initial position. If the fuse is melted or broken, an insertion trigger or retaining means of the hybrid assembly may break or expand such that the biased needle assembly or cannula moving assembly is free to move the cannula and to pierce the skin of the user with a portion of the needle assembly.

The heater assembly with the heating element may be directly, or indirectly via a further element, supported by the non-conductive body and arranged on said non-conductive body.

For controlling the insertion process, the hybrid assembly may include a printed circuit board (Reservoir unit printed circuit board, PCB-RU) supported and held by the non-conductive body. The heating element of the heater assembly and other controlling elements may be arranged on the PCB-RU.

For instance, a holding structure for rigidly holding the PCB-RU on the non-conductive body may be integrated into the non-conductive body as one unitary component. The structure may include pins, tabs or arms formed as one unitary component. The PCB-RU may be fixed to holding structure, for example, by an adhesive, by heat staking or by a snap lock.

The design of a sealing for a drug delivery device is not an isolated task. Fluid-tightness is defined for a specific area or volume, according to pressure requirements derived from the intended functionality. To arrive at the design of the present disclosure, the following pressure requirements have been specified:
 to allow successful filling of the reservoir through a fill port in the housing, at least the reservoir sealing and the fill port sealing are fluid-tight (e.g., sealingly fluidly connected) to a filling pressure of at least 6 bar
 to allow successful occlusion detection, at least the sealing of the fluid path of the medicament is fluid-tight to an occlusion pressure of at least 2 bar
 to allow successful protection from ingress from the environment, at least the sealing of the housing is fluid-tight to an environmental overpressure of at least 0.24 bar.

It may be particularly important to fulfil these requirements for sealing at all interfaces involved in the function of the drug delivery device. It may be further evident that the values of the pressure requirements given above are just examples to explain the advantages of the present disclosure, and shall by no means restrict the application of the concepts described in the present disclosure to a specific pressure range.

In a third aspect of the present disclosure, an improved fill port assembly is provided. The improved fill port assembly may provide fluid-tightness at filling pressure, facilitate easy assembly, enhance the longevity and robustness of the device, and may additionally fix the reservoir with respect to the housing.

These objectives may be realized by providing by a drug delivery device for delivery of a medicament from a reservoir to a patient, including: a housing with a wall separating an interior volume from the exterior, a reservoir being arranged in the interior volume, a fill port assembly arranged in the wall of the housing and accessible from the exterior for filling the reservoir, the fill port assembly including a cone shaped opening for receiving a needle and a pierceable fill port sealing separating the reservoir from the exterior. The fill port assembly may include an insert adapted to be received by a passage in the wall of the housing and the fill port sealing may provide a sealing between the housing and the reservoir. The sealing between the housing and the reservoir may prevent fluid from passing between the reservoir and the wall of the housing.

The current aspects of the present disclosure may be applied to a drug delivery device for delivery of a medicament from a reservoir, where the medicament may be a liquid or a solid that is reconstituted prior to the injection. The reservoir may be a cartridge or non-collapsible reservoir or collapsible reservoir made from a flexible material. The drug delivery device may include a housing with a wall separating an interior volume from the exterior. The housing may be constructed in any number of components connected together to form a substantially closed shell around the interior volume. The reservoir may be arranged in the interior volume. A fill port assembly may be arranged in, or may be part of, the wall forming the housing and may be accessible from the exterior for filling the reservoir. The reservoir may be filled at the factory or the user may fill the reservoir prior to use. The reservoir may be a multiple use reservoir. Optionally, the reservoir may be filled only once and the unit including the reservoir may be discarded after use. The fill port assembly may include a cone or conical shaped opening adapted to receive a needle. The cone shaped opening may facilitate the entry of the needle of a filling or transfer device, for example, a syringe containing the medicament for filling an empty reservoir with the medicament. The fill port assembly may include a pierceable fill port sealing separating the reservoir from the exterior. The pierceable fill port sealing may include a pierceable septum. The fill port sealing or the septum of the sealing may be pierced by the needle for filling the reservoir. Furthermore, the fill port assembly may include an insert adapted to be received by a passage in the wall of the housing or in the fill port sealing where the fill port sealing is received in the passage of the housing. The fill port assembly may be assembled from an exterior of the housing. The fill port sealing may provide a sealing between the housing and the reservoir. The fill port sealing may provide a plurality of sealings to different sections or components within the drug delivery device, and the sealing may be a direct sealing between the housing and the reservoir, or an indirect sealing via other housing parts. Combining multiple sealings in the fill port assembly may reduce the number of parts needed. Using an insert as part of the fill port assembly may have the advantage that during assembly, the insert may be inserted from the outside into the passage in the wall and may also fix other parts (for example housing parts) or components such as the reservoir with respect to at least part of the housing of the drug delivery device or the reservoir unit of the drug delivery device, and may simultaneously establish the sealing or plurality of sealings. Thus, the fill port assembly may combine the features of enabling the filling of an empty reservoir, sealing of the reservoir with respect to the housing, and fixation of the cartridge or reservoir. The use of an insert separate from the housing may have the advantage that the two parts may be adapted to their specific needs. The insert may be made from a different material than the housing and thus may reduce manufacturing costs or be made of a material having a different stiffness or wear resistance, which may result in reducing the risk of particle abrasion, needle clogging or needle damage. The cone shaped opening may further facilitate the needle insertion through the fill port, for instance for the visually impaired users.

The insert of the drug delivery device may include the cone shaped opening and the cone shaped opening may extend from a base. The cone shaped opening may define a longitudinal axis and the base may be connected to the larger diameter access of the cone and may be oriented perpendicular to the longitudinal axis. The outer dimensions of the base may fit into a first recess or recessed section of the housing or the wall of the housing. The cone shaped opening of the insert may thus be adapted to receive and guide the needle tip, for example, towards the septum of the fill port sealing. The cone shaped opening may have an angle with respect to the longitudinal axis. The opening of the cone may be wide to facilitate access of the needle tip. The cone angle between the longitudinal axis and the cone surface may range between 20 and 40 degrees, between 25 and 35 degrees, or the cone angle may be approximately 30 degrees.

The fill port sealing may be sandwiched between the base of the insert and the wall of the housing to provide a first sealing between the insert and the housing. The first sealing may prevent leakage of fluids and/or gases from inside the housing to the exterior, or contamination from the exterior entering into the housing. The first sealing may provide sterility and protect parts inside the housing from the exterior. The first sealing may additionally or alternatively enhance the shelf life or longevity of the device.

The fill port sealing may include a flange or a rim which may be made from compressible or elastic material such as an elastomer. The flange may be adapted to be received in a second recess or recessed section surrounding the passage in the wall of the housing. The first recessed section for the insert may be different from the second recessed section for the flange of the fill port sealing. Both recessed sections may surround the passage and the second recessed section for the flange may be deeper compared to the first recessed section for the insert. The second recessed section for the flange may be adapted to receive the flange or rim and may have a lateral dimension smaller than the lateral dimensions of the first recessed section adapted to receive the base of the insert. The flange may be sandwiched between the insert (or the base of the insert) and the wall. The first sealing may be an axial sealing oriented along the longitudinal axis of the conical shaped opening and arranged between the base of the insert and the housing or the recessed section surrounding the passage of the housing. Reception of the flange of the fill port sealing in the second recessed section in the wall may secure the fill port sealing from lateral movement and align the parts, e.g., passage in the housing, fill port sealing and insert, prior to final assembly and/or fixation of the cartridge. The wall of the housing in the second recessed section configured to receive the fill port sealing and/or the base of the insert facing the fill port sealing may have protrusions or protruding structures to locally compress the resilient sealing material of the flange.

The drug delivery device may include a fill port additionally sealing an inlet of the reservoir. The inlet of the reservoir may be oriented parallel to the longitudinal axis of the fill port assembly (e.g., parallel to the longitudinal axis of the cone shaped opening) and the inlet of the reservoir may be aligned with respect to the passage in the housing once the device has been assembled. The inlet of the reservoir may be oriented perpendicular to the longitudinal axis of the reservoir. The inlet of the reservoir may also be aligned with respect to the cone shaped opening and the septum that may be part of the fill port sealing such that penetration of the septum by the needle may ensure that medicament can be filled into the reservoir. The fluid port assembly may thus provide a fluid tight closure of the reservoir, for instance, of the inlet of the reservoir and may thus prevent leakage of medicament from the reservoir into the housing or to the exterior. The fluid port assembly may also prevent contamination from the exterior entering the reservoir and may be part of a sterile barrier.

The fill port sealing of the drug delivery device may provide a second sealing between the fill port sealing and the inlet of the reservoir, and the sealing may be oriented in a radial direction perpendicular to the longitudinal axis of the cone shaped opening. The second sealing may be axially displaced from the first sealing. Two sealing functions in one part may be enabled by arranging the two sealings at different locations, both having (independent) sealing properties and the material or dimensions may be adapted to the specific needs.

The insert and the fill port sealing may fix the reservoir with respect to the housing. Thus, by inserting the fill port sealing and insert from the outside into the housing, the reservoir may be fixed which may already be present inside the housing. The fixation may be based on a form-fit fixation, alternatively using a friction or force fit. The fixation may additionally benefit from a snap-fit connection between the reservoir, or the inlet of the reservoir and at least one of the parts forming the fill port assembly. The fixation may use the fill port assembly or parts thereof being at least partially arranged inside the inlet of the reservoir. Alternatively, a neck section or the body of the reservoir may be used for the fixation. Using the fill port assembly additionally for fixing the reservoir implies that sealing and fixation may be combined, which may improve the assembly of the device and reduce parts.

The fill port sealing may include a bore extending from the flange and terminate in the pierceable septum. The bore may be formed by a cylindrical section connecting the pierceable septum to the flange of the fill port sealing. For instance, the pierceable septum may form an end of the bore. The cylindrical section may connect the first and second sealings.

The insert of the drug delivery device may include a sleeve extending from the cone shaped opening, starting from the narrow section of the cone shaped opening, and the sleeve may be adapted to be received within the bore of the fill port sealing. The cone thus may connect the base to the sleeve. The sleeve may be connected to the narrow end of the cone shaped opening and may extend along the longitudinal axis of the cone. The sleeve may guide the needle tip from the cone shaped opening towards the pierceable septum of the fill port sealing. The guidance may ensure that the septum is pierced perpendicular to a membrane forming the septum to help prevent tearing of the septum and leakage along the needle during filling of the reservoir. The guidance may also prevent the needle from contacting the inner wall of the inlet, which may bear the risk of abrading particles from the inlet wall and of reducing the depth of piercing. Furthermore, the sleeve of the insert may be coaxially arranged within the bore formed by the cylindrical section of the fill port sealing. The sleeve of the insert, the cylindrical section of the sealing and the inlet of the reservoir may be coaxially arranged for insertion of the insert and sealing during assembly and for reservoir fixation of the assembled device. The reservoir may be fixed by mounting the fill port assembly since the base of the insert may be fixed in at least one of the recessed sections of the housing and may prevent lateral movement of both the fill port sealing and the reservoir.

An outside surface of the fill port sealing or an outside surface of the cylindrical section may be at least partially received in the inlet of the reservoir.

The outside surface of the cylindrical section may be press fitted into the inlet of the reservoir, which may thereby: a) establish the second sealing (due to resilience or partial resilience of outside surface of the cylindrical section), and b) fixate the reservoir from lateral movement. The fill port assembly may fixate the reservoir such that shock absorption may be provided between the reservoir and the housing, for instance, due to the elastic properties of the outside surface of the cylindrical section engaging the inlet of the reservoir. This may be advantageous for the device for improving the impact resistance, for example, during a drop test.

The insert for the drug delivery device may be made from a metal such as steel, such as stainless steel, or aluminium. Alternatively, the insert may be made from a plastic material coated with a metal layer or from a plastic material that may be strengthened with a mineral filler such as glass, zirconia or aluminium oxide particles. One advantage of using a metal or a toughened plastic may be to prevent the needle tip from abrading particles from the insert or even getting stuck in the insert. Another advantage of using a metal or a toughened plastic may be to improve the wear resistance of the insert to an extent that the reservoir may be used multiple times, e.g., a needle may be guided and inserted through the fill port assembly multiple times without damaging the insert. Therefore, the longevity of the insert, and therewith the device, such as a re-usable device, may be improved.

The fill port sealing may include a thermoplastic polymer and an elastomer. For instance, the elastomer may surround the thermoplastic polymer. The advantage may be that the thermoplastic polymer has a higher modulus for providing the mechanical strength for fixation of the reservoir, while at the same time may improve suitability for assembly during manufacturing of the pump. A potential advantage of using the elastomer is that the elasticity may be beneficial for forming the sealings and optionally for shock absorption. Examples for the thermoplastic polymers may be polybutylene terephthalate (PBT), polycarbonate or polycarbonate alloys such as cycoloy (e.g., polycarbonate/acrylonitrile butadiene styrene blends), acrylonitrile butadiene styrene copolymers (ABS) or a high modulus polyurethane (PUR). Examples for the elastomer may be an ethylene propylene diene monomer (EPDM) rubber, polydimethylsiloxane (PDMS) rubber, for instance in polysiloxane liquid silicone (LSR) form or an elastomeric polyurethane (PUR) or a thermoplastic elastomer (TPE). The thermoplastic polymers and elastomers may be selected to fulfil the biocompatibility requirements according to ISO 10993 as parts of the fill port sealing may be in contact with the medicament. The thermoplastic polymer and elastomer may be injection molded using 2-component injection molding, and may reduce the number of parts, as a plurality of functions may be combined in a single part.

The insert of the fill port assembly, such as the base of the insert, may include a recess or an opening or cut-out configured to receive a fixing pin extending from the wall of the housing. The insert may include a plurality of recesses, openings or cut-outs adapted to engage a plurality of fixing pins. The fixing pins may be integrally formed on the housing and may be made from a thermoplastic polymer. The fixing pins may be oriented substantially parallel to the cone axis and the engagement between the cut-outs and the fixing pins may ensure that after mounting, the insert may be correctly aligned with the other parts of the fill port assembly and the housing. The engagement between the fixing pins and the openings may facilitate the assembly and may ensure that the insert is rotationally fixed with respect to the housing. The insert may be fixed to the housing by heat staking of at least one of the fixing pins, for example, by heating and deforming a fixing pin. This axial and rotational fixation may provide reliable and sufficient contact pressure of the fill port sealing and hence for achieving the intended sealing function of the fill port up to the specified filling pressure.

The drug delivery device according to this aspect of the present disclosure may allow the assembly of the fill port from exterior of the housing, and may use a separate insert for fixing of the septum and of the reservoir. The insert may be made from a different material compared to the housing material.

The current aspect of the present disclosure may also provide an improved method for assembling the drug delivery device with a fill port described herein, and may include the steps of:

providing the housing, the reservoir, the fill port sealing and the insert, inserting the reservoir from the exterior into the housing along an axis that is perpendicular to the cone axis, which may be followed by, inserting the fill port sealing from the exterior along the cone axis into a passage in the wall of the housing, which may be followed by, inserting the insert from the outside in the fill port sealing, which may thereby sandwich the fill port sealing (e.g., the flange of the fill port sealing) between the insert (e.g., the base of the insert) and the housing and establish the first and second sealings and fix the reservoir to the housing.

The method may additionally include the following step:

Positioning the opening or cut-out of the insert on the fixing pin extending from the wall of the housing of the drug delivery device or the disposable unit, followed by heat staking of the fixing pin to fix the insert to the housing. Alternatively, the insert may be fixed to the housing using ultrasonic welding, laser welding, using an adhesive or heat welding.

In a fourth aspect of the present disclosure, a sealing for a drug delivery device may be provided at the interface of the reservoir and the needle assembly leading the drug out of the reservoir towards the cannula. The reservoir outlet sealing design may ensure fluid-tightness (e.g., a sealing fluid connection) at occlusion pressure, may facilitate easy assembly and may enhance the longevity and robustness of the device.

These objectives may be realized by providing a drug delivery device including a housing with a reservoir arranged inside the housing to contain a drug; a needle assembly with an input portion and an output portion; and a pierceable reservoir outlet seal; where the reservoir includes an at least partially rigid reservoir housing with an at least partially cylindrical reservoir outlet sealing cavity, integrated into the reservoir housing as a unitary component; the reservoir outlet sealing may be at least partially cylindrical and configured to be inserted into the reservoir outlet sealing cavity during manufacturing of the patch pump, to be pierced by the input portion of the needle assembly during manufacturing, and to form a fluid-tight connection between the reservoir and the input portion of the needle assembly. The at least partially cylindrical design of the reservoir outlet sealing may contribute to ensuring fluid-tightness at the filling and/or occlusion pressure and to an easier assembly process compared to other geometries. In a variation of this design, the soft reservoir outlet sealing may be manufactured together with the rigid reservoir housing using 2-shot injection molding as a unitary component.

In a fifth aspect of the present disclosure, a sealing of a drug delivery device may be provided at the interface of the rigid cannula as part of the input portion of the needle assembly, and the soft cannula as part of the output portion of the needle assembly. The soft cannula input sealing design may ensure fluid-tightness at occlusion pressure, may facilitate easy assembly and may enhance the longevity and robustness of the device.

These objectives may be realized by providing a drug delivery device including a housing with a reservoir arranged inside the housing to contain a drug; a needle assembly with an input portion and an output portion; where the needle assembly includes a soft cannula having an open distal end, and a rigid cannula at least partially and slidably disposed in an inner soft cannula lumen of the soft cannula; the proximal input end of the rigid cannula may be part of the input portion of the needle assembly and the distal output end of the soft cannula may be part of the output portion of the needle assembly; where the proximal input end of the soft cannula may form a sliding soft cannula input sealing configured to slide on the rigid cannula while applying a tightening pressure to ensure a fluid-tight sealing at the occlusion pressure.

In a sixth aspect of the present disclosure, a sealing of a drug delivery device may be provided at the interface of the housing and the output portion of the needle assembly. The exit port sealing may ensure fluid-tightness of the housing at environmental pressure, may reduce the number of components of the drug delivery device, may facilitate easy assembly, may save cost and may enhance the longevity and robustness of the device.

These objectives may be realized by providing a drug delivery device including a housing with an enveloping surface separating an interior volume from the exterior; a reservoir arranged inside the housing to contain a drug; a needle assembly with an input portion and an output portion; and an exit port assembly, where the housing may include at least two components configured to be attached to one another to form a protective shell of the drug delivery device; the reservoir may include a reservoir outlet coupled to the input portion of the needle assembly; the housing may include an exit port opening to provide a passage for the output portion of the needle assembly from the interior of the housing to the exterior; the exit port assembly may be configured to form a fluid-tight connection between the housing and the output portion of the needle assembly; the exit port assembly may include a rigid exit port sealing holder with an at least partially tubular exit port channel defining an exit port channel axis configured to receive the output portion of the needle assembly, and a soft exit port sealing may be attached to the rigid exit port sealing holder during manufacturing of the drug delivery device; the soft exit port sealing may be configured to be pierced by the output portion of the needle assembly during manufacturing of the drug delivery device; and where the soft exit port sealing may be further configured to provide a fluid-tight closure of the exit port opening of the housing when the exit port assembly is mounted on the housing.

Three exemplary approaches are provided as follows:

An exit port sealing design may be provided by using a 2-shot injection molding process to manufacture the exit port assembly as a unitary component including the rigid exit port sealing holder and the soft exit port sealing.

Another exit port sealing design may be provided by joining the exit port assembly together with one of the at least two housing components and by using a 2-shot injection molding process to manufacture the exit port assembly as a unitary component including at least one of the at least two housing components, the rigid exit port sealing holder, and the soft exit port sealing. By including a part of the housing, this multi-functional component may further include other sealings of the housing, such as the sealing at the mechanical interface between the reservoir unit and the pump unit of a semi-disposable patch pump.

A further exit port sealing design may be provided by adapting the rigid exit port sealing holder to further include an exit port sealing plug cavity defining an exit port sealing plug cavity axis, and the exit port sealing plug cavity may be open on at least one end to receive the soft exit port sealing; the exit port sealing plug cavity may be arranged to intersect the exit port channel with an angle of at least 10 degrees, such as at least 45 degrees, between the exit port channel axis and the exit port sealing plug cavity axis; the exit port sealing plug cavity axis and the exit port channel axis may intersect at an angle of at least 10 degrees, such as at least 45 degrees; the soft exit port sealing may be inserted into the exit port sealing plug cavity during manufacturing of the drug delivery; and the soft exit port sealing may be configured to tightly close the exit port sealing plug cavity and the exit port opening when mounted in the rigid exit port sealing holder.

A feature of the exit port sealing design may be provided by modifying the exit port sealing plug cavity to include a constriction and/or flattening at the exit port opening, which may improve pressing and/or shaping of the soft exit port sealing at the intersection with the exit port channel. Increased pressing may bring fluid-tightness at a higher pressure, and a flat shape of the exit port sealing may facilitate piercing during manufacturing.

A further feature of the exit port sealing design may be provided by modifying, in at least one of the devices described herein, the shape of the housing, and by introducing a recess from the enveloping surface of the housing at the exit port opening. With the exit port arranged in a recess, the patch pump may be manufactured ready to use with the output portion of the needle assembly extending through the exit port, providing adequate sealing and ease of use without having any part protruding from the enveloping surface of the housing. Further, the recess in the housing may form an external exit port chamber between the recessed exit port opening and the enveloping surface of the housing, which may allow filling of the reservoir and filling of the fluid path prior to use without risk of injecting any medicament into the body of the patient. By filling the fluid path with medicament before inserting the cannula into the body of the patient and before starting the drug delivery the pump may avoid infusing air instead of medicament at the beginning of the infusion process and may improve the accuracy of drug delivery.

The features of the exit port sealing design according to the present disclosure, may be used in a semi-disposable patch pump with a needle assembly, where the needle assembly may include a soft cannula having an open distal end, a rigid cannula at least partially and slidably disposed in an inner soft cannula lumen of the soft cannula, and a needle insertion mechanism configured to bring the output portion of the needle assembly with at a least the open distal end of the soft cannula from a first position inside the exit port chamber to a second position outside the exit port chamber in the exterior of the housing. Such an insertion mechanism may improve ease of use.

In a seventh aspect of the present disclosure, a sealing of a patch pump may be provided at the interface of the housing and the external environment in the area of the exit port prior to the application of the pump to the body of the patient. The exit port lid design may help ensure fluid-tightness at a minimal filling pressure as specified for the use of the patch pump, may support the process of filling and priming and may facilitate easy assembly and use of the device.

These objectives may be realized by providing a drug delivery device with an exit port arranged in a recess of the housing—such as for example the device described in the previous aspect of the present disclosure—and an exit port lid, where the exit port lid may be removably attached to the housing at a portion of the housing surrounding the exit port opening; the exit port lid may cover the exit port chamber such that fluid is prevented from entering or exiting the exit port chamber while permitting passage of air; the exit port lid may include a membrane of any semi-permeable material adapted to permit air to pass through while preventing liquid from passing therethrough; the exit port lid may include a membrane reinforcing structure permanently, e.g., non-detachably, fixed to the membrane which may ensure the membrane is not damaged in the process of removing the exit port lid from the housing. Such a membrane reinforcing structure may be a plastic sheet with a cut-out for the exit port opening.

In an eighth aspect of the present disclosure, a sealing of a patch pump may be provided at the interface of the housing and the external environment in the area of the exit port after attaching the pump to the body of the patient. The design of the housing and the design of the adhesive patch assembly may improve the reliability and robustness of drug delivery, and may also provide an easier and more comfortable use of the patch pump.

These objectives may be realized by providing a drug delivery device as described herein and using as a patch pump with an adhesive patch assembly to attach the pump to a patient, where the adhesive patch assembly includes an adhesive layer configured to attach the adhesive patch assembly to the patient after preparation of the patch pump for drug delivery; the adhesive patch assembly may include a removable adhesive release liner to protect the adhesive layer from unintended adhesion prior to use, such as during preparation of the patch pump for drug delivery; the exit port lid may be fixed permanently, e.g., non-detachably, to the adhesive release liner and removably connected to the housing; and the exit port lid may be configured to be removed from the housing together with the adhesive release liner during preparation of the patch pump for drug delivery.

The design of the housing and the adhesive patch assembly in the area of the exit port may be useful for a patch pump as described herein, where the housing may further include a membrane carrying structure arranged around the exit port chamber; the membrane carrying structure may be adapted to protrude from the housing towards the exterior by a height substantially the same as the thickness of the adhesive patch assembly; the membrane carrying structure may be configured to provide contact with the exit port lid in a state when the exit port lid is removably attached to the housing; the membrane carrying structure may be configured to provide a fluid-tight connection between the exit port lid and the housing during preparation of the patch pump for drug delivery, and may thereby tightly close the exit port chamber. While reliably attaching the adhesive patch assembly to the body of the patient, for instance in the area of the exit port, may be important for the reliability of the drug delivery, a further improvement of the patch pump design at the interface of the housing and the external environment in the area of the exit port may be to introduce, at a distance from the exit port, a number of airing or venting channels. These may allow air and/or humidity leave the interface and improve the adherence of the patch pump to the body of the patient during drug delivery. This may be provided with a patch pump as described herein, where the housing and/or the adhesive patch assembly may further include at least one ventilation structure with at least one inner end closed and arranged at a horizontal distance of 1 mm to 20 mm, such as 5 mm to 10 mm, from the exit port chamber, and at least one outer end left open and arranged at the peripheral edge of the housing and/or the adhesive patch. The horizontal distance of the airing channel from the exit port chamber may be important to maintain a tight closure around the exit port and avoid a connection of the ventilation structure with the exit port chamber. The ventilation structure may be configured to let air pass from the inner end to the outer end and to the environment of the patch pump. During drug delivery, the airing channel formed by the ventilation structure may be on the surface of the body of the patient—if the ventilation structure is provided in the adhesive patch assembly—or more towards the housing—if the ventilation structure is formed by the housing or by another layer of the adhesive patch assembly.

BRIEF DESCRIPTION OF THE DRAWINGS

The subject matter of the present disclosure is detailed in the following text with reference to various implementations, which are illustrated in the attached drawings, in which:

FIGS. 2a and 2b refer to the mechanical interface between the pump unit and the reservoir unit in which:

FIG. 2a depicts the drive mechanism of the patch pump across the two units;

FIG. 2b depicts the bayonet connection between the pump unit and the reservoir unit of a patch pump;

FIGS. 3a, 3b1 and 3b2 refer to the step of attaching the Pump Unit to the Reservoir Unit of a patch pump in which:

FIG. 3a depicts the patch pump with the pump module connecting the bayonet of the reservoir module at an angle of 30°;

FIG. 3b1 depicts a cross-section of the patch pump at the locking mechanism, with locking mechanism closed;

FIG. 3b2 depicts an enlarged view of details of the locking mechanism of FIG. 3b1;

FIG. 4 depicts the patch pump attached to the body of a patient and ready for drug delivery;

FIGS. 6a and 6b refer to a perspective view of the hybrid assembly with the cannula moving assembly in which:

FIG. 6a depicts a perspective view of the hybrid assembly with the cannula moving assembly in the initial position;

FIG. 6b depicts the hybrid assembly of FIG. 6a but with the cannula moving assembly in the extended position;

FIGS. 8a-8c refer to a perspective view of the base frame in which:

FIG. 8a depicts a perspective view of the base frame including a non-conductive body and a connector structure;

FIG. 8b depicts a perspective view of the non-conductive body of the base frame, bottom-up;

FIG. 8c depicts the connector structure of the base frame;

FIGS. 9a, 9b1 and 9b2 refer to a perspective view of the reservoir unit with a fill port, after fixation by hot stemming in which:

FIG. 9a depicts a perspective view of a reservoir unit, partially assembled and turned bottom up to show the fill port at the bottom of the unit;

FIG. 9b1 depicts a cross section of the reservoir unit with a fixed fill port assembly and reservoir inlet;

FIG. 9b2 depicts an enlarged view of details of the reservoir unit with the fixed fill port assembly and reservoir inlet of FIG. 9b1;

FIG. 10b depicts an enlarged view of details of the reservoir unit of FIG. 10a;

FIG. 11b depicts an enlarged view of details of the reservoir unit of FIG. 11a;

FIG. 12b depicts an enlarged view of details of the reservoir unit of FIG. 12a;

FIGS. 21a and 21b refer to a schematic view of a patch pump with an exit port in which:

FIG. 21a depicts a patch pump with an exit port in a flat area of the housing;

FIG. 21b depicts a patch pump with an exit port in a housing with a recess at the exit port;

FIGS. 22a1 to 22b refer to the exit port assembly of a first implementation of an exit port in which;

FIG. 22a1 depicts an implementation of the exit port assembly in a perspective view;

FIG. 22a2 depicts the exit port assembly in a cross-section view;

FIG. 22b depicts a cross-section view of an implementation of a patch pump with the exit port assembly of FIGS. 22a1 and 22a2, fully assembled;

FIGS. 23a-23c depict the exit port assembly of a second implementation of an exit port in which:

FIG. 23a depicts the exit port assembly in perspective view, cut through the exit port channel;

FIG. 23b depicts a cross-section view of the exit port assembly;

FIG. 23c depicts a cross-section view of an implementation of a patch pump with the exit port assembly of FIG. 23a, fully assembled;

FIGS. 24a1-24d depict the exit port assembly of a third implementation of an exit port;

FIG. 24a1 shows a housing component with integrated rigid exit port seal holder in a perspective view from outside, before inserting the soft exit port sealing;

FIG. 24a2 shows the housing component with the integrated rigid exit port seal holder of FIG. 24a1 in a cross-section view;

FIG. 24d depicts a cross-section view of the exit port after piercing the sealing by the needle assembly;

FIGS. 25a1-25e refer to the exit port assembly of a fourth implementation of an exit port in which:

FIG. 25a1 shows a housing component with integrated rigid exit port seal holder in a perspective view from outside, before inserting the soft exit port sealing;

FIG. 25a2 shows the housing component with the integrated rigid exit port seal holder of FIG. 25a1 in a cross-section view taken across the exit port;

FIG. 25d1 depicts a soft exit port sealing before insertion into the exit port sealing cavity of FIG. 25b;

FIG. 25d2 depicts the soft exit port sealing after insertion into the exit port sealing plug cavity of FIG. 25b;

FIG. 25e depicts a cross-section view of the exit port after piercing the sealing by the needle assembly;

FIGS. 26a-26c refer to an exit port with an exit port chamber and an exit port lid in which:

FIG. 26a depicts an exit port lid closing the exit port chamber;

FIG. 26b depicts an exit port lid in an embodiment with a membrane carrying structure;

FIG. 26c depicts an exploded view of an adhesive assembly combined with an exit port lid.

The reference symbols used in the drawings, and their primary meanings, are listed in summary form in the list of designations. In principle, identical parts are provided with the same reference symbols in the figures.

DETAILED DESCRIPTION

As outlined in the introductory paragraphs, the present disclosure has a number of aspects, all contributing to the implementations of the drug delivery device of the present disclosure which may provide a device that is accurate, reliable and easy to use while still suitable for conducting complex therapies at as low cost as possible. While the implementations are explained using the example of a wearable patch pump as shown in FIGS. 1a, 1b, 2a, and 2b, it will be appreciated these aspects of the present disclosure may also be used in connection with other drug delivery devices, wherever a comparable feature is present. Cost effectiveness may be realized by the introduction of the manufacturing and/or assembly methods for the drug delivery device as provided herein.

Figure 1A:
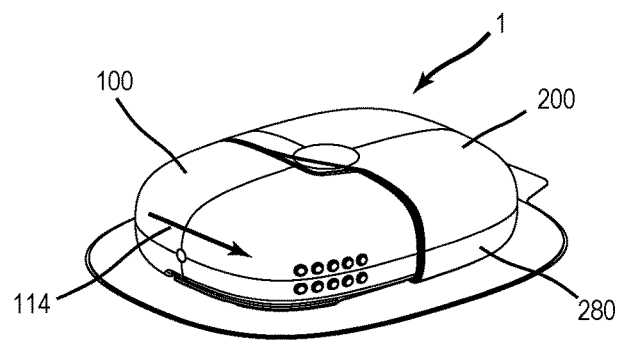
FIGS. 1a and 1b depicts a perspective view of a patch pump as seen from above (away from patient, left) (FIG. 1a) and from below (towards the patient, right) (FIG. 1b)
Figure 1B:
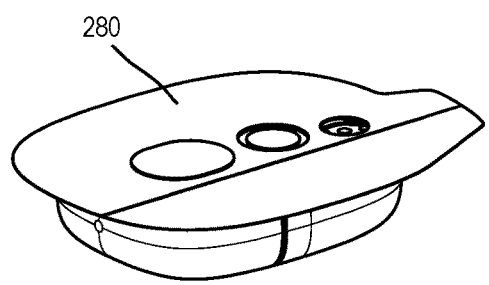

FIGS. 1a and 1b depict a perspective view of a drug delivery device according to the present disclosure. The drug delivery device may be provided as a patch pump 1. The patch pump 1 may include a reusable pump unit 100 and a disposable reservoir unit 200. The reservoir unit 200 includes a reservoir configured to store the medicament and a needle assembly with a fluid path configured to bring the drug from the reservoir into the body of the patient. At the bottom of the reservoir unit 200, an adhesive patch assembly 280 may be included and attach the patch pump 1 to the body of the patient. The pump unit 100 may be releasably and sealingly connected to the reservoir unit 200 by a bayonet connection 212a (FIG. 2b). FIG. 1a shows the complete patch pump 1 with both units connected and seen from a position above the pump. In the context of the present disclosure, "above" or "top" refers to the side of the pump which is facing away from the patient's body when the pump is attached to the patient for drug delivery. Consequently, "bottom" or "base" refers to the side of the pump facing towards the patient's body during drug delivery. In FIG. 1a, the arrow at the opening side 114 indicates the direction towards the opening side 114 of the patch pump 1, where the pump unit 100 is lifted off the bottom of the reservoir unit 200. FIG. 1b shows the same pump turned over for a bottom view of the patch pump 1, with the adhesive patch assembly 280.

Figure 2A:
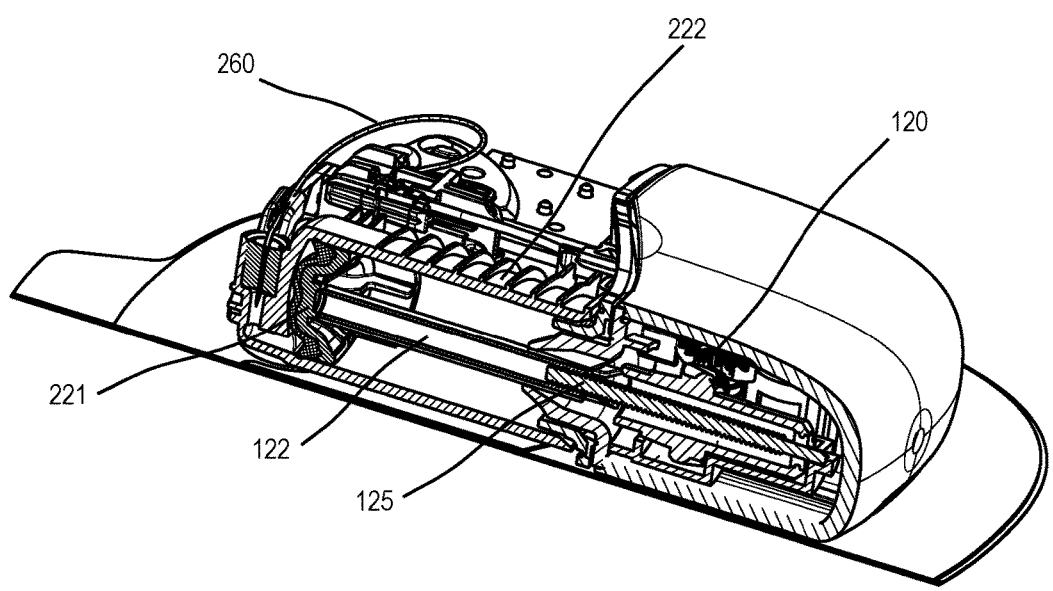
Figure 2B:
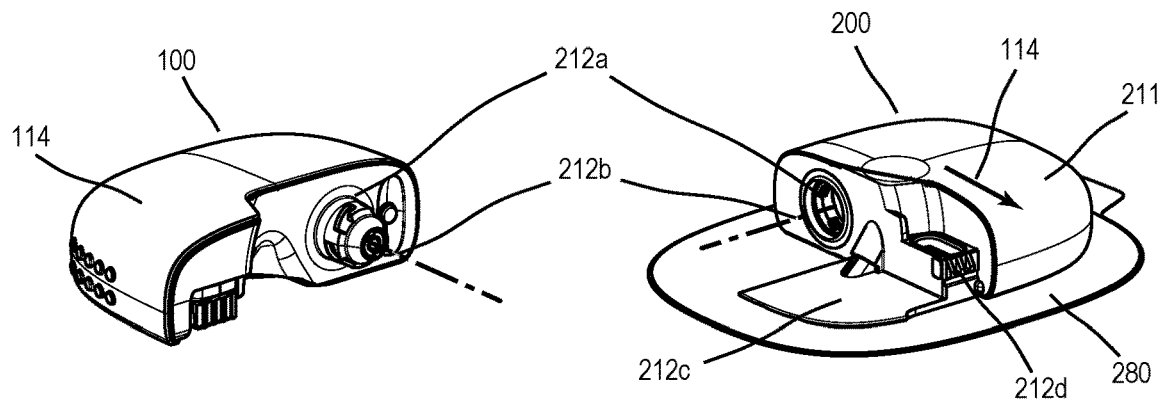

As illustrated in FIG. 2a, the pump unit 100 may include a drive mechanism for driving the plunger rod 122, an encoder to supervise the movement of the drive mechanism, a rechargeable battery and programmable electronic system control circuitry configured to control the set-up, drug delivery and supervision of the pump. The battery may be recharged by a further battery in the disposable reservoir unit 200 while the drive mechanism is connected to the reservoir unit 200.

The drive mechanism 120 may act mechanically from a threaded rod 125 via plunger rod 122 on a plunger 221 in the reservoir 222 to dispense the medical substance out of the reservoir 222. A needle assembly 260 inside the reservoir unit may provide the fluid connection from the reservoir 222 to the exterior of the pump for application to the patient. For safe handling, the patch pump may be manufactured, shipped, stored and prepared for use with the needle assembly 260 completely inside the enveloping shape of the pump 1. The enveloping shape may be an imaginary surface enveloping the housing of the pump 1 while smoothly bridging all gaps and recesses, should any be present, to define a closed shell. It is the shape of the pump 1 as perceived by the user from a distance and relevant when it comes to aspects of use like handling or wearability. Preparation of the patch pump in this embodiment includes filling the reservoir inside the reservoir unit 200 from the exterior using a transfer syringe and attaching the pump to the body of the patient using the adhesive patch assembly 280. An inserter assembly may be included in the reservoir unit 200 and configured to bring an output portion 260b of the needle assembly 260, such as the open distal end of the needle assembly 260, out of the enveloping shape of the pump and into the body of the patient once the pump is ready to start drug delivery. In implementations, the needle assembly 260 may include a rigid cannula and a soft cannula, and the inserter may be configured to insert the distal end of the soft cannula into the body of the patient using the rigid cannula, which may subsequently be retracted for drug delivery.

A rechargeable battery may provide the power for the drive mechanism and for system control circuitry. The latter may control the drive mechanism and may exchange data with an external controlling device, for example, via wireless data connection. Furthermore, the rechargeable battery may provide power for the inserter assembly in the reservoir unit 200.

FIG. 2b shows the semi-disposable patch pump from FIGS. 1a and 1b with the pump unit 100 and the reservoir unit 200 detached and separated, in a view from above, with the adhesive patch assembly 280 at the bottom towards the body of the patient, and the bayonet connection 212a in a disengaged state.

A first set of implementations illustrates the first aspect of the present disclosure. They are based on the wearable, semi-disposable patch pump shown in FIGS. 1a, 1b, 2a and 2b as described herein. They are further detailed in the following paragraphs.

The general aim of the present disclosure is to provide a semi-disposable patch pump, which may be optimized for ease of use, cost effectiveness and minimum waste. As provided from the general description of the embodiment of FIGS. 1a, 1b, 2a and 2b, the patient may have only two components to assemble: the reusable pump unit 100 with all the components intended for multiple or continuous use, and the disposable reservoir unit 200 with all the components intended for single use. FIG. 2b shows an implementation of the semi-disposable patch pump according to the present disclosure with the pump unit 100 and the reservoir unit 200 ready for application. The reservoir unit 200 is shown from outside with the reservoir unit housing 211 mounted on the adhesive patch assembly 280, and the mechanical interface to the pump unit, which may include the bayonet connection 212a shown on both units, the rotational axis 212b of the bayonet connection 212a shown on both units, and the locking structure 212d integrated in the reservoir unit housing 211. The locking mechanism 113 for the bayonet connection 212a may include the locking structure 212d on the reservoir unit and a flexible locking spring 113a on the pump unit (see FIG. 3b2). A base plate 211a may be integrated in the reservoir unit housing 211 and may form the bottom of the housing where the housing is attached to the adhesive patch assembly 280. The base plate 211a may be one unitary component or a combination of components that may be permanently connected together and attached to the adhesive patch assembly 280. The design of the bayonet connection 212a may include the definition of an opening side 114 of the pump, which may refer to the general direction or outer face where the pump unit can be lifted off the base plate to open the connection and remove the pump unit. In FIG. 2b the base plate is shown with a base plate extension 212c on the opening side 114. As the pump unit 100 is rotated around the rotational axis 212b of the bayonet, the base plate extension 212c may only cover an area on the opening side of the pump unit 100 starting from the rotational axis 212b of the bayonet connection 212a, because the base plate extension 212c may otherwise inhibit connecting the pump unit 100 to the reservoir unit 200.

Figure 16:
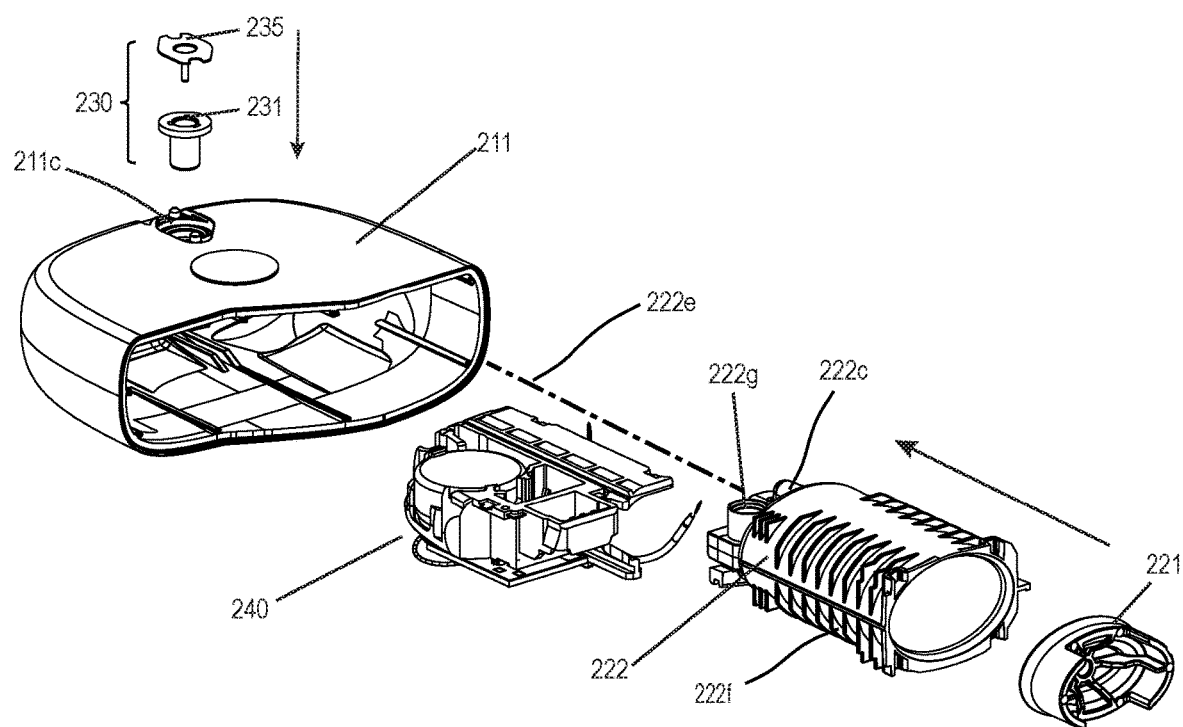
FIG. 16 depicts an exploded view of the reservoir unit showing the insertion of the cartridge and of the fill port assembly into the reservoir unit housing to form the reservoir unit.
Figure 18:
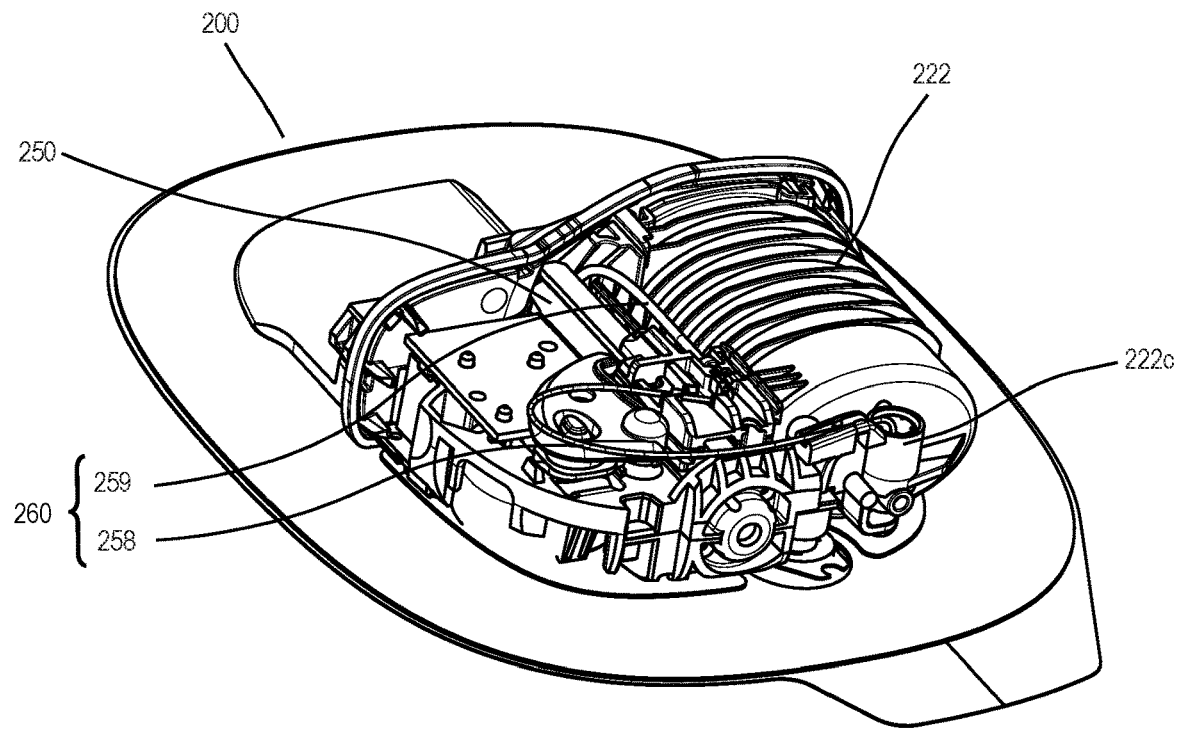
FIG. 18 depicts a perspective view of a reservoir unit with part of the housing removed.

An implementation of the reservoir unit 200 is illustrated in FIGS. 16 and 18, with selected parts removed to show the inner components thereof. In these figures, the reservoir 222 is shown with the plunger 221 and the reservoir outlet 222c leading to the needle assembly 260 mounted on an inserter assembly 250 which may provide an auto-inserting mechanism. In this implementation, the reservoir axis 222e along the axial center of the reservoir 222 and the plunger 221 may be arranged to coincide with the rotational axis 212b of the bayonet connection 212a (FIG. 2b) and be substantially orthogonal to the wall of the reservoir unit housing 211 facing the pump unit 100 in a fully assembled state.

Figure 17:
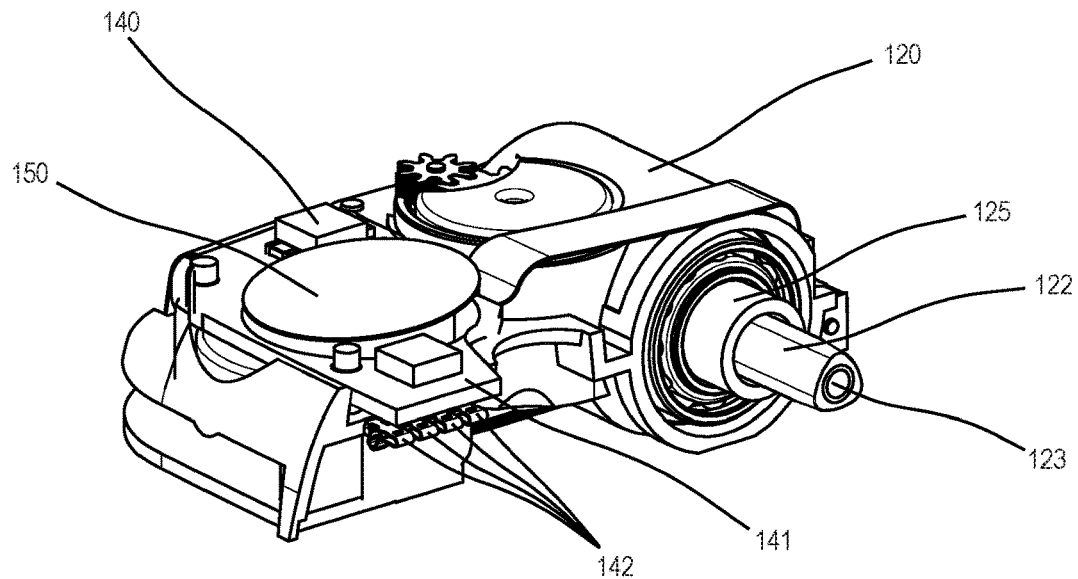
FIG. 17 depicts a perspective view of a pump unit with housing removed.

An implementation of the pump unit 100 is illustrated in FIGS. 2a-2b and FIG. 17, with selected parts removed to show the inner components. In these figures, the drive mechanism 120 is shown with the driving means provided as a threaded rod 125 mounted in and in cooperation with a plunger rod 122, with a rechargeable battery 150 and system control circuitry 140. The threaded rod 125 and the plunger rod 122 may be arranged in substantially the same direction as the rotational axis 212b of the bayonet connection 212a and substantially orthogonal to the wall of the pump unit housing facing the reservoir unit 200 in a fully assembled state.

Figure 3A:
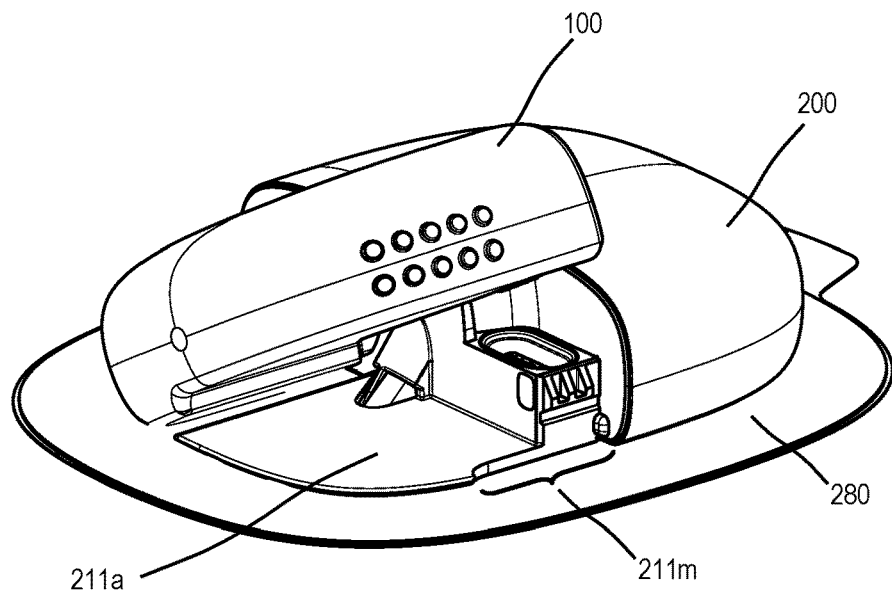

To apply the patch pump 1 and start drug delivery, the patient may take the reservoir unit 200 out of the packaging. If the reservoir is not pre-filled with drug, the patient may fill the drug into the reservoir 222. The pump unit 100 may already be activated from prior use. If not, the patient may need to perform additional steps such as unpacking, charging or programming to prepare the pump unit 100. External devices and/or system components may be used, such as a remote control unit with a wireless connection and software to interact with the user and set-up the communication with the pump unit 100. To attach the pump unit 100 to the reservoir unit 200, the user brings the portion of the bayonet 212a connector on the pump unit 100 in contact with the portion of the bayonet connector 212a on the reservoir unit 200 at an open angle, along the bayonet rotational axis 212b. Depending on the design of the bayonet construction, the open angle may be in the range of 5 degrees to 180 degrees, such as 15 degrees to 45 degrees. The user may push the two components along the rotational axis of the bayonet connection 212a together and fold the pump unit 100 down onto the plane of the base plate 211a. In implementations, the plunger rod cap 123 at the tip of the plunger rod 122 in the pump unit 100 may be connected to the opening behind the plunger 221 in the reservoir unit. With the bayonet components in place, the pump unit 100 may be folded down onto the plane of the base plate 211a of the reservoir unit 200 to close the connection. FIG. 3a shows this step with the pump unit 100 at the connecting angle of 30 degrees. The user may confirm the bayonet connection 212a is properly locked by pressing down the pump unit 100 onto the base plate 211a. By doing so, the flexible latch spring 113a (FIG. 3b2) of the reusable pump unit 100 engages with the locking structure 212d integrated in the reservoir unit housing 211 of the disposable reservoir unit 200, and locks the bayonet connection 212a in a closed position. This state is illustrated in FIGS. 3b1 and 3b2. The bayonet connection 212a of the present disclosure may also include any other locking mechanism such as a magnetic lock, Velcro®, latch or adhesive lock, provided the lock may be released without introducing an additional unlocking step.

In FIG. 4, the patch pump 1 is shown having been applied to the body of the patient 300 and may be ready for drug delivery. The enveloping surface 1a or outer shape or of the patch pump 1 is substantially edge-free and suitable for wearing with minimal risk of brushing the device off when sliding over an edge such as a door frame.

After successful delivery of the drug inside the reservoir 222, the patient may remove the pump unit 100 from his or her body. One single mechanical handling step may be used to remove the pump unit 100 from the used reservoir unit 200 and be ready for the new one. The bayonet connection 212a may be opened by lifting the pump unit 100 off the plane of the base plate 211a at the opening side 114 of the pump. The same movement may unlock the locking mechanism and open the bayonet. To further ease this handling step, a cut-out 211m may be made on the base plate 211a or the base plate extension 212c on the opening side 114 of the pump 1. The cut-out 211m may reduce the size of the base plate 211a at the location where the finger of the patient may grip the pump unit 100 for unlocking and detaching from the reservoir unit 200. The cut-out 211m may have an arbitrary shape, for example elongate, along the edge of the base plate 211a, about as long as the width of a finger and wide enough to generate a haptic effect. Accordingly, the size of the cut-out 211m along the base plate 211a and/or the base plate extension 212c may be 5 mm to 30 mm in length along the edge and 1 mm to 10 mm in width away from the original edge of the base plate 211a and/or base plate extension 212c. In FIG. 3a, an example of the cut-out 211m is shown at the edge of the base plate extension 211a. When folded up to the open angle of the bayonet connection 212a, the pump unit 100 may be separated from the reservoir unit 200 and attached to a new reservoir unit 200 to continue with the therapy.

According to a second aspect of the present disclosure based on the wearable, semi-disposable patch pump shown in FIGS. 1a, 1b, 2a and 2b, as described herein, is provided in the following paragraphs.

Figure 5:
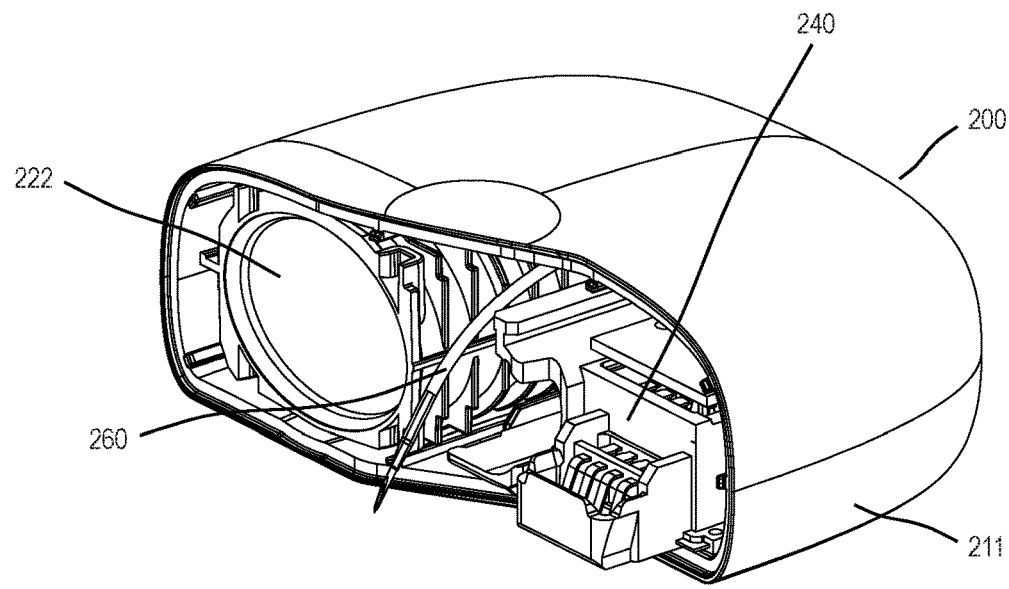
FIG. 5 depicts the reservoir unit of the patch pump without the front side of the housing and the adhesive release liner.
Figure 6A:
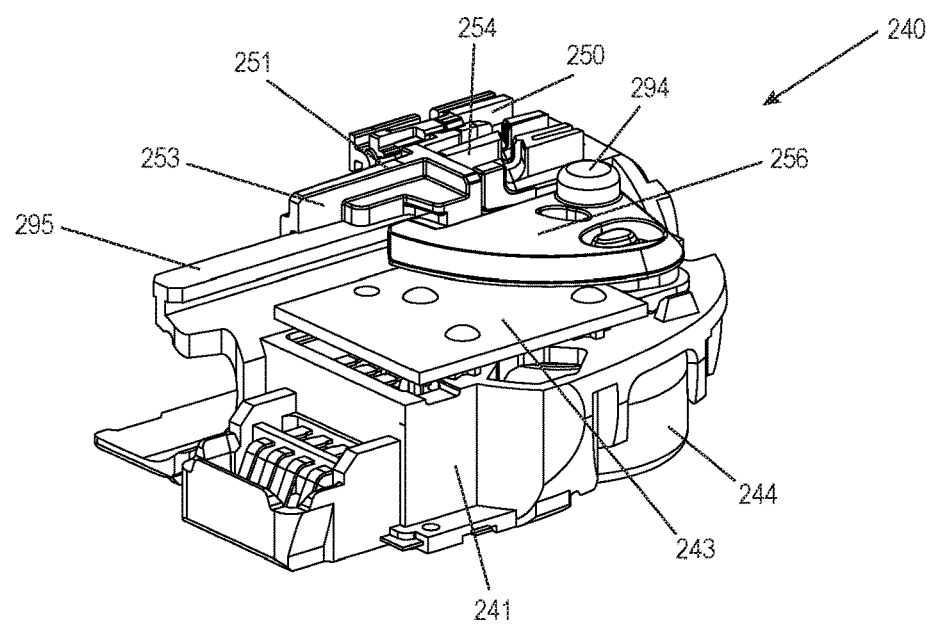
Figure 7:
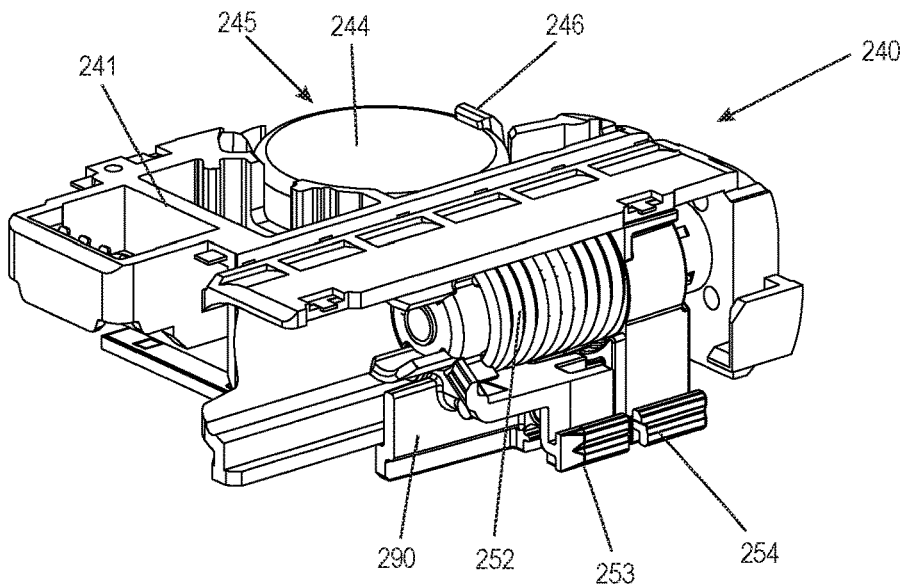
FIG. 7 depicts a bottom view of the hybrid assembly of FIGS. 6a and 6b.

FIGS. 5, 6a and 7 (a bottom view of the assembly of FIG. 6a) show the reservoir unit 200, with selected parts removed to allow a view inside the reservoir unit 200. The reservoir unit 200 includes a reservoir unit housing 211, a reservoir 222 with the medical substance, a hybrid assembly 240 according to the present disclosure, the button cell battery 244 and an adhesive patch (not shown) for connecting the patch pump 1 to the skin of the user.

Figure 6B:
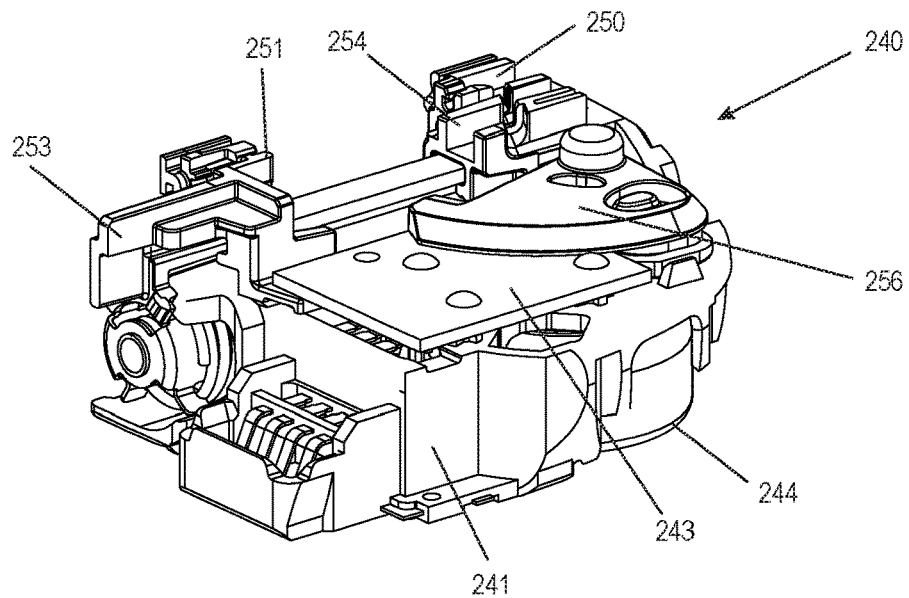

FIGS. 6a, 6b and 7 depict the hybrid assembly 240, which is arranged inside the reservoir unit housing 211 of the reservoir unit 200 as shown in FIG. 5. The hybrid assembly 240 may include parts of the inserter assembly 250, such as a cannula moving assembly 251. FIG. 6a depicts the hybrid assembly 240 with the cannula moving assembly 251 in a biased initial position. The inserter assembly 250 may bring the cannula moving assembly 251 from the biased initial position into an extended position for drug delivery. This movement may be driven for example by a system of elastic elements such as the insertion spring 252 (FIG. 7) built into the inserter assembly 250, with at least one of the elastic elements being pre-loaded during manufacturing of the patch pump. FIG. 6b depicts the hybrid assembly 240 with the cannula moving assembly 251 in an extended position for drug delivery. FIG. 7 shows a bottom view of the hybrid assembly 240.

As shown in FIG. 6a the hybrid assembly 240 includes a printed circuit board PCB-RU 243, the button cell battery 244 and a base frame 241 for supporting the hybrid assembly 240, the PCB-RU 243 and the battery 244.

In the following, the structural features of the base frame 241 are described in detail. Subsequently, the function of the hybrid assembly 240 is described.

Figure 8A:
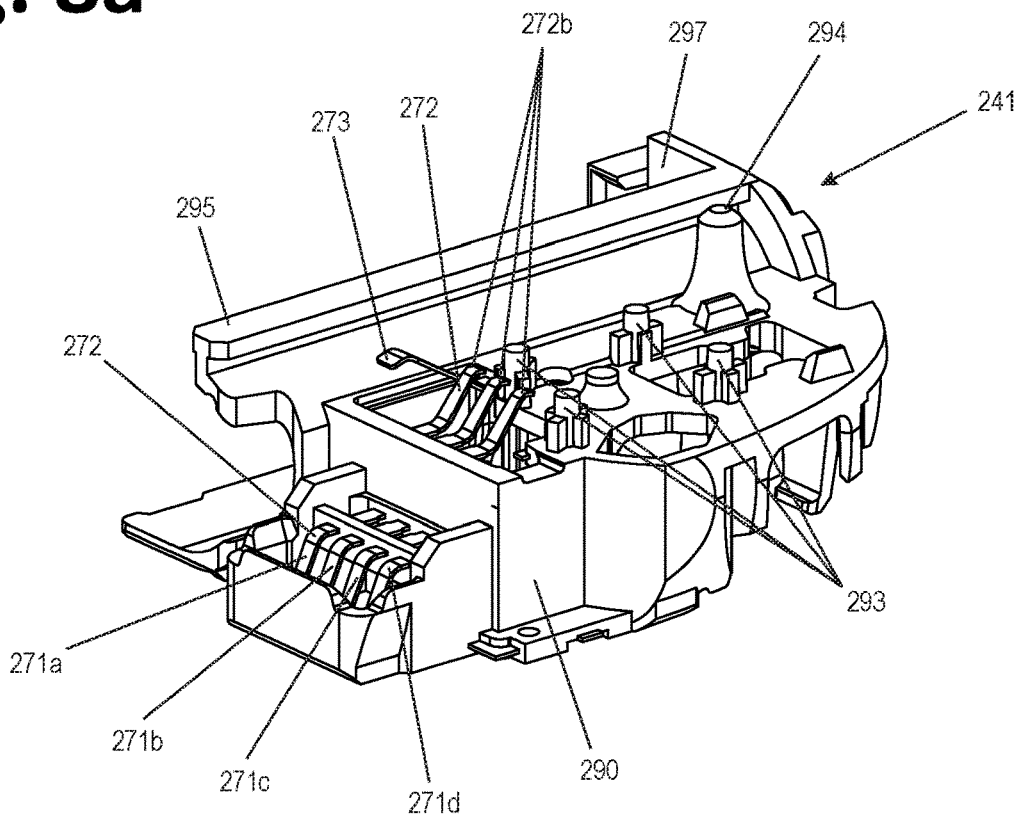

FIG. 8a depicts the base frame 241 alone. The base frame 241 includes a connector structure 270 with four connector members 271a-271d and a non-conductive body 290 made of plastic, which may be injection-molded around the connector structure 270.

In a first production step, the connector members 271a-271d may be stamped out of a metal sheet. At this stage, the connector members 271a-271d may be physically connected to each other by bridges, which may be or may be temporary connecting metal elements. In a second step, the connector members 271a-271d of the stamped out metal sheet may be bent to form electrical contact areas and arms. In a third step, the connector members 271a-271d may be overmolded by non-conductive plastic to form the non-conductive body 290 around the inlaid metal structure. In a fourth step, the bridges between the connector members 271a-271d may be eliminated by stamping to galvanically separate the connector members 271a-271d from each other. The connector members 271a-271d may be made of electroconductive metal. The injection-molded non-conductive body 290 may be made of a non-electroconductive plastic.

Figure 8B:
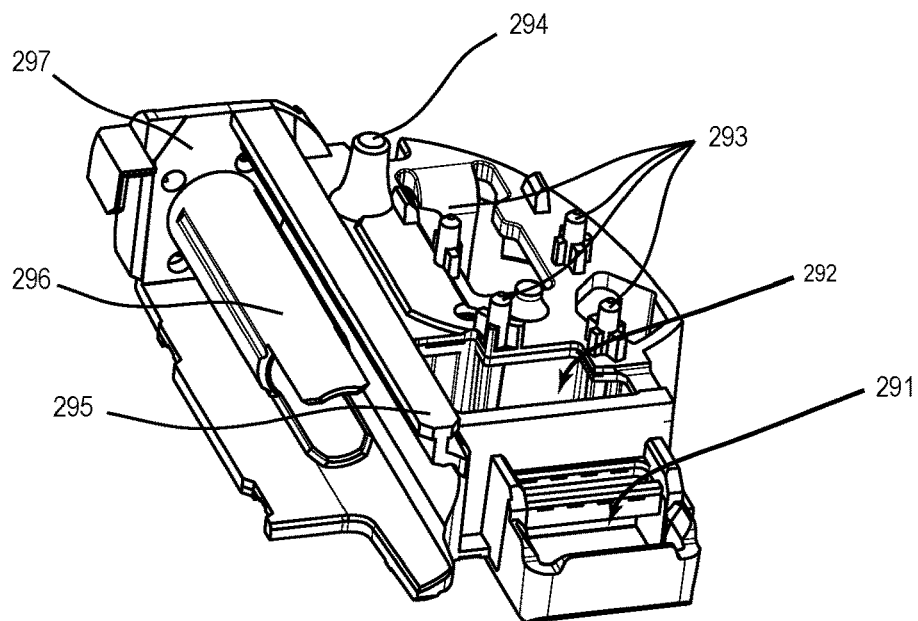
Figure 8C:
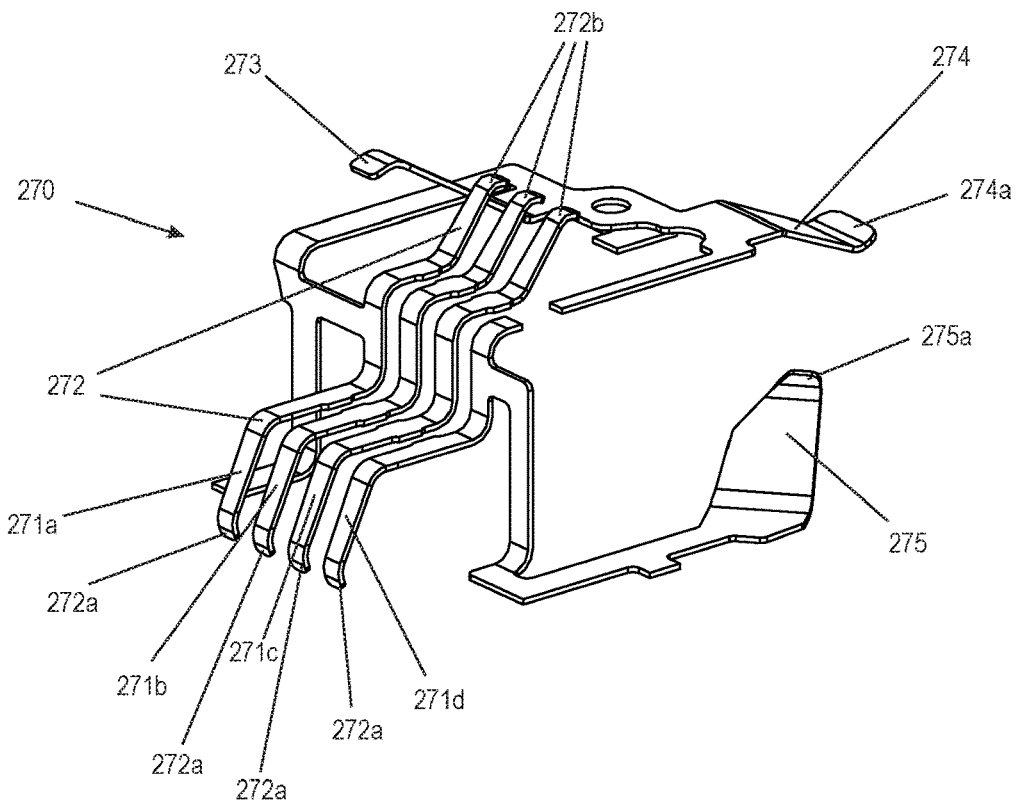

Each of the four connector members 271a-271d may include a contacting arm 272 (FIG. 8c). Each contacting arm 272 may include bendings. A first free end of the contacting arm 272 may form a first electrical contact area 272a as shown in FIG. 8c.

The first 271a, the second 271b and the third 271c connector member may each include a second end of the contacting arm 272 with a second electrical contact area 272b that may be adapted for electrically contacting the PCB-RU 243 supported by the non-conductive body 290 (see FIGS. 8a, 6a and 6b).

The first connector member 271a may additionally include a switching arm 273 and a first battery contact arm 274 shown in FIG. 8c. The switching arm 273 may be integrally formed in the first connector member 271a and may be resiliently held relative to the rest of the connector member. The switching arm 273 may include on its free end a contact surface adapted to establish an electrical contact to an electrical contact area of the pump unit printed circuit board PCB-PU 141 (see FIG. 17) when the pump unit 100 is connected to the reservoir unit 200. The first battery contact arm 274 may include on its free end a first battery contact area 274a adapted to be connected to the positive pole of the button cell battery 244.

The fourth connector member 271d may include only the first electrical contact area 272a and a second battery contact arm 275, which may include at its free end a second battery contact area 275a adapted to be connected to the negative pole of the button cell battery 244.

With reference to FIGS. 8a-8c the non-conductive body 290 is described in detail. The non-conductive body 290 may include a first opening 291 extending through the non-conductive body 290, through which opening the first electrical contact areas 272a of the contacting arms 272 may be contacted from outside the base frame 241. Through a second opening 292 in the middle of the non-conductive body 290, the second electrical contact areas 272b may be electrically connected to the reservoir unit printed circuit board (PCB-RU) 243. The switching arm 273 may also protrude through the second opening 292. On a bottom side of the non-conductive body 290 the first and second battery contact arms 274, 275 may reach out of the non-conductive body 290 such that the first and second battery contact arms 274, 275 contact the positive pole and the negative pole of the battery 244, respectively.

As depicted in FIG. 8a, the non-conductive body 290 may integrally form a linear guiding for the cannula moving assembly 251, where the cannula moving assembly 251 may include a soft cannula holder 253 and a rigid cannula holder 254 (see FIGS. 6a, 6b, 7). As depicted in FIGS. 8a-8c the linear guiding may include an upper guiding rail 295 and a lower guiding rail 296. The upper guiding rail 295 may be adapted to guide the soft and rigid cannula holders 253, 254, respectively, such that the holders 253, 254 may be shifted between the retracted position and an extended position, which is at a second end of the guiding rails 295, 296. The lower guiding rail 296 may be adapted to guide a retraction control part for retracting the rigid cannula holder 254 such that the control part may be linearly shifted along the lower guiding rail 296. At a first end of the guiding rails 295, 296, an end stop surface 297 may be arranged, which may restrict a linear movement of the soft and rigid cannula holders 253, 254 and define an initial or retracted position of the holders 253, 254.

On an upper side (shown in FIG. 8b), four fixing pins 293 may be integrated into the non-conductive body 290. During assembly the reservoir unit printed circuit board (RU-PCB) 243 may be mounted on the four fixing pins 293 and fixed by heat staking.

On a bottom side of the base frame 241 the non-conductive body 290 may form a battery opening 245 (shown in FIG. 7) adapted for accommodating the button cell battery 244. A retaining element 246 for holding the battery 244 may be arranged next to the battery opening 245. The retaining element 246 as depicted in FIG. 7 may be integrally formed in the non-conductive body 290. When a battery 244 is inserted into the battery opening 245 the retaining element 246 may be resiliently deflected to facilitate the insertion of the battery 244. If the insertion is completed and the battery 244 is placed into the battery opening 245, the retaining element 246 may resiliently move back and thus hold the battery 244 in the battery opening 245.

FIG. 8a shows the base frame 241 as a complete unitary component, FIG. 8b shows a view of the non-conductive body 290 without the inlaid connector structure 270 (e.g., conductive structure), and FIG. 8c shows a view of the connector structure 270 provided after manufacturing has been completed. As best visible in FIG. 8b, the non-conductive body 290 may further integrally form a cone-shaped bearing pin 294 on the upper side of the non-conductive body 290. The bearing pin 294 may be adapted to pivotally support an insertion trigger 256.

In the final assembled state, the complete hybrid assembly 240 may be placed inside the reservoir unit housing 211 of the reservoir unit 200 as shown in FIG. 5. If the pump unit 100 of the patch pump 1 is connected to the reservoir unit 200 by the bayonet connection 212a, connecting pins 142 (see FIG. 17) of the pump unit 100 may be pressed onto the first electrical contact area 272a of each of the contacting arms 272. Thereby, an electrical connection may be established between the battery 244 of the reservoir unit 200 and the system control circuitry 140 in the pump unit 100, and between the reservoir unit printed circuit board PCB-RU 243 and the system control circuitry 140 in the pump unit 100.

Through the electrical connection between the pump unit 100 and the reservoir unit 200 a rechargeable battery 150 in the pump unit 100 may be charged by the button cell battery 244 in the reservoir unit 200. By means of the electrical connection between the PCB-RU 243 and the PCB-PU 141 in the pump unit 100, the system control circuitry 140 may control a heating element of a heater assembly on the PCB-RU 243. In the same way, the system control circuitry 140 may control other elements on the PCB-RU 243 and/or obtain and process information about the status of the reservoir unit 200 such as the position of the needle assembly 260.

If the control circuitry 140 of the pump unit 100 sends a release command to the PCB-RU 243 in the reservoir unit 200, a heating element of the heater assembly may be activated. The heating element may then heat up a fuse to cause the fuse to melt, to extend or to break. This may trigger the release of the biased insertion trigger 256, which may be pivotally supported by the bearing pin 294 (see FIGS. 6a and 6b). After the biased insertion trigger 256 is released, it may rotate away from the soft and rigid cannula holders 253, 254 and thus release them. After the release, the holders 253, 254 may move to the extended position, driven by a spring 252 guided by the guiding rails 295, 296 and may thereby insert a soft and hard cannula into the skin of the user. The insertion mechanism is described in detail in the European Patent Application EP 18199475.7 which is hereby incorporated in its entirety.

A third aspect of the present disclosure based on the wearable, semi-disposable patch pump shown in FIGS. 1a, 1b, 2a and 2b is provided as follows.

Figure 9A:
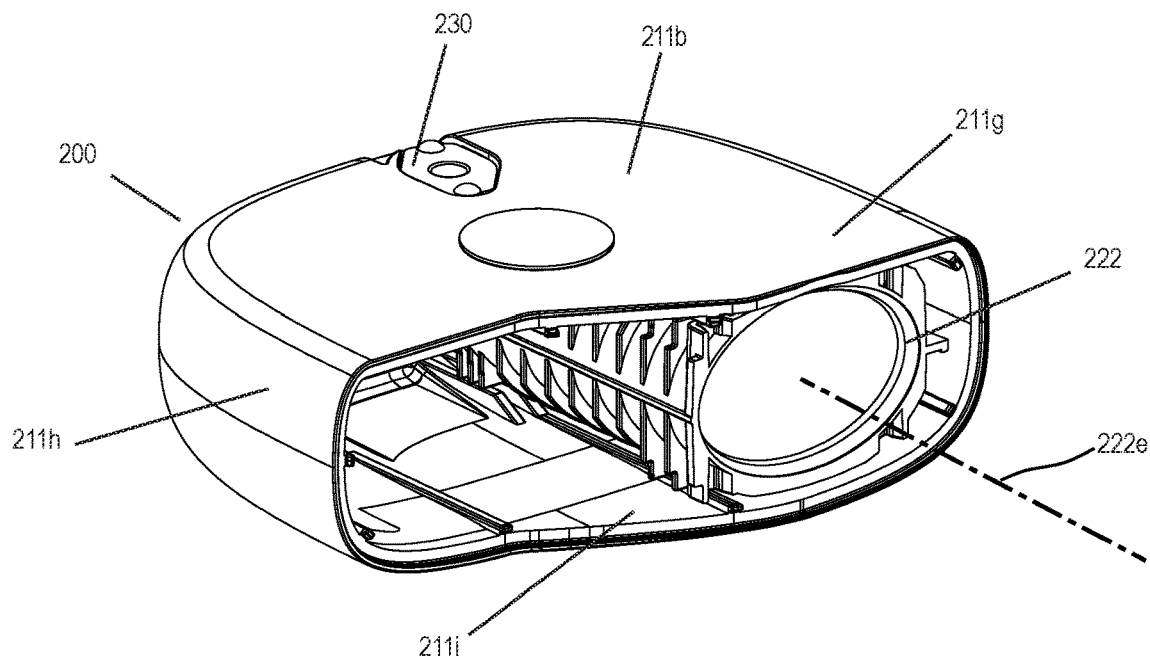
Figure 10A:
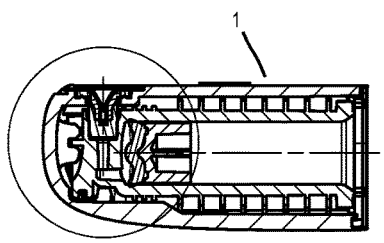
FIG. 10a depicts the cross section of a reservoir unit from FIGS. 9a, 9b1 and 9b2 as seen before fixation of the fill port by heat staking.
Figure 10A:
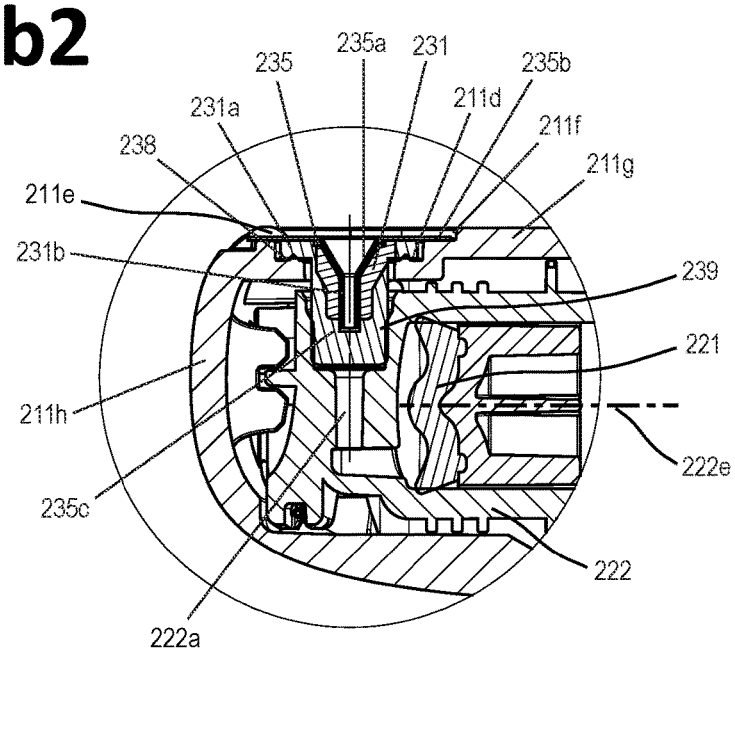
Figure 10A:
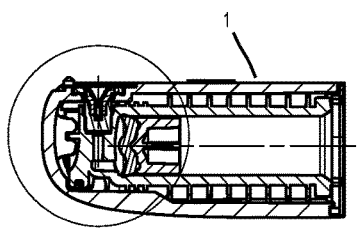
Figure 10B:
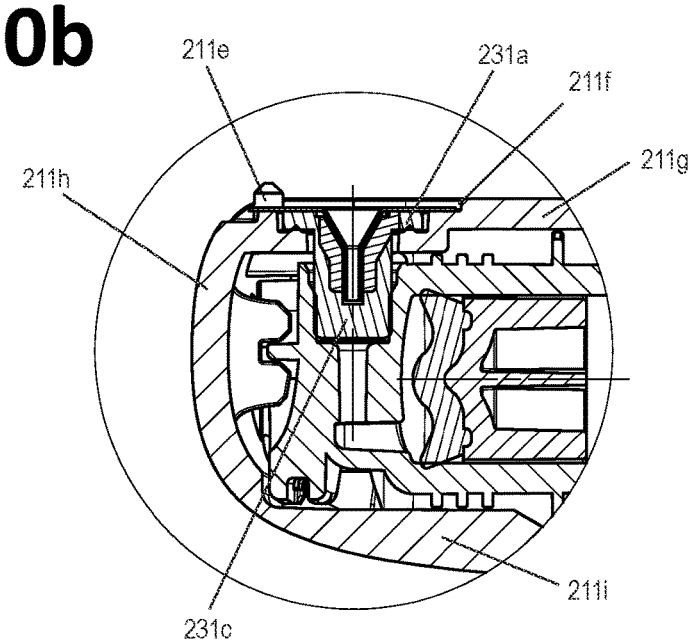
Figure 11A:
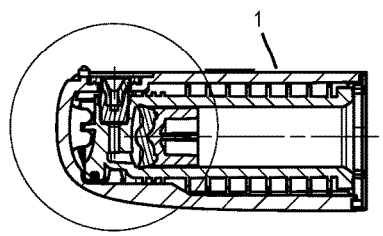
FIG. 11a depicts a cross section of the reservoir unit from FIGS. 9a, 9b1 and 9b2 with inserted fill port sealing, without the insert.
Figure 11B:
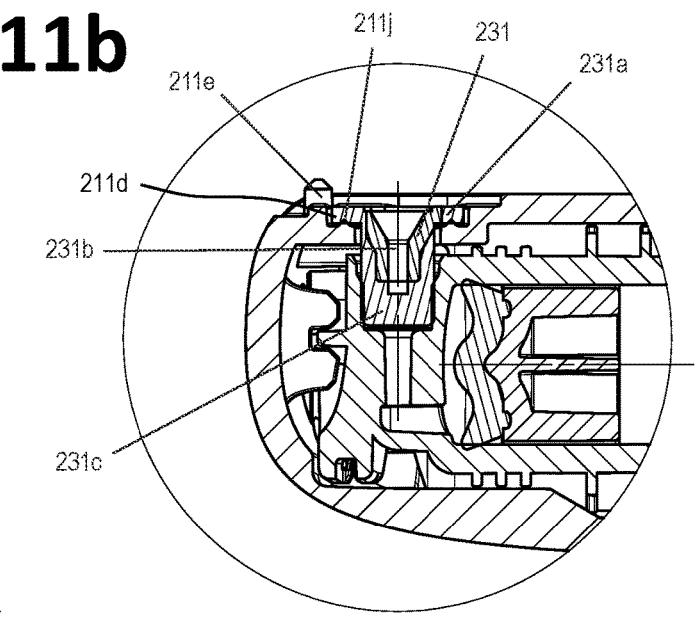
Figure 12A:
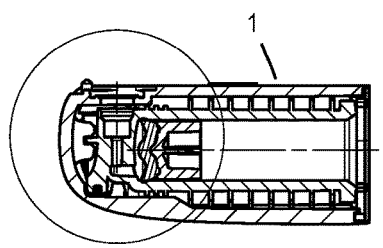
FIG. 12a depicts a cross section of the reservoir unit from FIGS. 9a, 9b1 and 9b2 before mounting the fill port assembly.
Figure 12B:
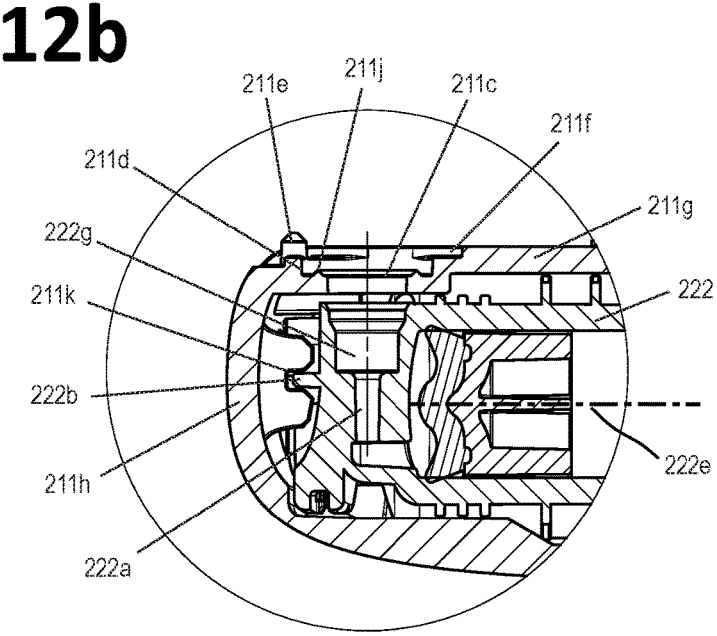

FIG. 9a shows a bottom isometric view of the reservoir unit 200 including a reservoir or cartridge 222 and a fill port assembly 230, where the fill port may be arranged. The reservoir unit 200 may include a housing 211 formed by a bottom wall 211g, a side wall 211h and a top wall 211i. The walls of the housing 211 may define an interior space having an opening for, amongst other things, receiving the reservoir 222. The fill port assembly 230 may be arranged in the bottom wall 211g but may also be arranged in the other wall sections. The fill port assembly 230 may be used for filling an empty reservoir 222, which may be closed by a plunger 221, see FIG. 9b2. Details of the fill port assembly 230, the housing 211 and the reservoir 222 are presented in cross sectional views for:

an assembled and fixed fill port assembly 230 in FIG. 9b2,
an assembled but not yet fixed fill port assembly 230 in FIG. 10b,
a partially assembled fill port assembly 230 without an insert 235 in FIG. 11b, and
the assembly of the housing 211 and the reservoir 222 in FIGS. 12a and 12b.

As best visible in the exploded view of FIG. 16 and in the cross-section view of FIG. 12b, the housing 211, such as bottom wall 211g may include a passage 211c adapted to receive the fill port assembly 230 formed by an insert 235 and fill port sealing 231. The passage 211c in the wall of the housing may be surrounded by recesses or recessed sections (211d, 211f) and the passage 211c may be aligned with the inlet 222a of the reservoir 222 to form an opening for receiving the fill port assembly 230. The housing 211, such as the bottom wall of the housing 211g may include at least one fixing pin 211e that may be made from the same thermoplastic polymer as the housing 211.

To properly position and fix the reservoir 222 inside the housing 211 of the drug delivery device, a stabilizing protrusion 222b (FIG. 12b) may be integrated in the reservoir 222. When the reservoir 222 is inserted into the housing 211 of the drug delivery device, the stabilizing protrusion 222b may slide into a recess in the inner wall of the housing, in FIG. 12b shown as stabilizing recess 211k. With the stabilizing protrusion 222b is positioned in the stabilizing recess 211k, the reservoir 222 may be properly positioned and laterally fixed to allow lateral pressure for mounting the fill port assembly 230. Further, the interaction between the stabilizing protrusion 222b and the stabilizing recess 211k may be designed as a snap fit connector (not shown in FIGS. 12a, 12b and 16).

Once the reservoir 222 has been inserted and guided into the housing 211, for instance until the reservoir 222 abuts a stop in the housing 211, the inlet 222a (FIG. 12b) of the reservoir may be aligned with the passage 211c in the housing 211. The stop in the housing 211 may be formed by a protrusion or protruding structure on the housing abutting a portion of the reservoir.

Figure 13:
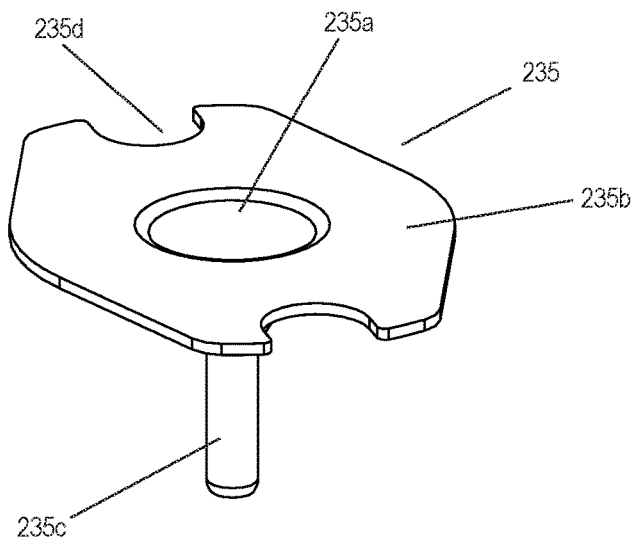
FIG. 13 depicts a perspective view of the insert.
Figure 14A:
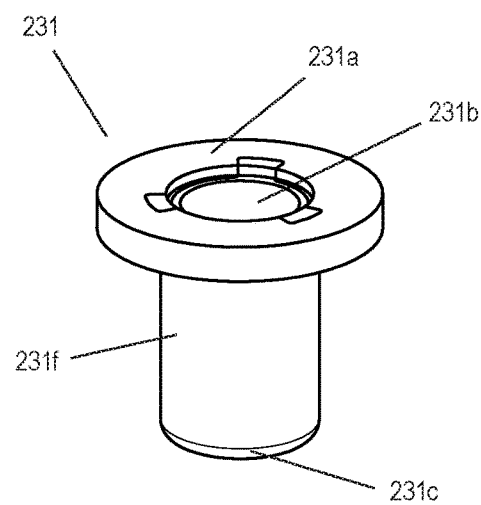
FIG. 14a depicts the fill port sealing in a perspective view.
Figure 14B:
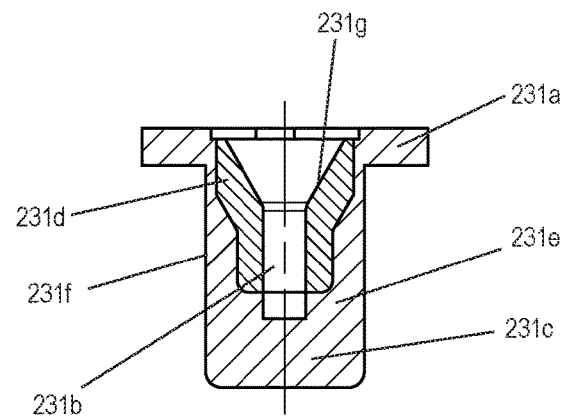
FIG. 14b depicts the fill port sealing of FIG. 14a in a cross-section view.
Figure 15:
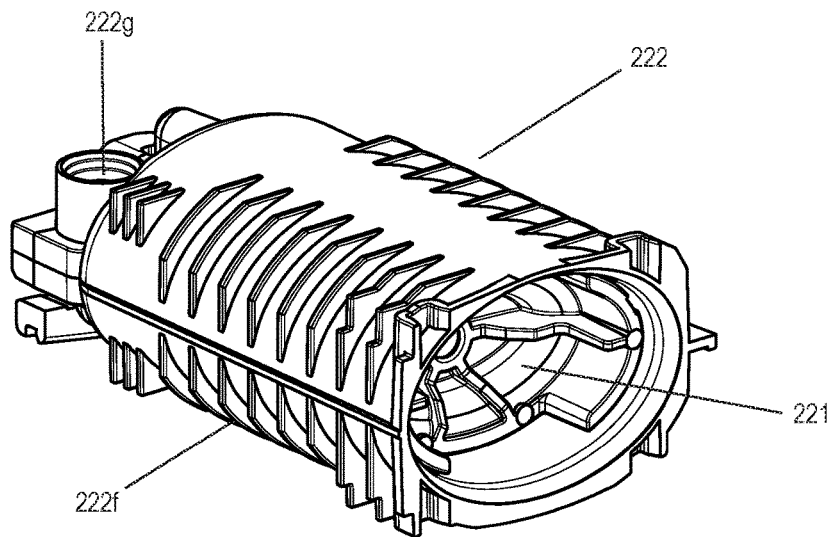
FIG. 15 depicts a perspective view of a reservoir including plunger.

To establish a fluid path from the exterior to the reservoir inlet 222a and ensure fluid-tightness (e.g., a sealing fluid connection) at a specified pressure such as the filling pressure, the fill port assembly 230 may include at least one sealing. In the embodiment shown in FIG. 16, a fill port sealing 231 may be inserted into the passage 211c of the housing 211 along a longitudinal axis formed by the inlet 222a of the reservoir and along a corresponding axis of the passage 211c of the housing 211. The longitudinal axis of the inlet 222a may be perpendicular to the longitudinal axis 222e of the reservoir 222. The fill port sealing 231 may include a cylindrical section 231f connecting a flange 231a to a pierceable septum 231c (FIGS. 14a and 14b). The axis of the cylindrical section 231f may be aligned with the axis of the inlet 222a of the reservoir when the fill port sealing 231 has been inserted into the passage 211c. The flange 231a of the fill port sealing 231 may have a lateral dimension that tightly fits into the second recessed section 211d (FIG. 11b) of the housing 211, whereas the pierceable septum 231c may tightly fit into the inlet 222a (FIG. 12b) of the reservoir. The flange 231a may be disc shaped having a cone shaped opening 231g for accessing a bore 231b ending in the pierceable septum 231c. The flange 231a may fit in a disc shaped second recessed section 211d in the housing 211. The cylindrical section 231f may form the bore 231b and may be adapted to receive a sleeve 235c of the insert 235 (see FIG. 13). The entrance of the fill port sealing 231 starting from the flange may be cone shaped and may be adapted to receive a cone shaped opening 235a of the insert 235 (FIG. 13). The longitudinal axis of the cone of the insert 235 may coincide with the longitudinal axis of the inlet of the reservoir 222. The fill port sealing 231 may be made, in this example, both from an elastomer and a thermoplastic polymer. Alternatively, only an elastomer may be used. The flange 231a and the outside surface of the cylindrical section 231f may be made from the elastomer such that the flange 231a may form a sealing towards the housing 211 and the distal end of the cylindrical section 231f may form a sealing with the inlet 222a of the reservoir 222. The cone section of the fill port sealing 231 may be made from the thermoplastic polymer to provide mechanical strength to the fill port sealing 231. The fill port sealing 231 is shown as a unitary component in FIGS. 14a and 14b. The fill port sealing 231 may be inserted into the fill port sealing cavity 222g of the reservoir 222 shown in FIG. 15. The fill port sealing 231 may be made using 2-component injection molding with a rigid thermoplastic 231d such as PBT and a soft elastomer 231e such as polysiloxane liquid silicone (LSR) rubber.

A cross-section view of the fill port sealing 231 that has been inserted into the passage 211c in the bottom wall 211g of the housing is shown in FIGS. 11a and 11b. The distal surface of the flange 231a contacts the proximal surface of the second recessed section 211d of the housing 211 (see FIG. 12b). Optionally, the housing 211 may include a protruding rim 211j contacting the flange 231a of the fill port sealing 231. The distal end of the cylindrical section 231f of the fill port sealing 231 (FIGS. 14a and 14b) may have an outer dimension that is greater than the inner dimension of the inlet 222a of the reservoir 222 (FIG. 12b) such that the distal end of the cylindrical section 231f is radially compressed as it enters the reservoir 222 thus establishing a second sealing 239 between the fill port sealing 231 and the inlet 222a of the reservoir (FIG. 9b2). The second sealing 239 may be radially oriented perpendicular to the axis of the inlet 222a of the reservoir 222. Optionally, the distal end of the cylindrical section 231f and/or the pierceable septum 231c may form an axial sealing with a surface of the inlet 222a of the reservoir 222.

The exploded view of FIG. 16 shows how the fill port sealing 231 and the insert 235 may be inserted into the passage 211c of the housing 211. FIGS. 10a and 10b show a cross-section view of the fill port assembly 230 in this inserted state, before fixation. The insert 235 may be made from a metal (e.g., stainless Cr—Ni steel, for example AISI 305) and may include a cone shaped opening 235a connecting a base 235b to a sleeve 235c (see also FIG. 13). The cone shaped opening 235a may fit into the cone of the fill port sealing 231 formed by the thermoplastic polymer 231d. The sleeve 235c may fit into the bore 231b of the sealing for guiding a needle towards the pierceable septum 231c. The base 235b of the insert may include cut-outs or openings 235d which may be adapted to be received by the at least one fixing pin 211e extending from the housing 211 and the outer dimensions of the base 235b as such may fit into the first recessed section 211f of the housing 211 (FIG. 10b). The insert 235 may be fixed to the housing 211 by heat staking of the fixing pin 211e, for instance by heating and deforming the fixing pin 211e (FIG. 9b2). During fixing of the insert 235, the flange 231a of the fill port sealing 231 may be axially compressed between the base 235b of the insert 235 and the bottom wall 211g of the housing 211. Optionally, the flange 231a may be locally compressed by the protruding rim 211j present in the second recessed section 211d in the housing 211 (FIGS. 11a and 11b). Due to the compression of the flange 231a, as shown in FIG. 9b2, a first sealing 238 may be formed that is axially displaced from the second sealing 239. The first and second sealings 238, 239 may be established by the fill port sealing 231 and bridge a gap between the inlet 222a of the reservoir 222 and the housing 211 and prevent leakage from the reservoir 222 into the housing 211 and into the exterior (FIG. 9b2). Moreover, the first and second sealings 238, 239 may prevent contamination from the exterior into the drug delivery device or into the reservoir 222.

As the insert 235 is fixed to the housing 211, also lateral movement of the reservoir 222 with respect to the housing 211 may be limited or even act as an impact absorber for the reservoir 222. The inlet 222a of the reservoir 222 may be coupled to the housing 211 via the fill port sealing 231 and the insert 235 and the elastomeric material of the fill port sealing 231 may act as a cushion or provide shock absorption between the rigid reservoir and rigid housing.

A method for assembling the drug delivery device or a part of the drug delivery device is shown in FIG. 16. The reservoir 222 may be inserted into the opening of the housing 211 along the longitudinal axis 222e of the reservoir 222. The plunger 221 may already be present in the reservoir 222 (FIG. 9b2) or may be inserted into the reservoir 222 after the reservoir 222 is positioned inside the housing 211. The wall of the reservoir 222 may be reinforced with a number of reinforcing ribs 222f which may be adapted to facilitate the orientation and guidance of the reservoir 222 in the housing 211 during assembly. The housing 211 of the drug delivery device may further have a stop surface which, when abutted by the reservoir 222, may ensure that the inlet 222a of the reservoir 222 is aligned with the passage 211c of the housing 211. The inside surface of the housing 211 may have longitudinal ridges for correctly guiding the reservoir 222 to its final position. In a subsequent step, the fill port sealing 231 and the insert 235 may be inserted into the passage 211c in the housing 211 along an axis that is defined by the cone shaped opening 235a of the insert 235

(or the cone shaped opening of the fill port sealing 231). The axis defined by the cone shaped opening 235a may be identical to the axis defined by the inlet 222a of the reservoir 222 when the reservoir 222 is in its final position. The distal end of the fill port sealing 231 may enter the inlet 222a of the reservoir 222 to establish the second sealing 239 during insertion of the fill port sealing 231. During fixation of the insert, for instance by heat staking of the fixing pins 211e, the first sealing 238 may be established. Before, during or after insertion of the reservoir 222, the hybrid assembly 240 may be inserted into the housing 211 as well.

A fourth aspect of the present disclosure based on the wearable, semi-disposable patch pump shown in FIGS. 1a, 1b, 2a and 2b is provided as follows.

Figure 19:
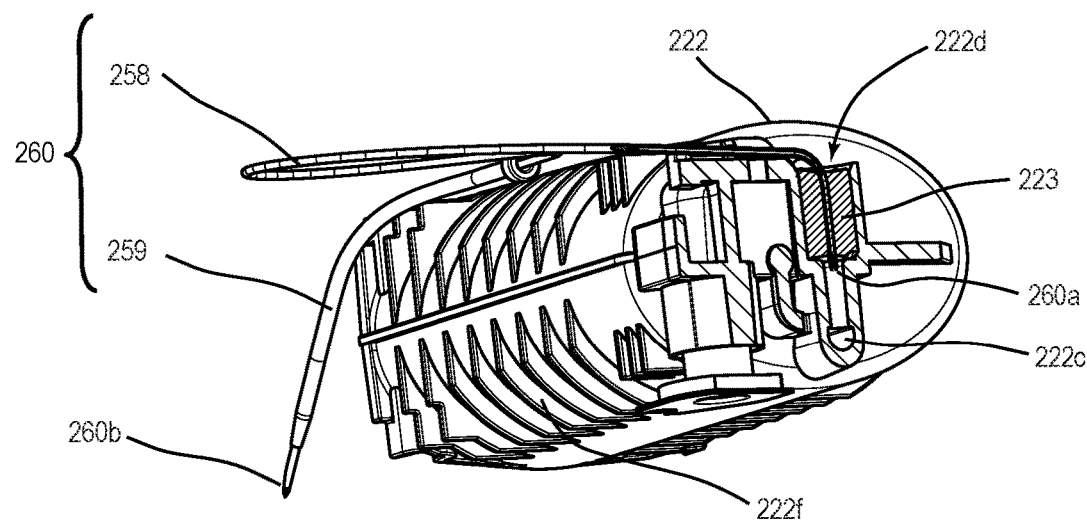
FIG. 19 depicts a patch pump with a reservoir outlet seal, and a cross-section of the reservoir outlet.

The reservoir outlet sealing may be improved by a design which may be cost-effective for manufacturing. Aspects of this design have already been described with respect to the third aspect of the present disclosure, where the reservoir outlet sealing is combined with an improved fill port. FIG. 18 shows an additional way to improve the reservoir outlet sealing. The reservoir unit 200 of FIGS. 1a and 1b is shown with part of the housing 211 removed, followed by a more detailed cross-section view of the outlet of the reservoir 222 (FIG. 19). The reservoir 222 may have a rigid structure forming a reservoir outlet 222c. In this example, the reservoir outlet 222c may have a substantially cylindrical reservoir outlet sealing cavity 222d. During manufacturing, the reservoir outlet sealing cavity 222d may be closed by inserting a substantially cylindrical reservoir outlet sealing 223 made of soft, fluid-tight but pierceable material such as silicone or any kind of rubber, which may establish a fluid-tight closure of the reservoir outlet sealing cavity 222d. In a separate manufacturing step, the reservoir outlet sealing 223 may be pierced by the input portion 260a of the needle assembly 260. In the implementation shown, the input portion 260a of the needle assembly 260 may include or consist of the input portion of the rigid cannula 258. The result may be a fluid-tight connection between the outlet of the reservoir 222 and the needle assembly 260. Unlike with a membrane-like sealing, the substantially cylindrical shape of the reservoir outlet sealing 223 and consequently of the reservoir outlet sealing cavity 222d may provide for improved fluid-tightness, such as up to a specified filling pressure of 6 to 8 bar. A large range of variations of this embodiment may be possible and be within the scope of the present disclosure. The reservoir outlet sealing cavity 222d and the reservoir outlet sealing 223 may only be partially cylindrical or have a different shape altogether, while keeping the area of contact between the reservoir outlet sealing cavity 222d and the reservoir outlet sealing 223 large enough to provide the required fluid-tightness. Manufacturing of the reservoir outlet 222c may vary by changing the sequence of manufacturing steps, for example, by piercing the reservoir outlet sealing 223 before or after inserting the reservoir outlet sealing 223 into the reservoir outlet sealing cavity 222d. More variations may be generated by applying the improvements to the exit port sealing to the reservoir outlet 222c. Features described in the fourth aspect of the present disclosure may reduce the number of components by applying 2-shot injection molding technology or improving manufacturability by introducing an exit port sealing plug cavity, which may intersect the outlet port opening, and may also lead to variations of the embodiments as described for the reservoir outlet 222c.

A fifth aspect of the present disclosure based on the wearable, semi-disposable patch pump shown in FIGS. 1a, 1b, 2a and 2b is provided as follows.

Figure 20:
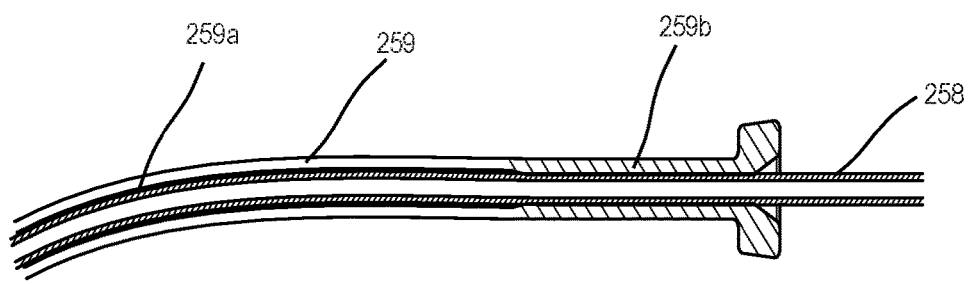
FIG. 20 depicts a cross-section detail of a patch pump with a soft cannula input sealing.

In FIG. 18, the reservoir unit 200 of FIGS. 1a and 1b is shown with a portion of the housing 211 removed and shows the rigid cannula 258 and the soft cannula 259 which may be the main components of the needle assembly 260 in this implementation. FIG. 20 shows a cross-section view of the needle assembly 260 at the interface between the rigid cannula 258 and the soft cannula 259. The rigid cannula 258 may have a substantially tubular shape and may be configured to slide axially in a soft cannula lumen 259a of the soft cannula 259, while maintaining a fluid-tight sealing connection at a proximal input end of the soft cannula 259. To achieve fluid-tightness up to the specified filling pressure of 6 to 8 bar, the soft cannula 259 may include a soft cannula input sealing portion 259b, where the material of the soft cannula 259 may be deformed, thickened or otherwise altered to increase the pressing of the soft cannula 259 on the surface of the rigid cannula 258. The cannula input sealing portion 259b of the soft cannula 259 may be formed during manufacturing of the needle assembly 260 or at a later manufacturing step of the pump by injection molding, by applying heat and/or mechanical pressure from outside the needle assembly 260, or by other means to thicken and/or deform the soft cannula 259. While the location of the cannula input sealing portion 259b may be at the proximal input of the soft cannula 259, the soft cannula input sealing portion 259b may be positioned further towards the output end of the soft cannula 259, for example. Further variations may involve the soft cannula input sealing portion 259b being a separate component from the soft cannula 259.

A sixth aspect of the present disclosure based on the wearable, semi-disposable patch pump shown in FIGS. 1a, 1b, 2a and 2b is provided as follows.

Figure 21A:
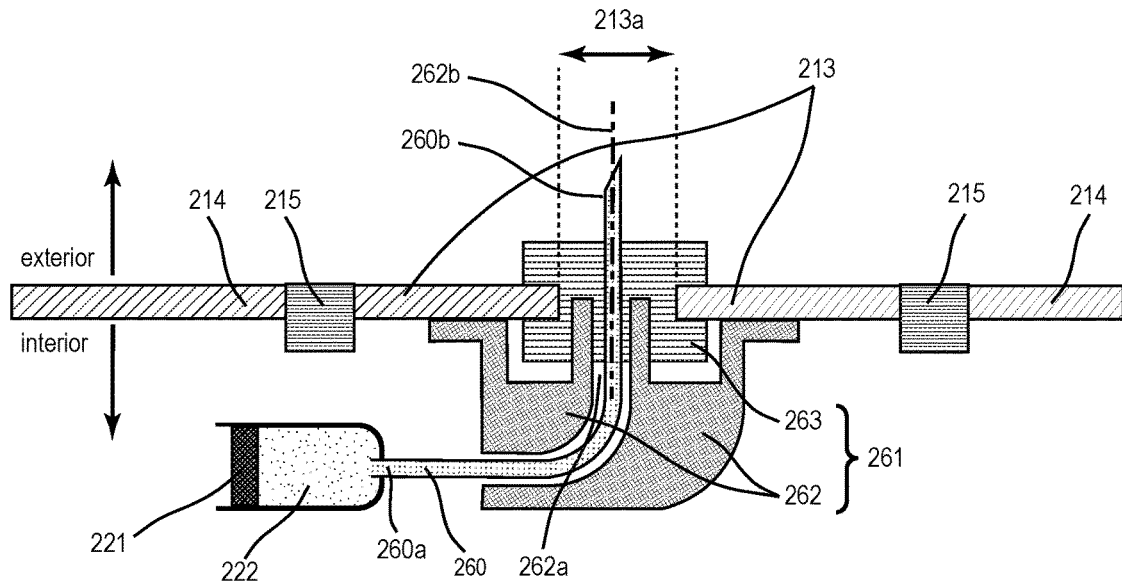

The exit port may be improved by reducing the number of components at this interface by integrating one or more originally separate components into one unitary component. FIG. 21a provides a schematic overview of this aspect at the exit port of the drug delivery device. The housing of the pump is shown with a first housing component 213 around the exit port opening 213a and two other housing components 214 connected to the first housing component 213 via housing sealings 215. The combination of housing components, both of the pump unit and the reservoir unit 200, when equipped with a fill port and/or an exit port and/or other sealing elements suitable for the intended use and connected for said intended use, may form a protective shell to protect the pump from mechanical damage, contamination or other form of environmental ingress. An exit port assembly 261 may include a rigid exit port sealing holder 262 and a soft exit port sealing 263 and may be mounted at the exit port opening 213a of the housing. To support the manufacturing process of the patch pump, the rigid exit port sealing holder 262 may not only hold the soft exit port sealing 263 in place for closing the exit port opening 213a, but may also serve as a mechanical guide for the process of piercing the soft exit port sealing 263 with the output portion 260b of the needle assembly 260. The rigid exit port sealing holder 262 may have any shape suitable for that purpose. Examples of such shapes may include a straight tube, a bent tube, a cone, a U-shaped groove or a combination of these shapes. At the point of piercing, where the output portion 260b of the needle assembly 260 first comes into contact with the soft exit port sealing 263, the shape of the rigid exit port sealing holder 262 may be tubular, which may define an at least partially tubular exit port channel 262a with an axis 262b.

The rigid exit port sealing holder 262 may be attached to one of the housing components, for example shown in FIG. 21a, to the first housing component 213. The soft exit port sealing 263 may be mounted at the exit port opening 213a to fluid-tightly close or seal the exit port opening 213a, while at the same time establishing a fluid-tight sealing between the rigid exit port sealing holder 262 and the housing, e.g., the first housing component 213 in FIG. 21a. This may have the advantage that the connection between any housing component and rigid exit port sealing holder 262 may not need to be fluid-tight at all. The requirement for fluid-tightness of the exit port may be fully ensured by the soft exit port sealing 263, which may be designed to withstand the pressure as specified, be it environmental pressure, occlusion pressure or filling pressure. The soft exit port sealing 263 may be made of a soft and elastic material, such as an elastomer like silicone rubber or any other fluid-tight material which may be pierceable by the output portion 260b of the needle assembly 260 and elastic enough to provide the surface pressure required for fluid-tight sealing at the specified fluid pressure. Other examples for such an elastomer may by an EPDM rubber, PDMS rubber, such as in LSR form or an elastomeric polyurethane (PUR) or a thermoplastic elastomer (TPE). The soft exit port sealing 263 may be attached to the rigid exit port sealing holder 262 during manufacturing to form a fluid-tight connection, for example by a 2-shot injection molding, by press-fit or by any other means of fixating the sealing for the intended use. The process of manufacturing the patch pump of this implementation may include the step of attaching the rigid exit port sealing holder 262 to the housing, while thereby closing the exit port opening 213a, and the step of piercing the soft exit port sealing 263 by the output portion 260b of the needle assembly 260. As the output portion 260b of the needle assembly 260 may be inserted into the body of the patient for drug delivery, said output portion 260b may have a rigid and pointed end, such as the tip of a sharpened needle or rigid cannula, e.g., rigid cannula 258. The sequence of manufacturing steps may not be relevant for the function of the exit port, hence the piercing of the exit port sealing 263 may take place before or after mounting the exit port assembly 261 into the housing of the drug delivery device. As the soft exit port sealing 263 has two sealing functions, the step of attaching the rigid exit port sealing holder 262 to the housing may be the same as the step of attaching the soft exit port sealing 263 to the rigid exit port sealing holder 262.

The result may be a patch pump which is easy to manufacture and has a unitary exit port sealing that may fulfill three sealing functions in one: sealing the housing to the rigid exit port sealing holder 262, sealing the output portion 260b of the needle assembly 260 to the rigid exit port sealing holder 262, and fluid-tightly closing the exit port opening 213a.

Figure 21B:
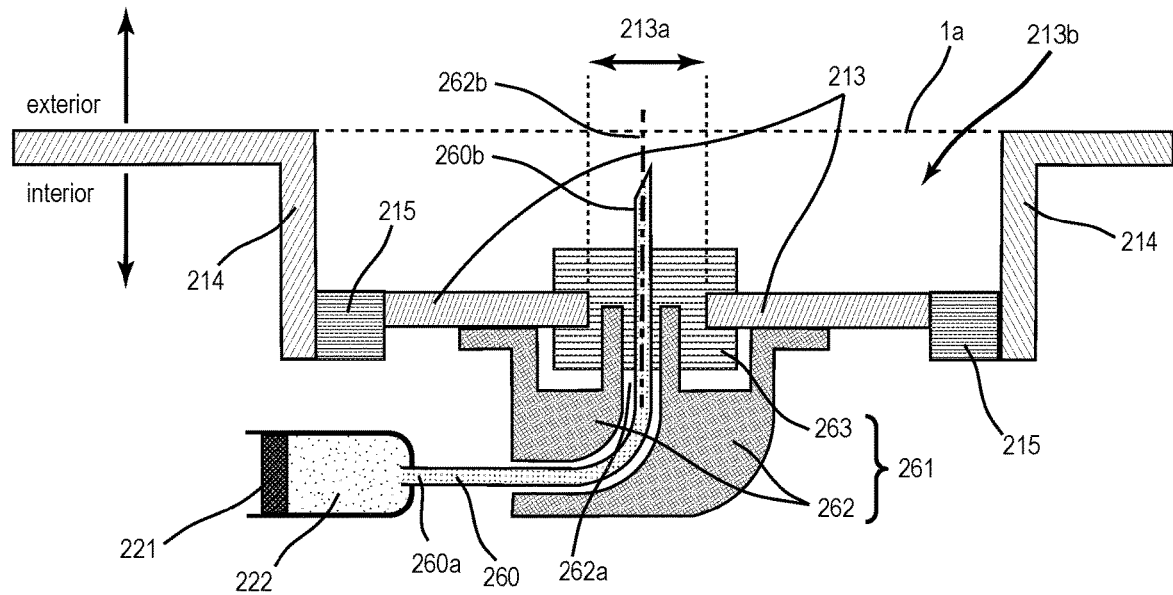

A further improvement of the exit port of the present disclosure may be implemented by modifying the shape of the housing of the drug delivery device and by introducing a recess in the area of the exit port. This alternative is shown in the schematic overview of FIG. 21b using the same numerals for the same parts as in FIG. 21a. The recess in the housing may create an exit port chamber 213b and the exit port opening 213a may now lie sufficiently far in the interior of the enveloping surface 1a of the pump to keep the output portion 260b of the needle assembly 260 completely or substantially in the interior. This arrangement may provide the advantage of protecting the output portion 260b of the needle assembly 260 from inadvertent physical contact with the external environment, contamination or damage, while at the same time protecting the user and/or patient from inadvertent contact with the output portion 260b of the needle assembly 260 and hence reducing the risk of harm by pricking or needle sticks.

The exit port implementation of the present disclosure may lead to at least three main groups of further improved implementations. In a first group, the exit port may be improved by combining the components of the exit port assembly 261, the rigid exit port sealing holder 262 and the soft exit port sealing 263 into one unitary component. FIGS. 22a1, 22a2 and 22b illustrate an implementation of this group. FIG. 22a1 shows the exit port assembly 261 in a perspective view, and FIG. 22a2 shows the exit port assembly 261 in a cross-section view. The exit port assembly 261 may be manufactured as one unitary component, for example, by 2-shot injection molding, with the rigid exit port sealing holder 262 and the soft exit port sealing 263 injected in separate shots using different materials as defined by the design described herein, and for instance, the exit port sealing holder 262 and the soft exit port sealing may be integrally formed. Alternatively, the exit port assembly 261 may be pre-manufactured by attaching two components, for example by gluing, by applying press-fit or any other technology resulting in a fluid-tight connection between the two components. In FIGS. 22a1 and 22a2, the multiple sealing function of the soft exit port sealing 263 is visible: the sealing not only covers the open distal end of the exit port channel 262a, but also includes a sealing area surrounding the exit port channel 262a to seal the interface to the housing and close the exit port opening 213a in an assembled state (see e.g., FIGS. 21a1 and 21a2). FIG. 22b shows a patch pump in an embodiment using the exit port assembly 261 of FIGS. 22a1 and 22a2, in a fully assembled state, including the needle assembly 260 with the output portion 260b.

Figure 23A:
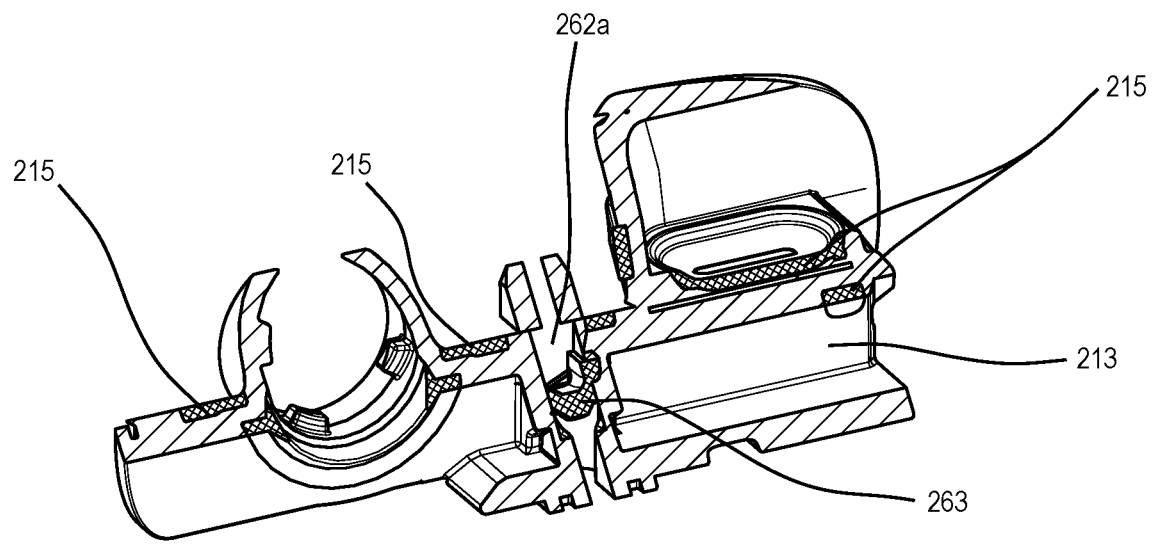
Figure 23B:
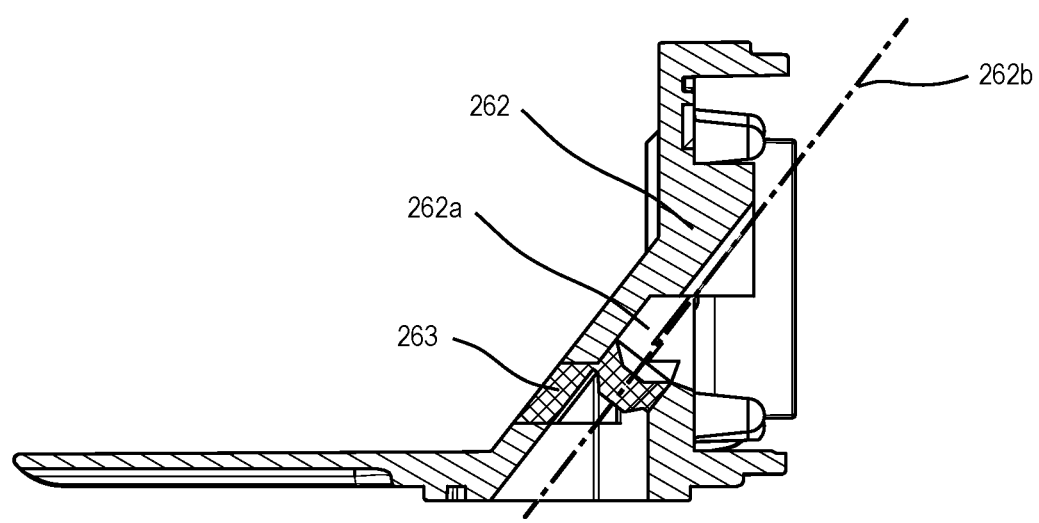
Figure 23C:
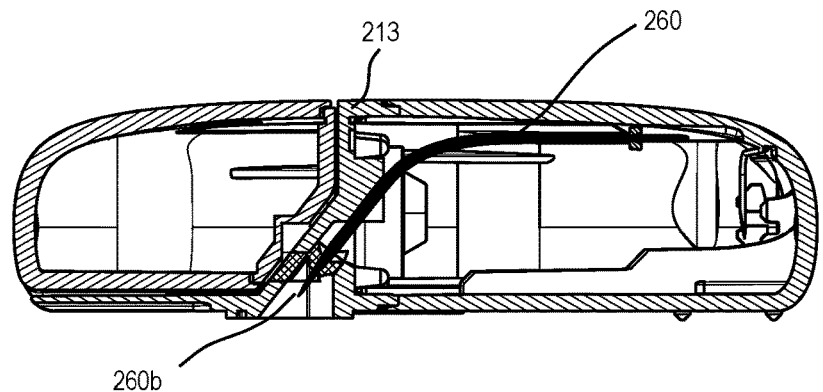
Figure 23C:
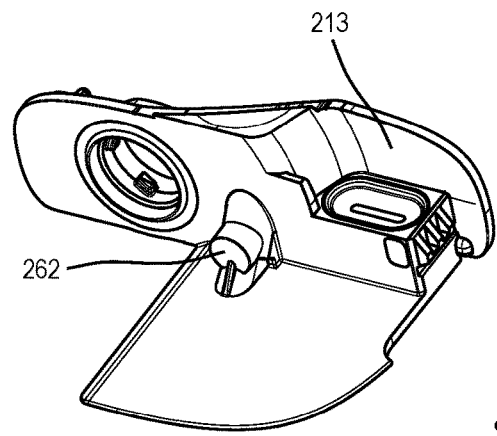
Figure 23C:
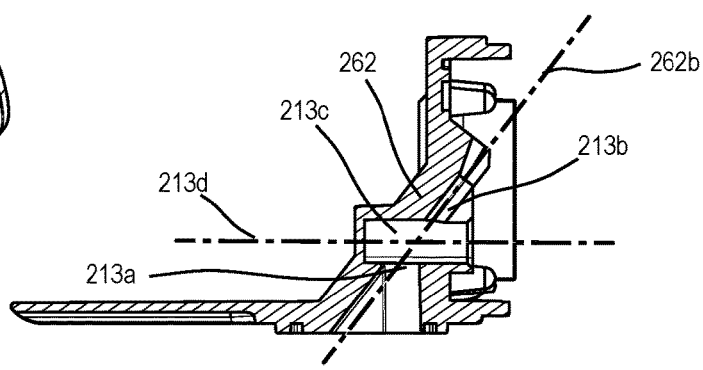

In a second group of implementations according to the sixth aspect of the present disclosure, the exit port may be improved by combining the exit port assembly 261 with one of the components of the housing into one unitary component. FIGS. 23a-23c illustrate one of many possible implementations of this group. FIG. 23a shows the first housing component 213 with all soft components attached in a perspective view with a cross-section along the exit port channel 262a axis. The first housing component 213 may be manufactured as one unitary component, for example by 2-shot injection molding with a soft material and a rigid material. The rigid exit port sealing holder 262 may be an element of the first housing component 213, may be made of rigid material, and may be manufactured for example in a first shot of injection molding. The soft exit port sealing 263 may be for example injected in a second shot of injection molding using soft materials as described herein. Materials may be selected to match the requirements of the drug delivery device, such as the fluid-tightness at the pressure specified for the exit port. An advantage of this group of embodiments may be that not only can the rigid exit port sealing holder 262 be integrated into the housing, but the soft exit port sealing 263 may also be combined with other sealings or functional elements requiring soft material on the same housing component. In FIGS. 23a and 23b, the multiple sealing function of the soft exit port sealing 263 is visible: the sealing not only covers the open distal end of the exit port channel 262a, but also may include housing sealings 215 in the housing designed for other purposes. Channels of soft material may connect the different sealing elements to improve manufacturability. Within the limits of manufacturability, any kind of housing component may be provided integrating the exit port assembly 261 with other housing elements as described in the present disclosure. FIG. 23b is a cross-section of the exit port assembly 261 of FIG. 23a to illustrate the shape of the soft exit port sealing 263 where it closes the distal end of the exit port channel 262a. FIG. 23c shows a patch pump in an implementation using the exit port assembly 261 of FIG. 23a, in a fully assembled state, including the needle assembly 260 with the output portion 260b.

In a third group of embodiments according to the sixth aspect of the present disclosure, the exit port may be improved by keeping the soft exit port sealing 263 as its own component and by improving manufacturability by introducing an exit port sealing plug cavity 213c configured to allow easy insertion of the soft exit port sealing 263. With this approach there may be no need to have an extra component as the rigid exit port sealing holder 262; the rigid exit port sealing holder may be consequently integrated into a housing component.

Figure 24B:
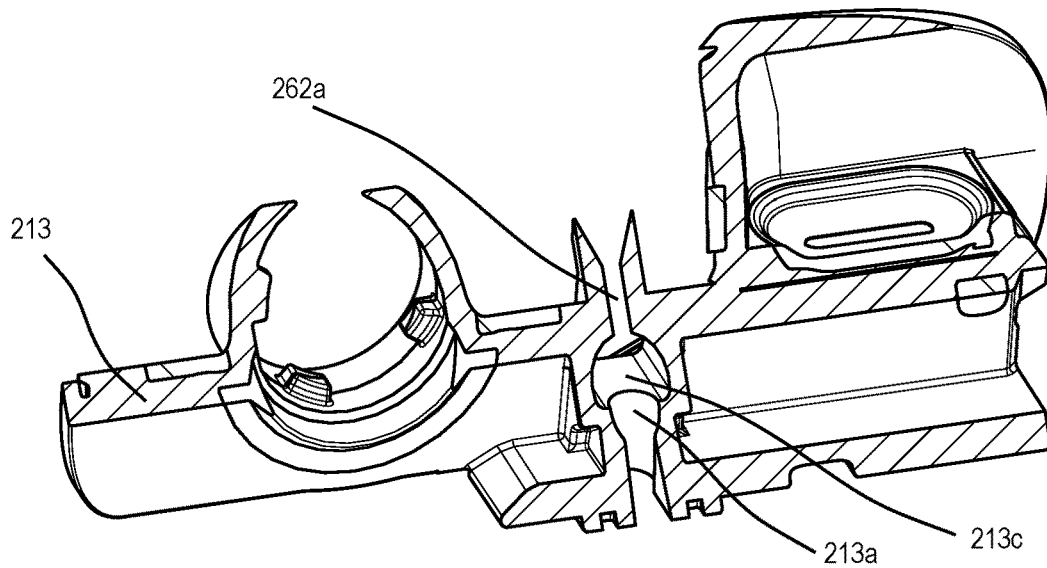
FIG. 24b depicts a cut through the exit port channel seen from inside the housing to further illustrate the exit port sealing plug cavity before assembly.
Figure 24C:
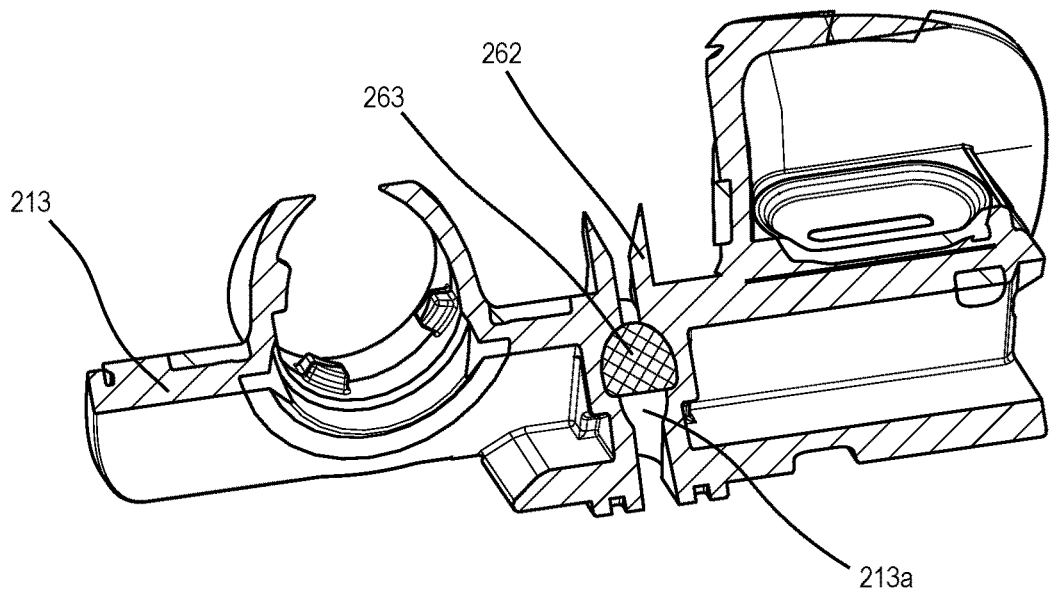
FIG. 24c depicts a cut through the exit port channel seen from inside the housing with the soft exit port sealing mounted into the exit port sealing plug cavity.

FIGS. 24a1-24d illustrate an implementation of this group. FIG. 24a1 shows the first housing component 213 in a perspective view, and FIG. 24a2 shows the first housing component in a cross-section view. The first housing component 213 may be manufactured as one unitary component, for example, by injection molding and may also integrate other elements like housing sealings 215 (cf. FIG. 23a). The rigid exit port sealing holder 262 may be an element of the first housing component 213, made of rigid material. The soft exit port sealing 263 may be manufactured as a separate component, for example, by injection molding using a different mold. In this group of implementations, the element of the first housing component may correspond to the rigid exit port sealing holder 262 and may have an exit port sealing plug cavity 213c, which may be at least partially tubular and intersecting the exit port channel 262a at a minimal angle of 10 degrees, such as between 45 and 90 degrees. In FIG. 24a2 this is illustrated by indicating the intersection of the exit port channel axis 262b and the exit port sealing plug cavity axis 213d. In this implementation, the exit port sealing plug cavity 213c may be open on an axial end. The soft exit port sealing 263 may easily be inserted into the exit port sealing plug cavity 213c along the exit port sealing plug cavity axis 213d and may provide a fluid-tight sealing of the exit port opening 213a. In this example, the exit port sealing may have a substantially cylindrical shape, but may have any other shape suitable for easy inserting through an open face of the exit port sealing plug cavity 231c, while closing the exit port opening 213a in a fully assembled state. Two figures are added to further explain the shape of the exit port sealing plug cavity 213c of this group of embodiments. FIG. 24b is a perspective view of the first housing component 213 with rigid exit port sealing holder 262 cross-section along the exit port channel axis 262b to show the shape of the exit port sealing plug cavity 213c. In FIG. 24c, the same view is shown, but with the soft exit port sealing 263 inserted in the rigid exit port sealing plug cavity 213c. In the example of FIGS. 24a1-24d both the exit port sealing plug cavity 213c and the soft exit port sealing 263 have substantially the shape of a cylinder with a segment cut away. This shape may be advantageous because the soft exit port sealing 263 may be inserted into the rigid exit port sealing holder like a cylindrical plug while the flat side provides better fixation during the piercing step. The minimal angle between the exit port sealing plug cavity 213c and the axis of the exit port channel 262b may facilitate the manufacturing step of piercing the exit port sealing with the output portion 260b of the needle assembly 260. A further advantage of said angle between the exit port sealing plug cavity axis 213d and the exit port channel axis 262b may be that when the output portion 260b of the needle assembly 260 is piercing through the soft exit port sealing 263, the soft exit port sealing 263 may be held in place by the rigid exit port sealing holder 262 with little or no shearing force or pulling force resulting at the connection between the soft exit port sealing 263 and the rigid exit port sealing holder 262, again improving the sealing to reliably meet the requirements for fluid-tightness as specified.

Figure 24D:
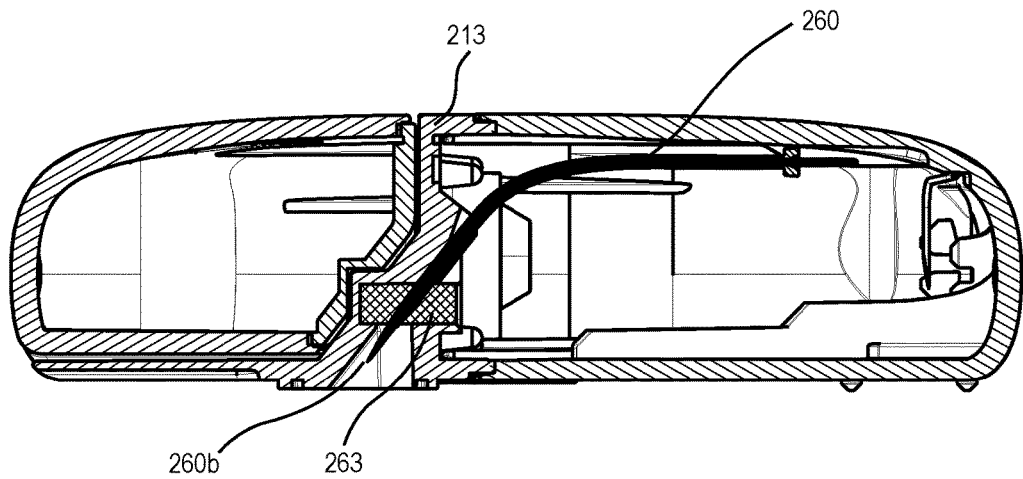
Figure 24D:
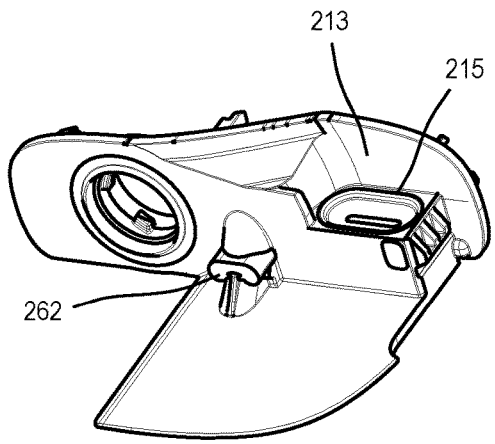
Figure 24D:
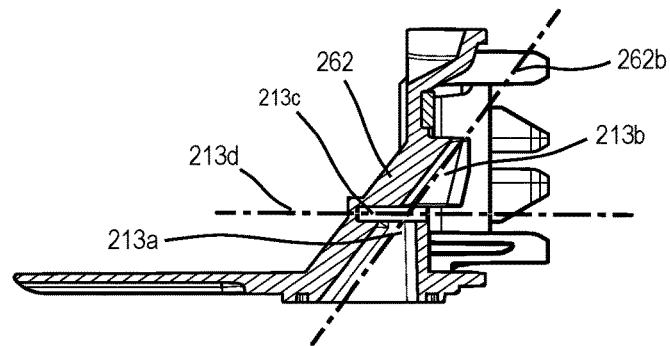

FIG. 24d shows a patch pump in an implementation using the exit port assembly 261 of FIGS. 24a1-24c, in a fully assembled state, including the needle assembly 260 with the output portion 260b.

Figure 25B:
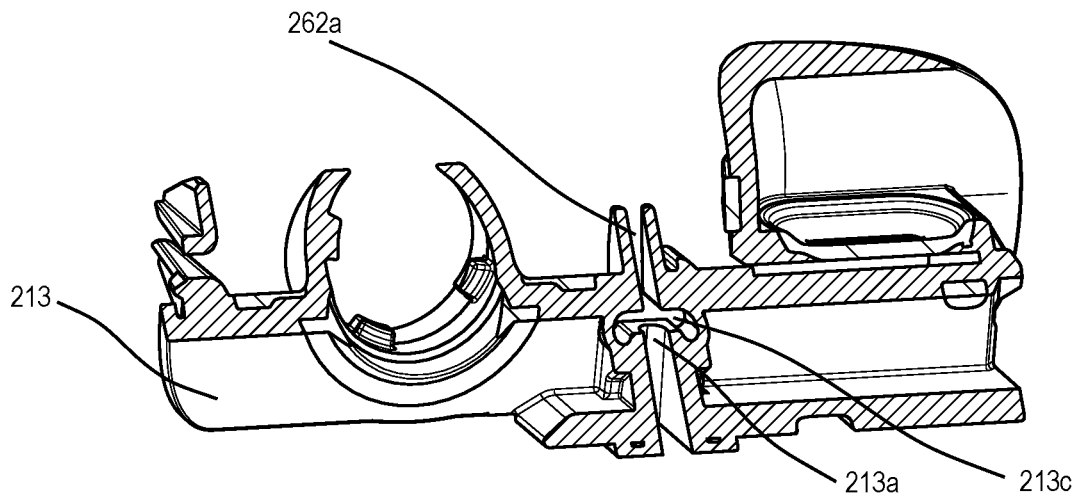
FIG. 25b depicts a cut through the exit port channel seen from inside the housing to further illustrate the exit port sealing plug cavity before assembly.
Figure 25C:
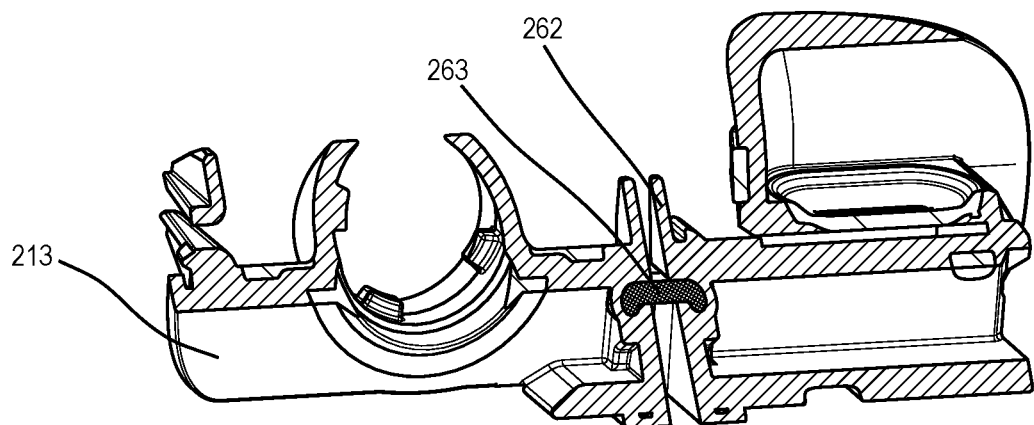
FIG. 25c depicts a cut through the exit port channel seen from inside the housing with the soft exit port sealing mounted into the exit port sealing plug cavity.

FIGS. 25a1-e illustrate another group of implementations similar to the one in FIGS. 24a1-24d. FIG. 25a1 shows the first housing component 213 in a perspective view, FIG. 25a2 shows the first housing component 213 in a cross-section view. Like before, the first housing component 213 may be manufactured as one unitary component, for example by injection molding and may also integrate other elements like housing sealings 215. The rigid exit port sealing holder 262 may be an element of the first housing component 213, made of rigid material. The soft exit port sealing 263 may be manufactured as a separate component, for example by injection molding using a different mold. Still, like the group in FIGS. 24a1-d, the element of the first housing component corresponding to the rigid exit port sealing holder 262 may have an exit port sealing plug cavity 213c, filled in FIGS. 25a1 and 25a2 with the soft exit port sealing 263. The exit port sealing plug cavity with exit port sealing plug cavity axis 213d may still intersect the exit port channel 262a with exit port channel axis 262b at a minimal angle of 10 degrees, or at between 45 and 90 degrees. However, in this group of embodiments, the exit port sealing may no longer be a stopper of a shape resembling a cylinder, but may have any other shape suitable to be pressed into the exit port sealing plug cavity through at least one open side. In such implementations, the exit port sealing cavity axis may no longer involve a rotational symmetry, but may include a path along which the soft exit port sealing 263 may be inserted into the rigid exit port sealing holder 262. To push a wide sealing a short way into a cavity—which can be seen as a sideways assembly of a stopper—may be easier than pushing a cylindrical sealing axially and may bring improvements to manufacturability. This group of embodiments may have the additional advantage that the exit port sealing plug cavity may be designed with a variety of shapes, for instance adding a constriction or flattening around the open distal end of the exit port channel to increase pressing and may facilitate providing fluid-tightness and pierceability in that area without impacting ease of assembly during manufacturing. For sideways insertion, the exit port sealing 263 may not be shaped like a cylinder, but rather more like a cushion or tablet, as shown in FIG. 25d1. Two figures are added to further explain the shape of the exit port sealing plug cavity of this group of embodiments. FIG. 25b is a perspective view of the first housing component 213 with rigid exit port sealing holder 262 cut along the exit port channel axis to show the shape of the exit port sealing plug cavity 213c. In FIG. 25c, the same view is shown, but with the soft exit port sealing 263 inserted in the rigid exit port sealing cavity. FIG. 25d1 shows the soft exit port sealing 263 before insertion into the exit port sealing plug cavity 262 of FIG. 25b, and FIG. 25d2 shows the soft exit port sealing 263 after insertion into the exit port sealing plug cavity 262 of FIG. 25b. As shown and described, the soft exit plug sealing 263 may be elastically deformed by this insertion and may be compressed with a flat surface at a substantially orthogonal angle at the point where the output portion 260b of the needle assembly 206 may pierce the sealing.

FIG. 25e shows a cross-section of a patch pump in an implementation using the exit port assembly 261 of FIG. 25a1-25e, in a fully assembled state, including the needle assembly 260 with the output portion 260b.

A seventh aspect of the present disclosure based on the wearable, semi-disposable patch pump shown in FIGS. 1a, 1b, 2a and 2b is provided as follows.

Figure 26A:
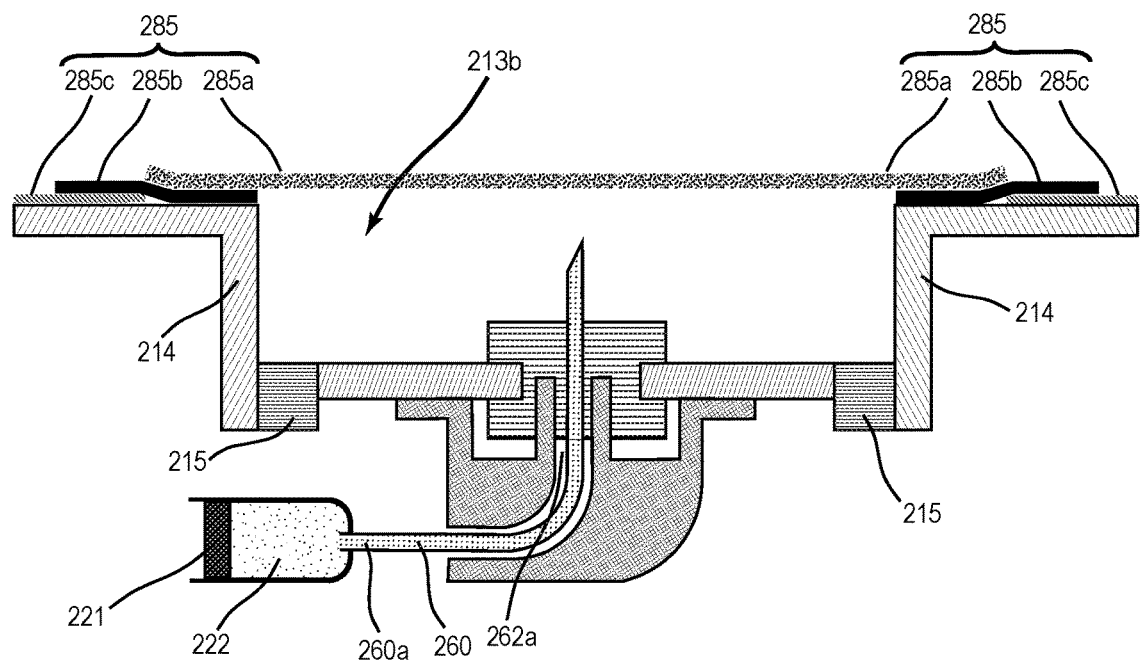
Figure 26B:
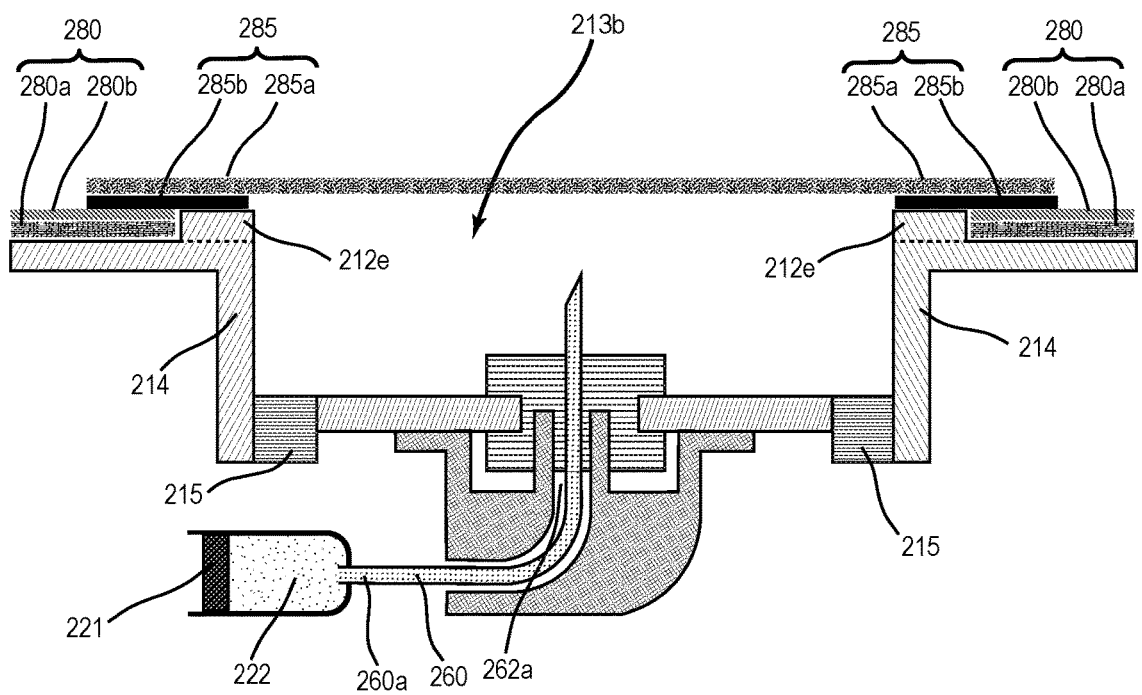
Figure 26C:
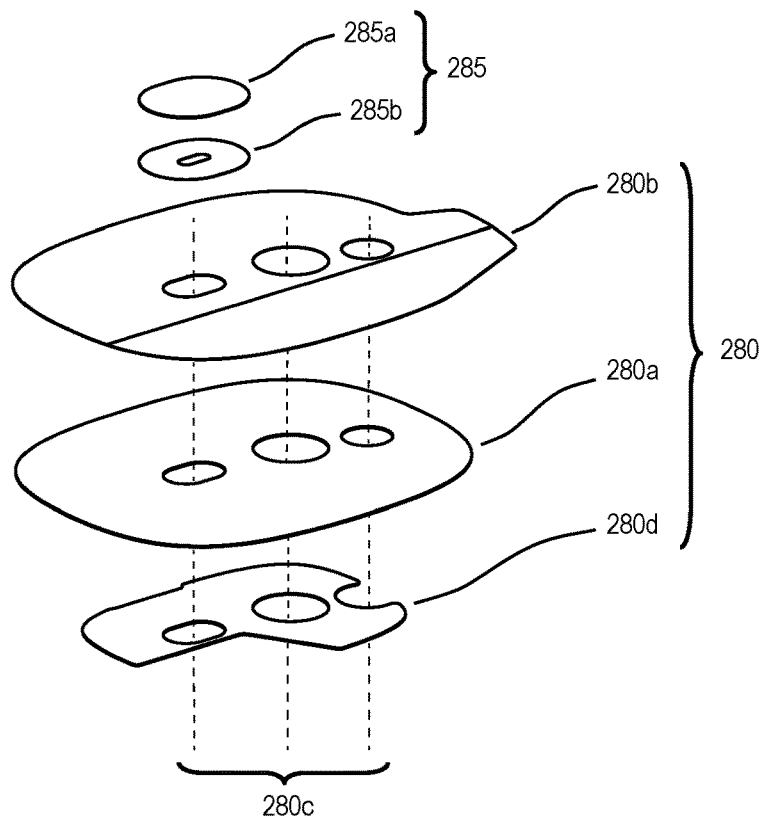

The patch pump may be further improved by covering the exit port chamber 213b with a semi-permeable exit port lid 285, which may be removably attached to a housing component 214 of the patch pump housing, as shown in FIGS. 26a-26c. The exit port lid 285 may be configured to be air permeable, while for example, preventing water or a fluid medicament from entering or leaving the exit port chamber 213b. With such an exit port lid 285, the needle assembly 260 and the reservoir 222 may be filled with medicament from the exterior without any of the fluid getting in contact with the patient. During filling of the reservoir 222 and/or priming of the fluid path through the needle assembly 260, the air initially present in the fluid path and/or in the exit port chamber 213b may be at least partially pressed through the exit port lid 285 and replaced by fluid. The fluid, however, may be stopped by the exit port lid 285. This may have two advantageous effects: first, as mentioned before, no drug may be spilled through the exit port while the exit port lid 285 is in place; second, the exit port lid 285 may close the fluid path and ensure that a filling pressure may be applied to the fluid required to move the plunger 221 and fill the reservoir 222. By supporting the process of filling the reservoir 222 and/or priming the fluid path, the exit port lid 285 of the present disclosure may contribute to safe and reliable functioning of the drug delivery device. The exit port lid 285 may include a priming membrane 285a made of a semi-permeable material, for instance provided in the form of a sheet, such as GoreTex® or similar products. Because such membranes may be mechanically weak, a membrane reinforcing structure 285b may be permanently, e.g., non-detachably, fixed to the priming membrane 285a, for instance in the area surrounding the exit port chamber 213b, as shown in the implementation of FIG. 26a. The membrane reinforcing structure 285b may for example be a plastic ring, a grid, a net or a sheet of textile material strong enough to allow removal of the exit port lid 285 without damaging the lid 285, and may be configured to allow contact of the fluid to the priming membrane 285a. The membrane reinforcing structure 285b may be removably attached to a housing component 214, for example, by means of glue, adhesive, or a double-sided adhesive tape. The double-sided adhesive tape may be the same as the membrane reinforcing structure 285b, with a first side sticking permanently to the priming membrane 285a, and a second side removably sticking to a housing component 214. The presence of the membrane reinforcing structure 285b may allow the exit port to be designed for fluid-tightness at a specified minimum pressure such as the filling pressure, while still ensuring easy handling of the pump.

In this implementation, the exit port lid 285 may further include an exit port lid liner 285c permanently, e.g., non-detachably, fixed to the membrane reinforcing structure 285b, but may not be attached to the housing component 214. Using the exit port lid liner 285c, the exit port lid 285 may easily be removed from the housing component 214 after successful filling and/or priming of the patch pump. As filling and priming are not functions only present in patch pumps, the disclosed implementations of the exit port lid may be applied to all kinds of drug delivery devices.

To achieve accuracy and reliability, patch pumps may keep the area around the output portion 260b of the needle assembly 260 securely attached to the body of the patient during drug delivery, for instance, with a fluid-tight connection. The exit port implementations with the exit port lid 285 may be further improved, for instance, by bringing the edge of the adhesive layer 280a to provide this fluid-tight connection closer to the exit port. This may be provided by integrating the exit port lid 285 into the adhesive patch assembly 280. An example of such an implementation is shown in FIG. 26b. The exit port lid 285 still includes the priming membrane 285a and the membrane reinforcing structure 285b. To bring the adhesive patch assembly 280 as close as possible to the border of the exit port chamber 213b, a membrane carrying structure 212e may be introduced. The membrane carrying structure 212e may be permanently, e.g., non-detachably, attached to a housing component 214, for instance, integrated therein as an element of the same unitary component. The membrane carrying structure 212e may have substantially the same thickness as the adhesive patch assembly 280 and may be shaped to surround the exit port chamber 213b in a way that a fluid-tight connection may be made between the housing component 214 and the exit port lid 285 as long as the exit port lid 285 is attached to the housing. An example may be a plastic ring integrated in or permanently attached to the housing component 214. In implementations, the adhesive patch assembly 280 may have an adhesive layer 280a and an adhesive release liner 280b. With the membrane carrying structure 212e in place, as described, the membrane reinforcing structure 285b may remain in substantially the same plane while being removably attached to the membrane carrying structure 212e and may be permanently, e.g., non-detachably, fixed to the adhesive release liner 280b. As before, the priming membrane 285a may be permanently fixed to the membrane reinforcing structure 285b. This arrangement may be easy to manufacture, may be optimized for fluid-tightness at a specified minimum pressure, may bring further cost advantage by removing the need for a dedicated exit port lid liner (285c, see FIG. 26a) and may facilitate ease of use. The exit port lid 285 may be removed from the exit port chamber 213b by removing the adhesive release liner 280b from the adhesive layer 280a—which may be a task the user has to do anyway to attach the patch pump to the body of the patient. FIG. 26c shows an implementation of an adhesive patch assembly 280 combined with an exit port lid 285 as described herein. The priming membrane 285a may be mounted on the adhesive release liner 280b using a double-sided adhesive ring which may also act as a membrane reinforcing structure 285b. An adhesive mounting tape 280d may be used to permanently attach the adhesive patch assembly 280 to the base plate 211a (not shown) at the bottom of the reservoir unit 200. A number of adhesive cut-outs 280c may be introduced at least in the adhesive layer 280a, for instance cut through all layers of the adhesive patch assembly 280, to allow access to the pump housing for functions such as filling the reservoir 222, bringing the needle assembly 260 into position for drug delivery or pressure compensation.

Further aspects of the exit port lid 285 in the scope of the present disclosure include a combination of the exit port lid 285 and/or the membrane carrying structure 212e with any other element on the pump housing or a combination of the exit port lid 285 with other functions. As an example of such extended functions, the attachment of the exit port lid 285 may be designed to break loose at low fluid pressure, deliberately allowing a leak to indicate to the user that the filling of the reservoir 222 has been successfully completed, or to indicate to the user that a maximum pressure has been exceeded.

An eighth aspect of the present disclosure based on the wearable, semi-disposable patch pump shown in FIGS. 1a, 1b, 2a and 2b is provided as follows.

Figure 27:
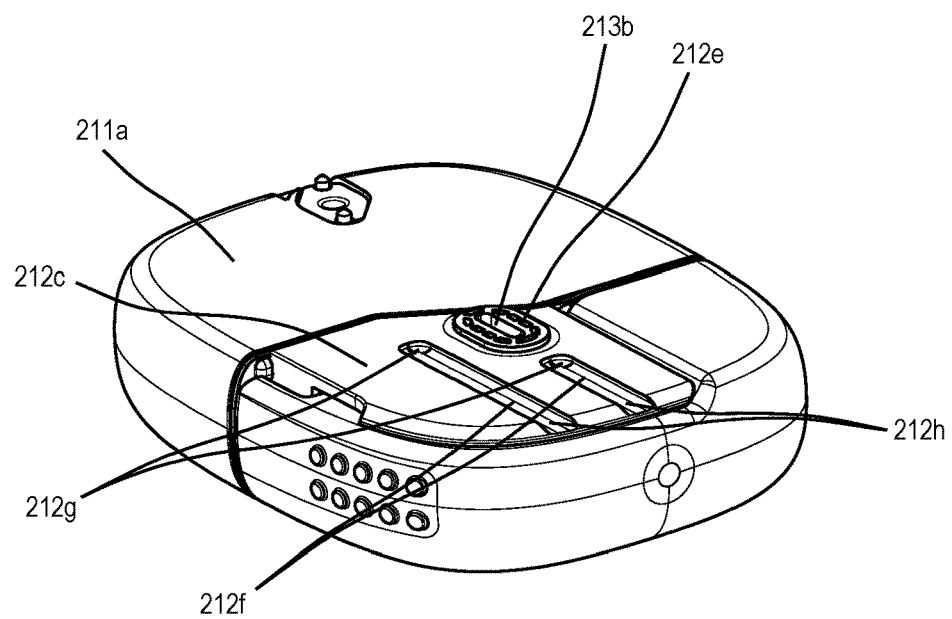
FIG. 27 depicts ventilation grooves at the bottom of a patch pump.

The patch pump may be further improved by introducing, at the interface between the patch pump and the body of the patient, a number of airing or venting channels. These airing or venting channels may allow air and humidity to escape the interface and enter the external environment. By doing so, the temperature and the humidity in the adhesive patch assembly 280 and surrounding components may be lowered, which may improve the adherence of the patch pump to the body of the patient, and hence may improve accuracy and reliability of the drug delivery. While similar airing or venting channels may be known, a combination with other aspects of the present disclosure may lead to a new solution, shown in FIG. 27. As described herein, it may be advantageous for the patch pump to keep the area around the output portion 260b of the needle assembly 260 securely attached to the body of the patient during drug delivery, for instance with a fluid-tight connection. Therefore, in implementations of the present disclosure, the airing channels may have no connection with the exit port chamber 213b, and may only start at a distance from the exit port chamber 213b which is large enough for the adhesive patch assembly 280 to ensure this fluid-tight connection, but small enough to improve adhesion in that area of the adhesive patch assembly 280. A range of distances may be 1 mm to 20 mm, such as 5 mm to 10 mm. In the implementation of FIG. 27, the airing channels may be provided as ventilation grooves 212f in the base plate 211a of the reservoir unit 200. This example may also include the membrane carrying structure 212e. Accordingly, the adhesive layer 280a may cover the complete base plate 211a including base plate extension 212c, with a cut-out for the exit port and for the membrane carrying structure 212e. In FIG. 27 the ventilation grooves 212f are shown arranged at a distance from the edge of the membrane carrying structure 212e. With the adhesive patch assembly 280 (not shown) mounted on the base plate 211a, The ventilation grooves 212f may be covered by the adhesive patch assembly 280, creating airing channels which may allow air and humidity to pass from the closed inner end 212g of the ventilation grooves 212f to the open outer end 212h of the ventilation grooves 212f and from there out into the environment at the exterior of the patch pump. In FIG. 27 it is also shown that these airing channels may have no connection with the exit port chamber 213b. It may be evident that the shape or number of the airing channels may be of no importance to their intended function. While the airing channels in FIG. 27 may be provided as two substantially straight half cylinders, they may have any other geometry, size, arrangement or placing on the base plate 211a or the base plate extension 212c, as long as they have no connection with the exit port chamber 213b and at least one open end towards the environment at the exterior of the pump.

The result may be a patch pump with improved airing or venting at the interface between the bottom of the pump and the body of the patient, while still allowing an optimum of fluid-tight connection between the two sides of the interface around the exit port chamber 213b, and may lead to improved accuracy and reliability of the drug delivery. Again, the arrangement of the present disclosure allows to design the housing of the pump and the adhesive patch assembly 280 to achieve fluid-tightness at the minimum fluid pressure specified for this interface.

While the present disclosure has been described in detail in the drawings and foregoing description, such description is to be considered illustrative or exemplary and not restrictive. Variations to the disclosed embodiments may be understood and effected by those skilled in the art and practicing the claimed implementations, from a study of the drawings, the disclosure, and the appended claims. Given the nature of the present disclosure having a number of aspects contributing to an overall optimum, it will be apparent to those skilled in the art that the improvements described, for better clarity, as different aspects, may be applied in any selection and/or combination. For example, a solution provided for an improved exit port sealing may well be used to improve the fill port or any other sealing in the drug delivery device. The fill port assembly may be combined with the exit port assembly to further optimise the pump. In the claims, the word "comprising" does not exclude other elements or steps, and the indefinite article "a" or "an" does not exclude a plurality. The mere fact that certain elements or steps are recited in distinct claims does not indicate that a combination of these elements or steps cannot be used to advantage, specifically, in addition to the actual claim dependency, any further meaningful claim combination shall be considered disclosed.

LIST OF REFERENCE NUMERALS

1 Patch pump
1a Enveloping surface
100 Pump unit
113 Locking mechanism
113a Locking spring
114 Opening side
120 Drive mechanism
122 Plunger rod
123 Plunger rod cap
125 Threaded rod
140 System control circuitry
141 Printed circuit board, PCB-PU
142 Connecting pins
150 Rechargeable battery
151 Battery contact
200 Reservoir unit
211 Reservoir unit housing
211a Base plate
211b Wall
211c Passage
211d First recessed section
211e Fixing pin
211f Second recessed section
211g Bottom wall
211h Side wall
211i Top wall
211j Protruding rim
211k Stabilizing recess
211m Cut-out
212a Bayonet connection
212b Rotational axis
212c Base plate extension
212d Locking structure
212e Membrane carrying structure
212f Ventilation groove
212g Inner end
212h Outer end 213 First housing component
213a Exit port opening
213b Exit port chamber
213c Exit port sealing plug cavity
213d Exit port sealing plug cavity axis
214 Housing component
215 Housing sealing
216 Pressure compensation membrane
221 Plunger
222 Reservoir
222a Reservoir inlet
222b Stabilizing protrusion
222c Reservoir outlet
222d Reservoir outlet sealing cavity
222e Reservoir axis
222f Reinforcing ribs
222g Fill port sealing cavity
223 Reservoir outlet sealing
230 Fill port assembly
231 Fill port sealing
231a Flange
231b Bore
231c Pierceable septum
231d Thermoplastic polymer
231e Elastomer
231f Cylindrical section
231g Cone-shaped opening
235 Needle guide/Insert
235a Cone shaped opening
235b Base
235c Sleeve
235d Opening or cut-out
238 First sealing
239 Second sealing
240 Hybrid assembly
241 Base frame
243 Printed circuit board, PCB-RU
244 Battery
245 Battery opening
246 Retaining element
250 Inserter assembly
251 Cannula moving assembly
252 Insertion spring
253 Soft cannula holder
254 Rigid cannula holder
256 Insertion trigger
258 Rigid cannula
259 Soft cannula
259a Soft cannula lumen
259b Soft cannula sealing, input portion
260 Needle assembly
260a Input portion
260b Output portion
261 Exit port assembly
262 Rigid exit port sealing holder
262a Exit port channel
262b Exit port channel axis
263 Soft exit port sealing
270 Connector structure
271a-271d Connector members
272 Contacting arm
272a First electrical contact area
272b Second electrical contact area
273 Switching arm
274 First battery contact arm
274a First battery contact area
275 Second battery contact arm
275a Second battery contact area
280 Adhesive patch assembly
280a Adhesive layer
280b Adhesive release liner
280c Adhesive cut-out
285 Exit port lid
285a Priming membrane
285b Membrane reinforcing structure
285c Exit port lid liner
290 Non-conductive body
291 First opening
292 Second opening
293 Fixing pins
294 Bearing pin
295 Upper guiding rail
296 Lower guiding rail
297 End stop surface
300 Patient

What is claimed is:

1. A drug delivery device, comprising:
a housing comprising an enveloping surface separating an interior volume from an exterior of the housing;
a reservoir arranged inside the housing configured to contain a drug;
a needle assembly comprising an input portion and an output portion; and
an exit port assembly,
wherein:
the housing comprises at least two components configured to be attached to one another to form a protective shell of the drug delivery device,
the reservoir comprises a reservoir outlet coupled to the input portion of the needle assembly,
the housing comprises an exit port opening to provide a passage for the output portion of the needle assembly from the interior of the housing to the exterior,
the exit port assembly is configured to form a fluid-tight connection between the housing and the output portion of the needle assembly,
the exit port assembly comprises a rigid exit port sealing holder comprising an at least partially tubular exit port channel defining an exit port channel axis configured to receive the output portion of the needle assembly; and
an exit port sealing plug cavity configured to attach a soft exit port sealing to the rigid exit port sealing holder,
wherein the soft exit port sealing is configured to provide a fluid-tight closure of the exit port opening of the housing,
wherein the exit port sealing plug cavity is open on at least one end to allow insertion of the soft exit port sealing along an exit port sealing plug cavity axis during manufacturing of the delivery device, and
wherein the soft exit port sealing is configured to tightly close the exit port sealing plug cavity and the exit port opening when mounted in the rigid exit port sealing holder.

2. The drug delivery device according to claim 1, wherein the exit port assembly is manufactured using a 2-shot injection molding process as a unitary component.

3. The drug delivery device according to claim 1, wherein the exit port assembly is manufactured using a 2-shot injection molding process as a unitary component with one or more of the at least two housing components.

4. The drug delivery device according to claim 1, wherein the exit port sealing plug cavity is arranged to intersect the exit port channel at an angle of at least 10 degrees between the exit port channel axis and the exit port sealing plug cavity axis.

5. The drug delivery device according to claim 4, wherein the exit port sealing plug cavity is arranged to intersect the exit port channel with an angle of at least 45 degrees between the exit port channel axis and the exit port sealing plug cavity axis.

6. The drug delivery device according to claim 4, wherein the exit port sealing plug cavity comprises a constriction and/or flattening at the exit port opening for pressing and/or shaping of the soft exit port sealing at an intersection with the exit port channel.

7. The drug delivery device according to claim 1, wherein the housing comprises a recess from the enveloping surface of the housing at the exit port opening, and wherein the recess in the housing forms an external exit port chamber between the recessed exit port opening and the enveloping surface of the housing.

8. The drug delivery device according to claim 7, wherein the needle assembly comprises a soft cannula with an open distal end, a rigid cannula at least partially and slidably disposed in an inner soft cannula lumen of the soft cannula, and a needle insertion mechanism configured to bring the output portion of the needle assembly with at least the open distal end of the soft cannula from a first position inside the exit port chamber to a second position outside the exit port chamber in the exterior of the housing.

9. The drug delivery device according to claim 7, further comprising an exit port lid, wherein:
the exit port lid is removably attached to the housing at a portion of the housing surrounding the exit port opening,
the exit port lid covers the exit port chamber such that fluid is prevented from entering or leaving the exit port chamber while air is permitted to pass therethrough;
the exit port lid comprises a semi-permeable membrane adapted to allow air to pass through while preventing a passage of liquid, and
the exit port lid comprises a membrane reinforcing structure affixed to the semi-permeable membrane configured to protect the semi-permeable membrane from damage during removal of the exit port lid from the housing.

10. The drug delivery device according to claim 9, wherein the membrane reinforcing structure comprises a plastic sheet and a cut-out configured for the exit port opening.

11. The drug delivery device according to claim 9, wherein the device is configured as a patch pump, wherein the device further comprises an adhesive patch assembly configured to attach the device to a patient, wherein:
the adhesive patch assembly comprises an adhesive layer configured to attach the adhesive patch assembly to the patient after a preparation of the device for drug delivery;
the adhesive patch assembly comprises a removable adhesive release liner covering the adhesive layer during the preparation of the device for drug delivery;
the exit port lid is non-detachably fixed to the adhesive release liner and removably connected to the housing; and
the exit port lid is configured to be removed from the housing together with the adhesive release liner during the preparation of the device for drug delivery.

12. The drug delivery device according to claim 11, wherein:
the housing further comprises a membrane carrying structure arranged around the exit port chamber,
the membrane carrying structure is adapted to protrude from the housing towards the exterior by a height substantially the same as a thickness of the adhesive patch assembly,
the membrane carrying structure is configured to provide contact with the exit port lid when the exit port lid is removably attached to the housing, and
the membrane carrying structure is configured to provide a fluid-tight connection between the exit port lid and the housing during preparation of the device for drug delivery and thereby tightly close the exit port chamber.

13. The drug delivery device according to claim 11, wherein:
the housing and/or the adhesive patch assembly further comprises at least one ventilation structure with at least one inner end closed and arranged at a horizontal distance of 1 mm to 20 mm from the exit port chamber, and at least one outer end left open and arranged at the peripheral edge of the housing and/or the adhesive, and
the ventilation structure is configured to be air-permeable from the inner end to the outer end of the device and to the environment at the exterior.

14. A method of manufacturing a drug delivery device, the method comprising, without implying any particular order or separation, the steps of:
manufacturing an exit port assembly by introducing a soft exit port sealing into an exit port sealing plug cavity and establishing a fluid-tight closure of an exit port opening of a housing of the drug delivery device, the exit port opening providing a passage for an output portion of a needle assembly from an interior of the housing to an exterior, wherein the needle assembly comprises an input portion and the output portion, and the input portion is coupled to a reservoir outlet of a reservoir configured to contain a drug, wherein the exit port assembly comprises a rigid exit port sealing holder comprising an at least partially tubular exit port channel defining an exit port channel axis configured to receive an output portion of a needle assembly;
attaching the rigid exit port sealing holder to at least one of at least two housing components of the housing, wherein the at least two housing components are configured to be attached to one another to form a protective shell of the drug delivery device; and
piercing the soft exit port sealing with the output portion of the needle assembly,
wherein the exit port assembly is configured to form a fluid-tight connection between the housing and the output portion of the needle assembly.

* * * * *